(12) United States Patent
Larson et al.

(10) Patent No.: US 11,559,624 B2
(45) Date of Patent: Jan. 24, 2023

(54) SYSTEMS FOR WEARABLE INFUSION PORT AND ASSOCIATED PUMP

(71) Applicant: MEDTRONIC MINIMED, INC., Northridge, CA (US)

(72) Inventors: Eric Allan Larson, Simi Valley, CA (US); Shixin Chen, Simi Valley, CA (US); Magnus Johansson, Oak Park, CA (US); Louis J. Lintereur, Stevenson Ranch, CA (US); Austin Reeder, Los Angeles, CA (US); Peter Schultz, Chatsworth, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 538 days.

(21) Appl. No.: 16/691,506

(22) Filed: Nov. 21, 2019

(65) Prior Publication Data

US 2021/0154394 A1 May 27, 2021

(51) Int. Cl.
*A61M 5/142* (2006.01)
*A61M 5/168* (2006.01)

(52) U.S. Cl.
CPC .... *A61M 5/14244* (2013.01); *A61M 5/16881* (2013.01); *A61M 2205/3337* (2013.01); *A61M 2205/3576* (2013.01)

(58) Field of Classification Search
CPC .......... A61M 5/14244; A61M 5/16881; A61M 2205/3337; A61M 2205/3576;

(Continued)

(56) References Cited

U.S. PATENT DOCUMENTS

| 4,755,173 A | 7/1988 | Konopka et al. |
| 4,772,263 A | 9/1988 | Dorman et al. |

(Continued)

FOREIGN PATENT DOCUMENTS

| EP | 1549382 B1 | 3/2016 |
| EP | 3244946 B1 | 9/2020 |

OTHER PUBLICATIONS

Smart Insulin Injection Port Concept, Cambridge Consultants Ltd., www.CambridgeConsultants.com, 2017.

(Continued)

*Primary Examiner* — Jason E Flick
(74) *Attorney, Agent, or Firm* — Fortem IP LLP; Matthew Lincicum

(57) ABSTRACT

A wearable infusion port for infusing a fluid includes a first housing that defines an inlet port to receive the fluid, and a second housing coupled to the first housing. The second housing is to be coupled to an anatomy. The wearable infusion port includes a valve assembly fluidly coupled to the inlet port, and the valve assembly is movable from a closed state to an opened state to dispense the fluid. The wearable infusion port includes a cannula assembly extending through the first housing and the second housing, and the cannula assembly includes a cannula fluidly coupled to the valve assembly. The cannula is to be coupled to the anatomy. The wearable infusion port includes a flow sensor fluidly coupled to the inlet port and the cannula. The flow sensor is fluidly coupled upstream from the cannula to observe an amount of fluid received by the cannula.

18 Claims, 31 Drawing Sheets

(58) Field of Classification Search
CPC ........ A61M 5/14; A61M 5/142; A61M 5/168; A61M 5/16877; A61M 5/16886; A61M 5/16804; A61M 2205/3331; A61M 2205/3334
See application file for complete search history.

(56) References Cited

U.S. PATENT DOCUMENTS

| | | | |
|---|---|---|---|
| 5,391,250 A | 2/1995 | Cheney, II et al. | |
| 5,485,408 A | 1/1996 | Blomquist | |
| 5,522,803 A | 6/1996 | Teissen-Simony | |
| 5,665,065 A | 9/1997 | Colman et al. | |
| 5,800,420 A | 9/1998 | Gross et al. | |
| 5,807,375 A | 9/1998 | Gross et al. | |
| 5,925,021 A | 7/1999 | Castellano et al. | |
| 5,954,643 A | 9/1999 | Van Antwerp et al. | |
| 6,017,328 A | 1/2000 | Fischell et al. | |
| 6,186,982 B1 | 2/2001 | Gross et al. | |
| 6,246,992 B1 | 6/2001 | Brown | |
| 6,248,067 B1 | 6/2001 | Causey, III et al. | |
| 6,248,093 B1 | 6/2001 | Moberg | |
| 6,355,021 B1 | 3/2002 | Nielsen et al. | |
| 6,379,301 B1 | 4/2002 | Worthington et al. | |
| 6,544,212 B2 | 4/2003 | Galley et al. | |
| 6,558,351 B1 | 5/2003 | Steil et al. | |
| 6,589,229 B1 * | 7/2003 | Connelly .......... A61M 5/14248 604/890.1 | |
| 6,591,876 B2 | 7/2003 | Safabash | |
| 6,641,533 B2 | 11/2003 | Causey, III et al. | |
| 6,736,797 B1 | 5/2004 | Larsen et al. | |
| 6,749,587 B2 | 6/2004 | Flaherty | |
| 6,766,183 B2 | 7/2004 | Walsh et al. | |
| 6,801,420 B2 | 10/2004 | Talbot et al. | |
| 6,804,544 B2 | 10/2004 | Van Antwerp et al. | |
| 6,892,085 B2 | 5/2005 | McIvor et al. | |
| 7,003,336 B2 | 2/2006 | Holker et al. | |
| 7,029,444 B2 | 4/2006 | Shin et al. | |
| 7,066,909 B1 | 6/2006 | Peter et al. | |
| 7,137,964 B2 | 11/2006 | Flaherty | |
| 7,303,549 B2 | 12/2007 | Flaherty et al. | |
| 7,399,277 B2 | 7/2008 | Saidara et al. | |
| 7,442,186 B2 | 10/2008 | Blomquist | |
| 7,468,033 B2 | 12/2008 | Van Antwerp et al. | |
| 7,602,310 B2 | 10/2009 | Mann et al. | |
| 7,647,237 B2 | 1/2010 | Malave et al. | |
| 7,699,807 B2 | 4/2010 | Faust et al. | |
| 7,727,148 B2 | 6/2010 | Talbot et al. | |
| 7,785,313 B2 | 8/2010 | Mastrototaro | |
| 7,806,886 B2 | 10/2010 | Kanderian, Jr. et al. | |
| 7,819,843 B2 | 10/2010 | Mann et al. | |
| 7,828,764 B2 | 11/2010 | Moberg et al. | |
| 7,879,010 B2 | 2/2011 | Hunn et al. | |
| 7,890,295 B2 | 2/2011 | Shin et al. | |
| 7,892,206 B2 | 2/2011 | Moberg et al. | |
| 7,892,748 B2 | 2/2011 | Norrild et al. | |
| 7,901,394 B2 | 3/2011 | Ireland et al. | |
| 7,942,844 B2 | 5/2011 | Moberg et al. | |
| 7,946,985 B2 | 5/2011 | Mastrototaro et al. | |
| 7,955,305 B2 | 6/2011 | Moberg et al. | |
| 7,963,954 B2 | 6/2011 | Kavazov | |
| 7,977,112 B2 | 7/2011 | Burke et al. | |
| 7,979,259 B2 | 7/2011 | Brown | |
| 7,985,330 B2 | 7/2011 | Wang et al. | |
| 8,024,201 B2 | 9/2011 | Brown | |
| 8,100,852 B2 | 1/2012 | Moberg et al. | |
| 8,114,268 B2 | 2/2012 | Wang et al. | |
| 8,114,269 B2 | 2/2012 | Cooper et al. | |
| 8,137,314 B2 | 3/2012 | Mounce et al. | |
| 8,181,849 B2 | 5/2012 | Bazargan et al. | |
| 8,182,462 B2 | 5/2012 | Istoc et al. | |
| 8,192,395 B2 | 6/2012 | Estes et al. | |
| 8,195,265 B2 | 6/2012 | Goode, Jr. et al. | |
| 8,202,250 B2 | 6/2012 | Stutz, Jr. | |
| 8,207,859 B2 | 6/2012 | Enegren et al. | |
| 8,226,615 B2 | 7/2012 | Bikovsky | |
| 8,257,259 B2 | 9/2012 | Brauker et al. | |
| 8,267,921 B2 | 9/2012 | Yodfat et al. | |
| 8,275,437 B2 | 9/2012 | Brauker et al. | |
| 8,277,415 B2 | 10/2012 | Mounce et al. | |
| 8,292,849 B2 | 10/2012 | Bobroff et al. | |
| 8,298,172 B2 | 10/2012 | Nielsen et al. | |
| 8,303,572 B2 | 11/2012 | Adair et al. | |
| 8,305,580 B2 | 11/2012 | Aasmul | |
| 8,308,679 B2 | 11/2012 | Hanson et al. | |
| 8,313,433 B2 | 11/2012 | Cohen et al. | |
| 8,318,443 B2 | 11/2012 | Norrild et al. | |
| 8,323,250 B2 | 12/2012 | Chong et al. | |
| 8,343,092 B2 | 1/2013 | Rush et al. | |
| 8,352,011 B2 | 1/2013 | Van Antwerp et al. | |
| 8,353,829 B2 | 1/2013 | Say et al. | |
| 9,101,305 B2 | 8/2015 | Larson et al. | |
| 9,295,786 B2 | 3/2016 | Gottlieb et al. | |
| 10,363,361 B2 | 7/2019 | Arnitz | |
| 11,324,881 B2 | 5/2022 | Larson et al. | |
| 2003/0176852 A1 | 9/2003 | Lynch et al. | |
| 2007/0123819 A1 | 5/2007 | Mernoe et al. | |
| 2009/0062747 A1 | 3/2009 | Saul | |
| 2009/0299301 A1 | 12/2009 | Gottlieb et al. | |
| 2010/0160861 A1 | 6/2010 | Causey, III et al. | |
| 2013/0184541 A1 * | 7/2013 | Antonio .............. A61B 5/0002 604/533 |
| 2016/0015892 A1 | 1/2016 | Turner et al. | |
| 2021/0154395 A1 | 5/2021 | Larson et al. | |

OTHER PUBLICATIONS

International Search Report and Written Opinion of International Application No. PCT/US2020/058496, dated Feb. 16, 2021, 15 pp.

* cited by examiner

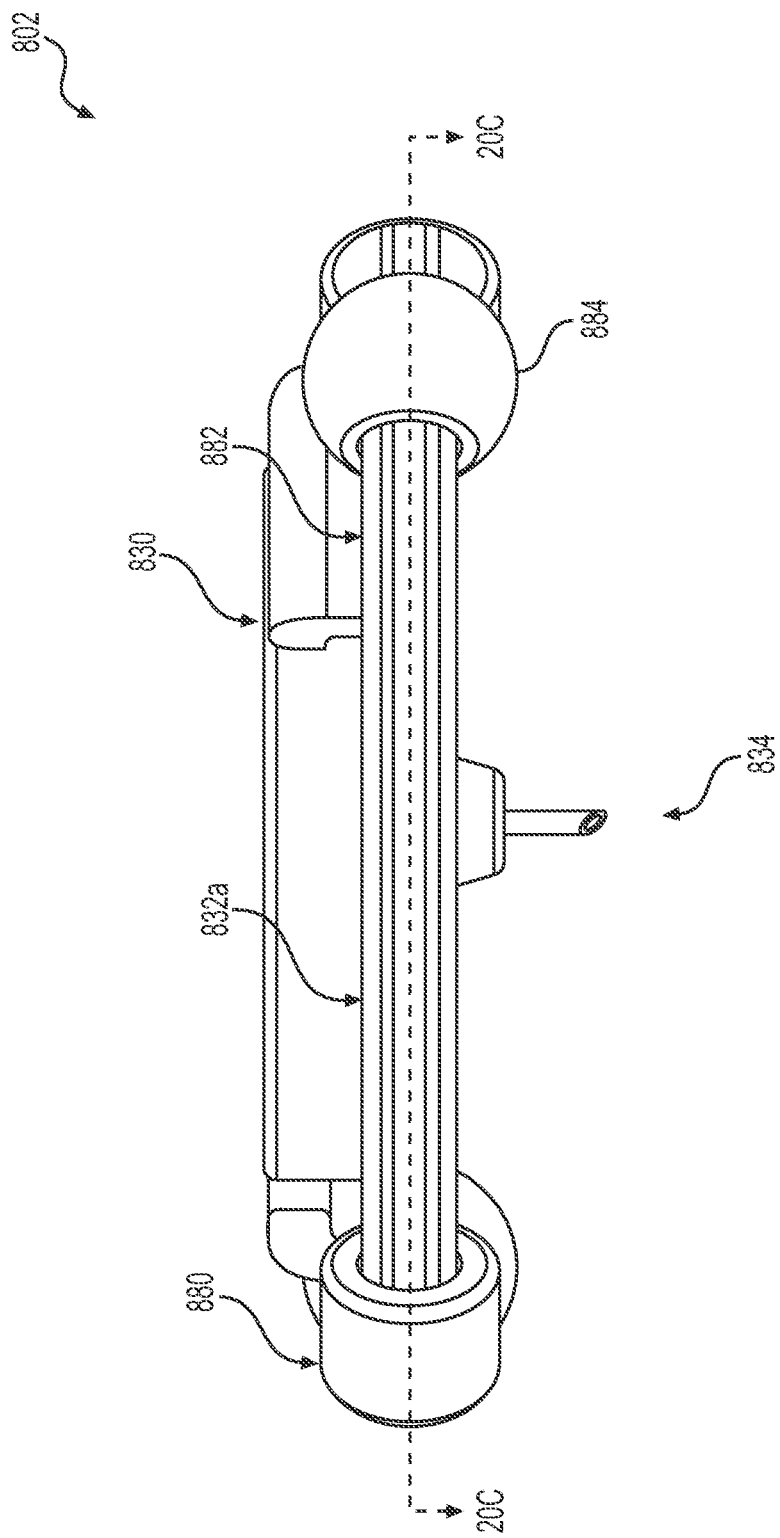

SYSTEMS FOR WEARABLE INFUSION PORT AND ASSOCIATED PUMP

FIELD

Embodiments of the subject matter described herein relate generally to medical devices, such as a wearable infusion port and a pump associated with the wearable infusion port for providing the infusion port with a fluid. More particularly, embodiments of the subject matter relate to systems that provide a wearable infusion port that is coupled to a user to provide an infusion therapy for an extended period of time, and a pump that interfaces with the wearable infusion port to provide the infusion port with the fluid.

BACKGROUND

Certain diseases or conditions may be treated, according to modern medical techniques, by delivering a medication or other substance to the body of a user, either in a continuous manner or at particular times or time intervals within an overall time period. For example, diabetes is commonly treated by delivering defined amounts of insulin to the user at appropriate times. Some common modes of providing insulin therapy to a user include delivery of insulin through manually operated syringes and insulin pens.

The use of manually operated syringes and insulin pens requires a user to inject the insulin directly into their anatomy. Some users, however, are uncomfortable with injecting themselves directly with insulin. In addition, in certain instances, the user may need to directly inject insulin multiple times over a course of a day. This results in the user being subjected to multiple injections, which may be uncomfortable for the user. In addition, for users who require multiple doses of the fluid over the course of the day, multiple syringes are needed to provide the fluid for injection. It may be inconvenient for the user to carry the multiple syringes.

Accordingly, it is desirable to provide systems for a wearable infusion port, which enables a user to inject the fluid, such as insulin, into the port, instead of their anatomy. Moreover, it is desirable to provide systems for a wearable infusion port, which enables the user to reduce a number of times their anatomy is pierced to deliver the infusion therapy. In addition, it is desirable to provide a pump to supply the wearable infusion port with the fluid, such as insulin, which is capable of containing a quantity of fluid that is greater than one dose. Furthermore, other desirable features and characteristics will become apparent from the subsequent detailed description and the appended claims, taken in conjunction with the accompanying drawings and the foregoing technical field and background.

BRIEF SUMMARY

The techniques of this disclosure generally relate to systems that provide a wearable infusion port for infusing a fluid into an anatomy, such as insulin, and a pump associated with the wearable infusion port for supplying the wearable infusion port with a quantity of the infusion fluid.

According to various embodiments, a wearable infusion port for infusing a fluid is provided. The wearable infusion port includes a first housing that defines an inlet port to receive the fluid, and a second housing coupled to the first housing. The second housing is to be coupled to an anatomy. The wearable infusion port includes a valve assembly fluidly coupled to the inlet port to receive the fluid, and the valve assembly is movable from a closed state to an opened state to dispense the fluid. The wearable infusion port further includes a cannula assembly extending through the first housing and the second housing, and the cannula assembly includes a cannula fluidly coupled to the valve assembly to receive the fluid. The cannula is to be coupled to the anatomy to infuse the fluid into the anatomy. The wearable infusion port includes a flow sensor fluidly coupled to the inlet port and the cannula. The flow sensor is fluidly coupled upstream from the cannula to observe an amount of fluid received by the cannula.

Further provided is a wearable infusion port for infusing a fluid. The wearable infusion port includes a first housing that defines an inlet port to receive the fluid and a second housing coupled to the first housing. The second housing is to be coupled to an anatomy. The wearable infusion port includes a valve assembly fluidly coupled to the inlet port to receive the fluid, and the valve assembly is movable from a closed state to an opened state to dispense the fluid. The wearable infusion port includes a cannula assembly extending through the first housing and the second housing, and the cannula assembly includes a cannula fluidly coupled to the valve assembly to receive the fluid. The cannula is to be coupled to the anatomy to infuse the fluid into the anatomy. The wearable infusion port further includes a physiological characteristic sensor coupled to the first housing proximate an end of the first housing and spaced apart from the inlet port, and the physiological characteristic sensor is to be coupled to the anatomy to observe a physiological characteristic associated with the anatomy.

Also provided is a wearable infusion port for infusing a fluid. The wearable infusion port includes a first housing that defines an inlet port to receive the fluid, and a second housing coupled to the first housing. The second housing is to be coupled to an anatomy. The wearable infusion port includes a valve assembly fluidly coupled to the inlet port to receive the fluid. The valve assembly includes a valve housing and a shaft defining a shaft conduit downstream from the inlet port. The shaft movable relative to the housing to move the valve assembly between a closed state and an opened state to dispense the fluid. The wearable infusion port includes a cannula assembly extending through the first housing and the second housing, the cannula assembly including a cannula fluidly coupled to the valve assembly to receive the fluid in the opened state, the cannula is to be coupled to the anatomy to infuse the fluid into the anatomy.

According to various embodiments, also provided is a pump for delivering a fluid. The pump includes a pump housing that defines at least one reservoir having a circumferentially open first end, a circumferentially closed second end and a chamber defined between the first end and the second end to receive the fluid. The pump includes a plunger assembly having at least one plunger arm and a cannula fluidly coupled to the at least one plunger arm to dispense the fluid from the pump. The at least one plunger arm is receivable within the first end of the at least one fluid reservoir, and the at least one plunger arm defining an internal conduit to receive the fluid from the at least one fluid reservoir. The internal conduit is fluidly coupled to the cannula. The plunger assembly is movable in a first direction relative to the pump housing to advance the at least one plunger arm within the at least one fluid reservoir to dispense the fluid from the at least one fluid reservoir out of the pump via the cannula.

Further provided is a pump for delivering a fluid. The pump includes a pump housing that defines at least one reservoir having a circumferentially open first end, a circumferentially closed second end and a chamber defined between the first end and the second end to receive the fluid. The pump includes a plunger assembly having a plunger base, at least one plunger arm and a cannula. The at least one plunger arm is coupled to a perimeter of the plunger base and the cannula is coupled proximate a center of the plunger base. The at least one plunger arm is receivable within the first end of the at least one fluid reservoir, and the at least one plunger arm defines an internal conduit to receive the fluid from the at least one fluid reservoir. The internal conduit is fluidly coupled to a base conduit defined in the plunger base, and the base conduit is fluidly coupled to the cannula. The plunger assembly is movable in a first direction relative to the pump housing to advance the at least one plunger arm within the at least one fluid reservoir to dispense the fluid from the at least one fluid reservoir out of the pump via the cannula.

Also provided is a pump for delivering a fluid. The pump includes a pump housing that defines at least one reservoir having a circumferentially open first end, a circumferentially closed second end and a chamber defined between the first end and the second end to receive the fluid. The pump includes a plunger assembly having a plunger base, at least one plunger arm and a cannula. The at least one plunger arm is coupled to a perimeter of the plunger base and the cannula is coupled proximate a center of the plunger base. The at least one plunger arm is receivable within the first end of the at least one fluid reservoir, and the at least one plunger arm defines an internal conduit to receive the fluid from the at least one fluid reservoir. The internal conduit is fluidly coupled to a base conduit defined in the plunger base. The base conduit is fluidly coupled to the cannula. The plunger assembly is movable in a first direction relative to the pump housing to advance the at least one plunger arm within the at least one fluid reservoir to dispense the fluid from the at least one fluid reservoir out of the pump via the cannula. The pump also includes a lock system coupled to the pump housing between the pump housing and the plunger base. The lock system is movable to move the plunger assembly between a first, unlocked position in which the plunger assembly is movable relative to the pump housing to dispense the fluid and a second, locked position in which the plunger assembly is fixed relative to the pump housing.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter. The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

FIG. 20B is a side view of the plunger assembly associated with the pump;

DETAILED DESCRIPTION

Figure 1:
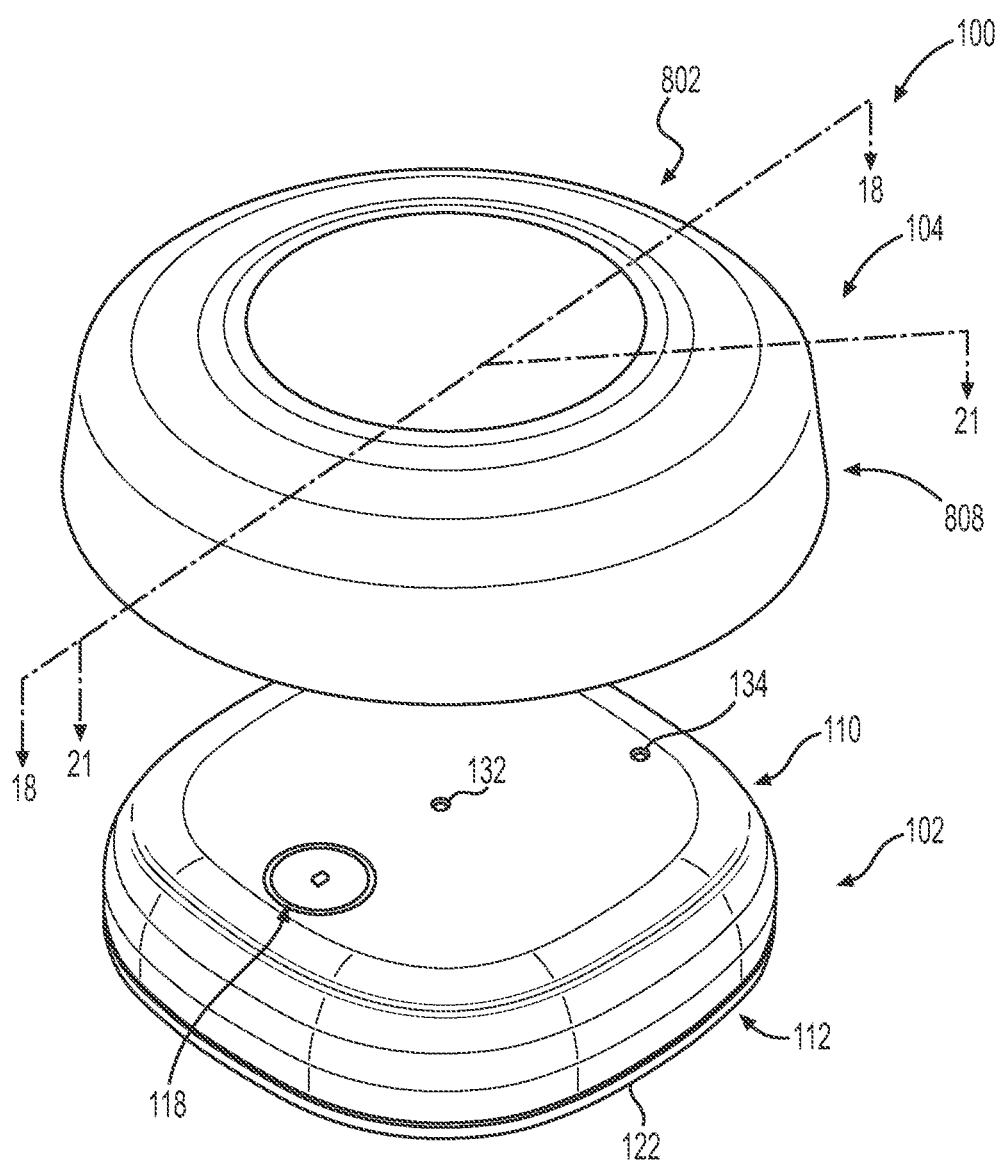
FIG. 1 is a perspective view of an infusion system that includes a wearable infusion port and a pump for dispensing a fluid into the wearable infusion port according to various teachings of the present disclosure.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

Certain terminology may be used in the following description for the purpose of reference only, and thus are not intended to be limiting. For example, terms such as "top", "bottom", "upper", "lower", "above", and "below" could be used to refer to directions in the drawings to which reference is made. Terms such as "front", "back", "rear", "side", "outboard", and "inboard" could be used to describe the orientation and/or location of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second", and other such numerical terms referring to structures do not imply a sequence or order unless clearly indicated by the context.

As used herein, the term "axial" refers to a direction that is generally parallel to or coincident with an axis of rotation, axis of symmetry, or centerline of a component or components. For example, in a cylinder or disc with a centerline and generally circular ends or opposing faces, the "axial" direction may refer to the direction that generally extends in parallel to the centerline between the opposite ends or faces. In certain instances, the term "axial" may be utilized with respect to components that are not cylindrical (or otherwise radially symmetric). For example, the "axial" direction for a rectangular housing containing a rotating shaft may be viewed as a direction that is generally parallel to or coincident with the rotational axis of the shaft. Furthermore, the term "radially" as used herein may refer to a direction or a relationship of components with respect to a line extending outward from a shared centerline, axis, or similar reference, for example in a plane of a cylinder or disc that is perpendicular to the centerline or axis. In certain instances, components may be viewed as "radially" aligned even though one or both of the components may not be cylindrical (or otherwise radially symmetric). Furthermore, the terms "axial" and "radial" (and any derivatives) may encompass directional relationships that are other than precisely aligned with (e.g., oblique to) the true axial and radial dimensions, provided the relationship is predominantly in the respective nominal axial or radial direction. As used herein, the term "transverse" denotes an axis that crosses another axis at an angle such that the axis and the other axis are neither substantially perpendicular nor substantially parallel.

The following description relates to various embodiments of systems for wearable infusion ports, and a pump to supply fluid to a wearable infusion port. The wearable infusion ports described herein enable a user to receive infusion therapy, such as insulin infusion therapy, over an extended period of time with a single injection site. The wearable infusion port enables the user to receive infusion therapy without directly injecting their anatomy with a syringe or insulin pen, for example. In addition, the pump is configured to interface with the wearable infusion port to supply the wearable infusion port with a quantity of the infusion fluid, such as insulin. The pump may also be configured as a patch pump, which may be coupled to the anatomy of a user via an adhesive patch for example.

It should be noted that while the wearable infusion port and the pump are each described herein as being used to treat diabetes, embodiments of the disclosed subject matter are not so limited. Accordingly, the infused medication fluid is insulin in certain embodiments. In alternative embodiments, however, many other fluids may be administered through infusion such as, but not limited to, disease treatments, drugs to treat pulmonary hypertension, iron chelation drugs, pain medications, anti-cancer treatments, medications, vitamins, hormones, or the like. For the sake of brevity, conventional features and characteristics related to infusion system operation, insulin pump and/or infusion set operation, fluid reservoirs, and fluid syringes may not be described in detail here.

As used herein, the term module refers to any hardware, software, firmware, electronic control component, processing logic, and/or processor device, individually or in any combination, including without limitation: application specific integrated circuit (ASIC), an electronic circuit, a processor (shared, dedicated, or group) and memory that executes one or more software or firmware programs, a combinational logic circuit, and/or other suitable components that provide the described functionality.

Embodiments of the present disclosure may be described herein in terms of functional and/or logical block components and various processing steps. It should be appreciated that such block components may be realized by any number of hardware, software, and/or firmware components configured to perform the specified functions. For example, an embodiment of the present disclosure may employ various integrated circuit components, e.g., memory elements, digital signal processing elements, logic elements, look-up tables, or the like, which may carry out a variety of functions under the control of one or more microprocessors or other control devices. In addition, those skilled in the art will appreciate that embodiments of the present disclosure may be practiced in conjunction with any number of systems, and that the systems described herein is merely exemplary embodiments of the present disclosure.

For the sake of brevity, conventional techniques related to signal processing, data transmission, signaling, control, machine learning models, and other functional aspects of the systems (and the individual operating components of the systems) may not be described in detail herein. Furthermore, the connecting lines shown in the various figures contained herein are intended to represent example functional relationships and/or physical couplings between the various elements. It should be noted that many alternative or additional functional relationships or physical connections may be present in an embodiment of the present disclosure.

Figure 2:
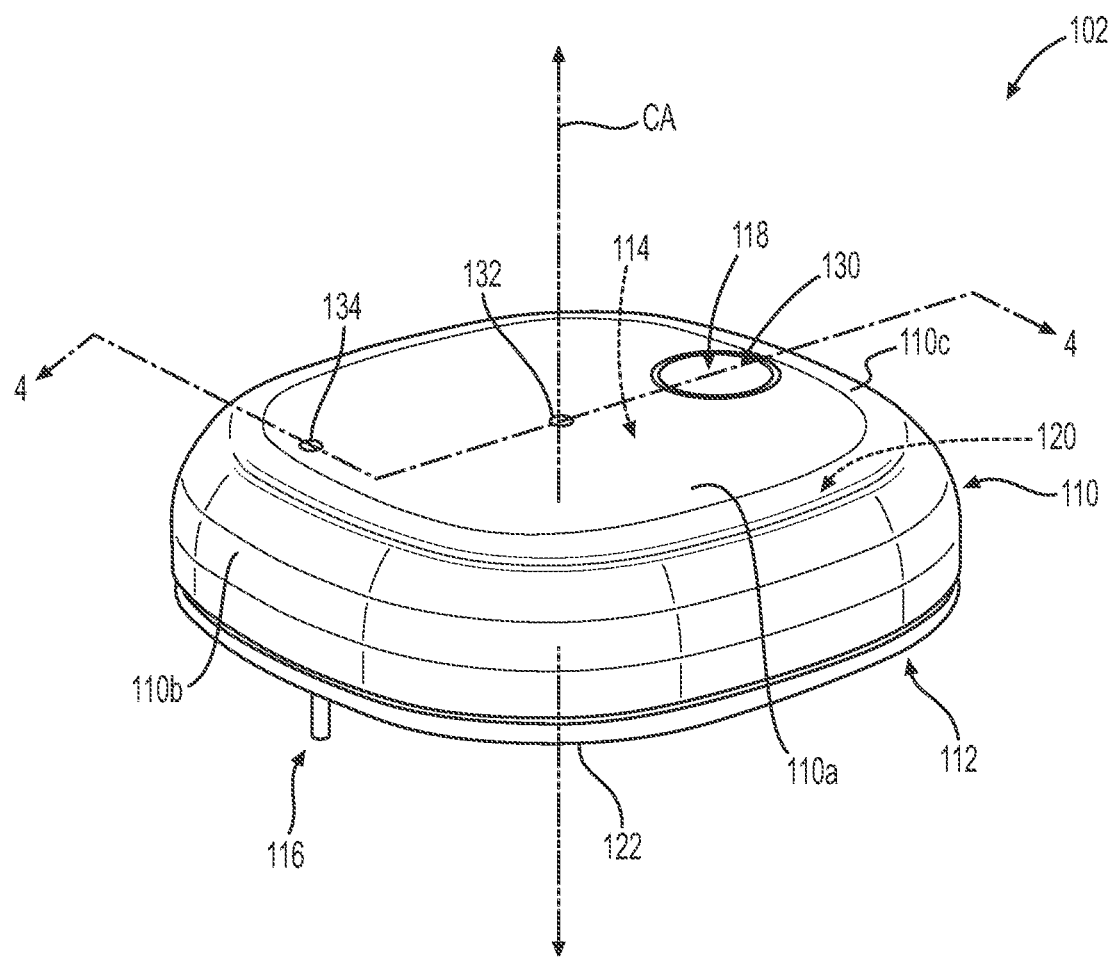
FIG. 2 is a perspective view of the wearable infusion port of FIG. 1.
Figure 3:
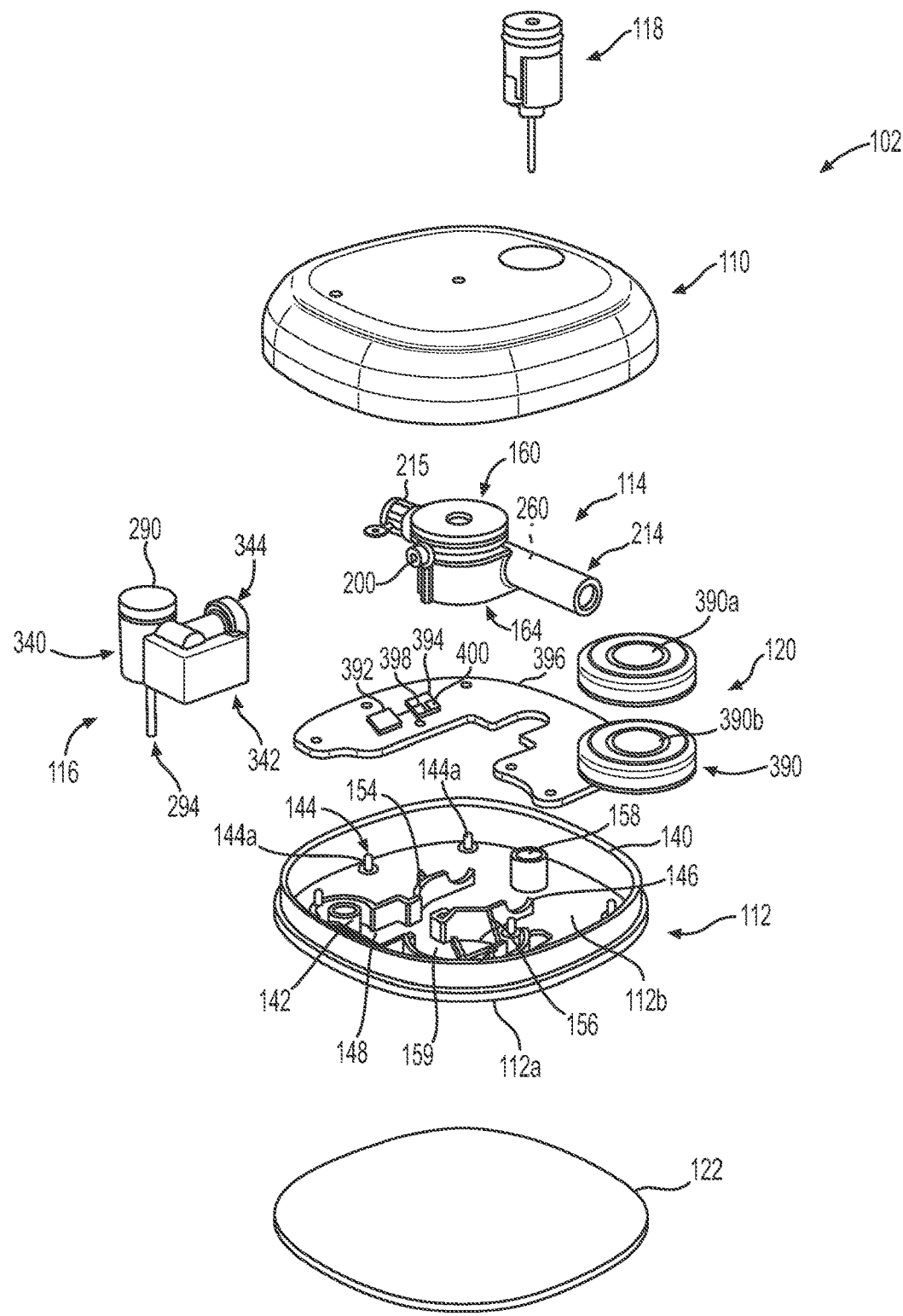
FIG. 3 is a partially exploded view of the wearable infusion port of FIG. 1.

With reference to FIG. 1, FIG. 1 is a perspective view of an infusion system 100. In one example, the infusion system 100 includes a wearable infusion port 102 and a pump 104. As will be discussed, the wearable infusion port 102 may be coupled directly to a user to deliver a treatment fluid, such as insulin, to the body of the user. The pump 104 may be coupled to the wearable infusion port 102 to supply the wearable infusion port 102 with the treatment fluid, such as insulin. With reference to FIGS. 2 and 3, the wearable infusion port 102 is shown. The wearable infusion port 102 is generally rectangular or square, however, it will be understood that the wearable infusion port 102 may have any desired shape. In one example, the wearable infusion port 102 includes an upper or first housing 110, a bottom or second housing 112, a valve assembly 114, a cannula assembly 116, a continuous glucose monitor assembly 118 and a control system 120. The wearable infusion port 102 may be coupled to the user via an adhesive patch 122.

Figure 4:
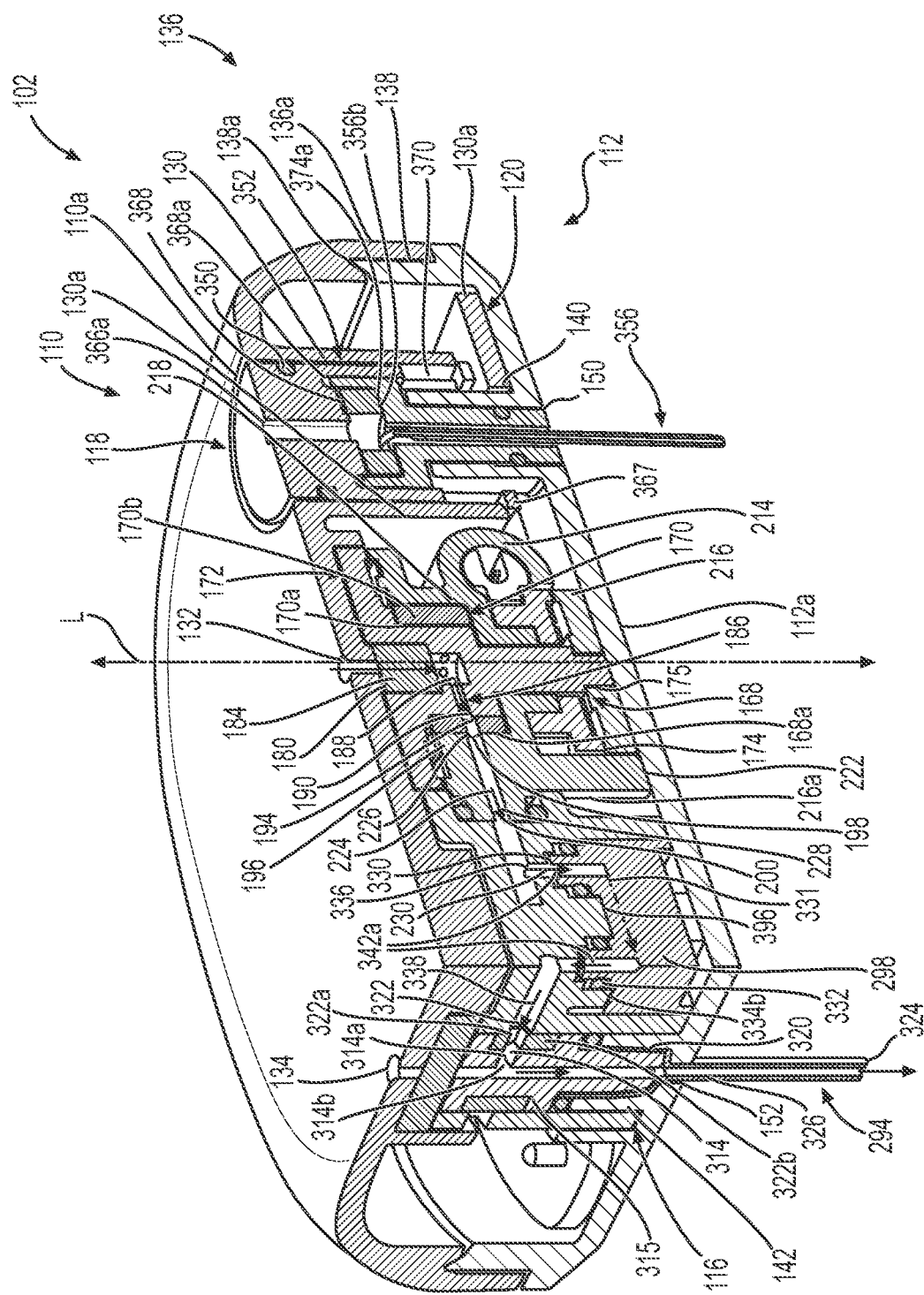
FIG. 4 is a cross-sectional view of the wearable infusion port of FIG. 1, taken along line 4-4 of FIG. 2.
Figure 4A:
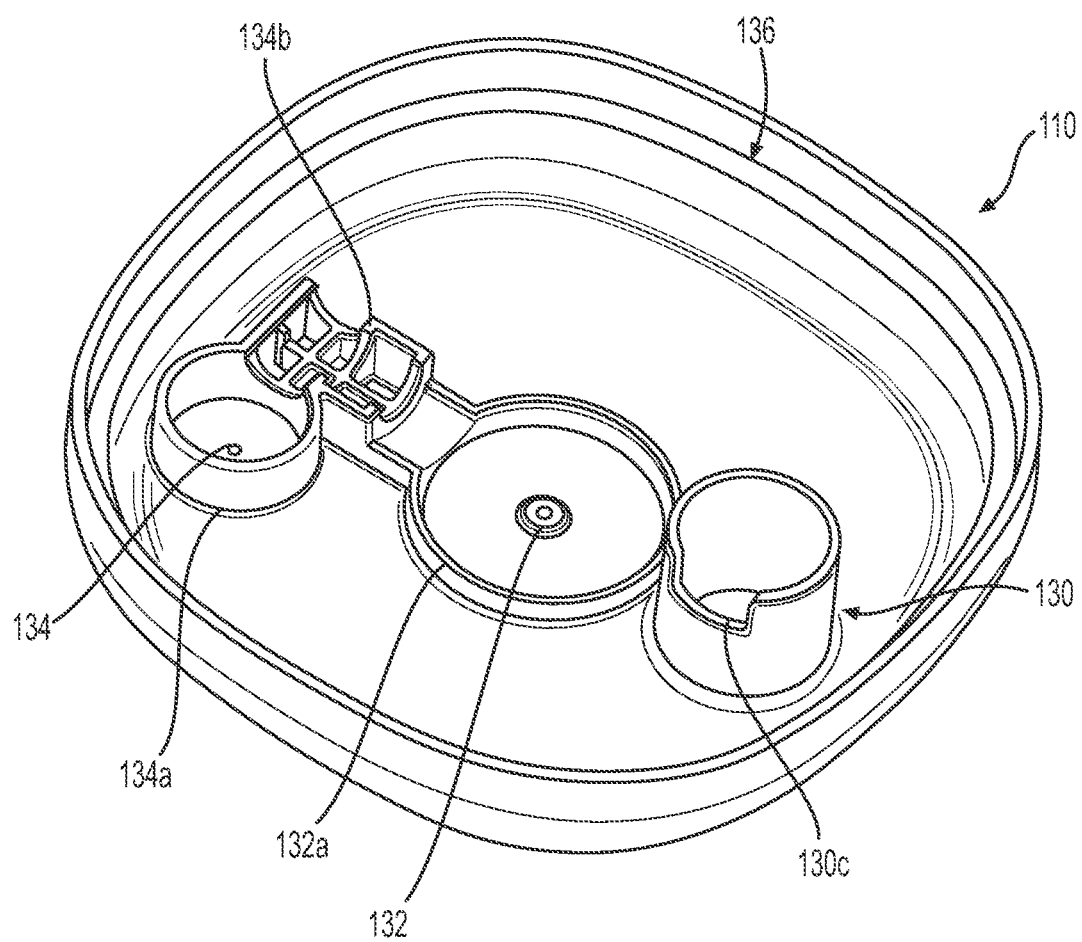
FIG. 4A is a bottom view of a first housing of the wearable infusion port of FIG. 1.

The first housing 110 and the second housing 112 may be composed of a suitable biocompatible material, including, but not limited to a biocompatible polymer-based material, which may be molded, printed, cast, etc. The first housing 110 and the second housing 112 are substantially rectangular or square, however, the first housing 110 and the second housing 112 may have any desired shape. The first housing 110 and the second housing 112 cooperate to substantially enclose the valve assembly 114, the cannula assembly 116, the continuous glucose monitor assembly 118 and the control system 120. With reference to FIGS. 4 and 4A, the first housing 110 defines a receiving projection 130, a first needle port 132, a second needle port 134 and a coupling interface 136.

The receiving projection 130 receives a portion of the continuous glucose monitor assembly 118 for coupling the continuous glucose monitor assembly 118 to the first housing 110. Generally, the receiving projection 130 extends inward, through a first surface 110a of the first housing 110, toward the second housing 112. The receiving projection 130 is shown as cylindrical (FIG. 4A), but may have any desired shape. With brief reference to FIG. 4A, the receiving projection 130 may include a cut-out 130c, which cooperates with the portion of the continuous glucose monitor assembly 118 to couple the continuous glucose monitor assembly 118 to the first housing 110. The cut-out 130c provides clearance for an electrical connection between the electrical contacts 380 and the circuit board 396. With reference back to FIG. 4, the first needle port 132 is defined through the first surface 110a of the first housing 110, and enables a needless syringe, infusion pen or other device, such as the pump 104, to dispense fluid into the wearable infusion port 102. The first needle port 132 is in fluid communication with the valve assembly 114 to provide the fluid received through the first needle port 132 to the valve assembly 114, as will be discussed. With brief reference to FIG. 4A, the first needle port 132 may be surrounded by a lip 132a defined on the first housing 110, which assists in coupling a portion of the valve assembly 114 to the first housing 110. With reference back to FIG. 4, the first needle port 132 defines an inlet for the wearable infusion port 102. The second needle port 134 is defined in the first surface 110a, and enables an insertion device, such as a needle or other device, to couple the cannula assembly 116 to the anatomy. Thus, the second needle port 134 is in communication with the cannula assembly 116 to enable a portion of the cannula assembly 116 to be coupled to the anatomy. Generally, the second needle port 134 is defined through the first surface 110a so as to be spaced a distance apart from the first needle port 132 and the receiving projection 130. In this example, with brief reference to FIG. 2, the second needle port 134 is defined adjacent to a first end 110b of the first housing 110, and the receiving projection 130 is defined adjacent to a second end 110c of the first housing 110, with the second end 110c opposite the first end 110b. The second needle port 134 is defined generally along a center axis CA of the wearable infusion port 102. By spacing the second needle port 134 from the receiving projection 130, the likelihood of insulin delivered by the cannula assembly 116 affecting the continuous glucose monitor assembly 118 is reduced. With brief reference to FIG. 4A, the second needle port 134 may include a cylindrical portion 134a defined about a perimeter of the second needle port 134. The cylindrical portion 134a assists with coupling the cannula assembly 116 to the first housing 110. The first housing 110 may also define a cannula guide portion 134b, which may cooperate with a portion of the cannula assembly 116 to assist in coupling the cannula assembly 116 to the first housing 110.

With reference back to FIG. 4, the coupling interface 136 is defined about a perimeter of the first housing 110. The coupling interface 136 defines a sidewall 136a, and includes an interlock recess 138. The sidewall 136a extends about the perimeter of the first housing 110, and extends from the first surface 110a generally so as to be substantially parallel to the center axis CA. The sidewall 136a cooperates with the second housing 112 to substantially enclose the valve assembly 114, the cannula assembly 116, the continuous glucose monitor assembly 118 and the control system 120. The interlock recess 138 is defined about a perimeter of the sidewall 136a, and in one example, is a relief having a triangular notch 138a. The triangular notch 138a interfaces with or interlocks with a corresponding feature on the second housing 112 to assist in coupling the first housing 110 to the second housing 112 with a waterproof seal. It should be understood, however, that the interlock recess 138 may not include the triangular notch 138a, but rather may define an endwall that is substantially perpendicular to the center axis CA (FIG. 2) or that a notch associated with the interlock recess 138 may have a different shape.

The second housing 112 is coupled to the first housing 110. With reference to FIG. 3, the second housing 112 includes a second receiving projection 140, a third receiving projection 142, a controller receiving portion 144, a valve receiving portion 146 and a cannula receiving portion 148. The second receiving projection 140 cooperates with the receiving projection 130 of the first housing 110 to receive the continuous glucose monitor assembly 118. In one example, with reference to FIG. 4, the second receiving projection 140 is cylindrical, and has a second diameter, which is different and, in this example, less than a diameter of the receiving projection 130. The second diameter is sized to guide a portion of the continuous glucose monitor assembly 118 into the anatomy. In addition, the reduced diameter of the second receiving projection 140 enables the second receiving projection 140 to be at least partially received within an opening 130a defined by the receiving projection 130. Thus, in this example, the second receiving projection 140 is received within the receiving projection 130 of the first housing 110, and the continuous glucose monitor assembly 118 is received within both of the second receiving projection 140 and the receiving projection 130. The second receiving projection 140 also defines a second bore 150. The second bore 150 is defined through the second housing 112. The second bore 150 enables a portion of the continuous glucose monitor assembly 118 to pass through the second housing 112 and into the anatomy when the wearable infusion port 102 is coupled to a user. In this example, the diameter of the second bore 150 is substantially the same as the diameter of the second receiving projection 140.

The third receiving projection 142 receives a portion of the cannula assembly 116. In this example, the third receiving projection 142 is cylindrical; however, the third receiving projection 142 may have any desired shape. The third receiving projection 142 also defines a third bore 152. The third bore 152 is defined through the second housing 112. The third bore 152 enables a portion of the cannula assembly 116 to pass through the second housing 112 and into the anatomy when the wearable infusion port 102 is coupled to a user. In this example, the diameter of the third bore 152 is different than, and in this example, smaller than the diameter of the third receiving projection 142.

With reference to FIG. 3, the controller receiving portion 144 is defined along a third surface 112b of the second housing 112, which is opposite a second surface 112a. In this example, the controller receiving portion 144 includes at least one or a pair of posts 144a, which cooperates to retain the control system 120 within the second housing 112. The valve receiving portion 146 includes a first rib 154 and a second rib 156. The first rib 154 and the second rib 156 may be integrally formed with the second housing 112, or may be coupled to the second housing 112. The first rib 154 and the second rib 156 cooperate to define a circular region 158, which retains a portion of the valve assembly 114. The cannula receiving portion 148 is also defined by the first rib 154 and the second rib 156. In one example, the first rib 154 and the second rib 156 also cooperate to define a substantially rectangular region 159, which retains a portion of the cannula assembly 116.

Figure 5:
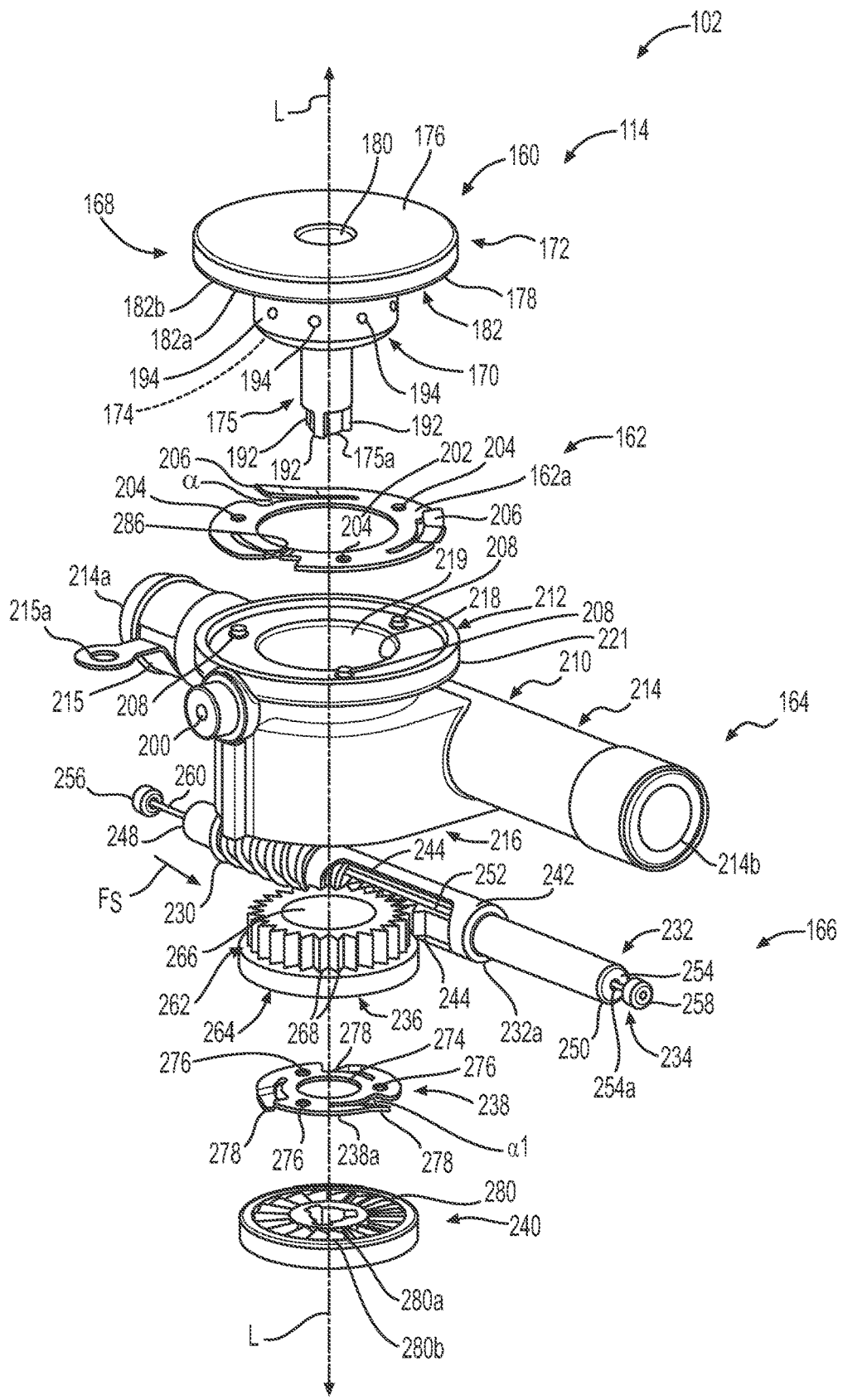
FIG. 5 is an exploded view of a valve assembly associated with the wearable infusion port of FIG. 1.
Figure 5A:
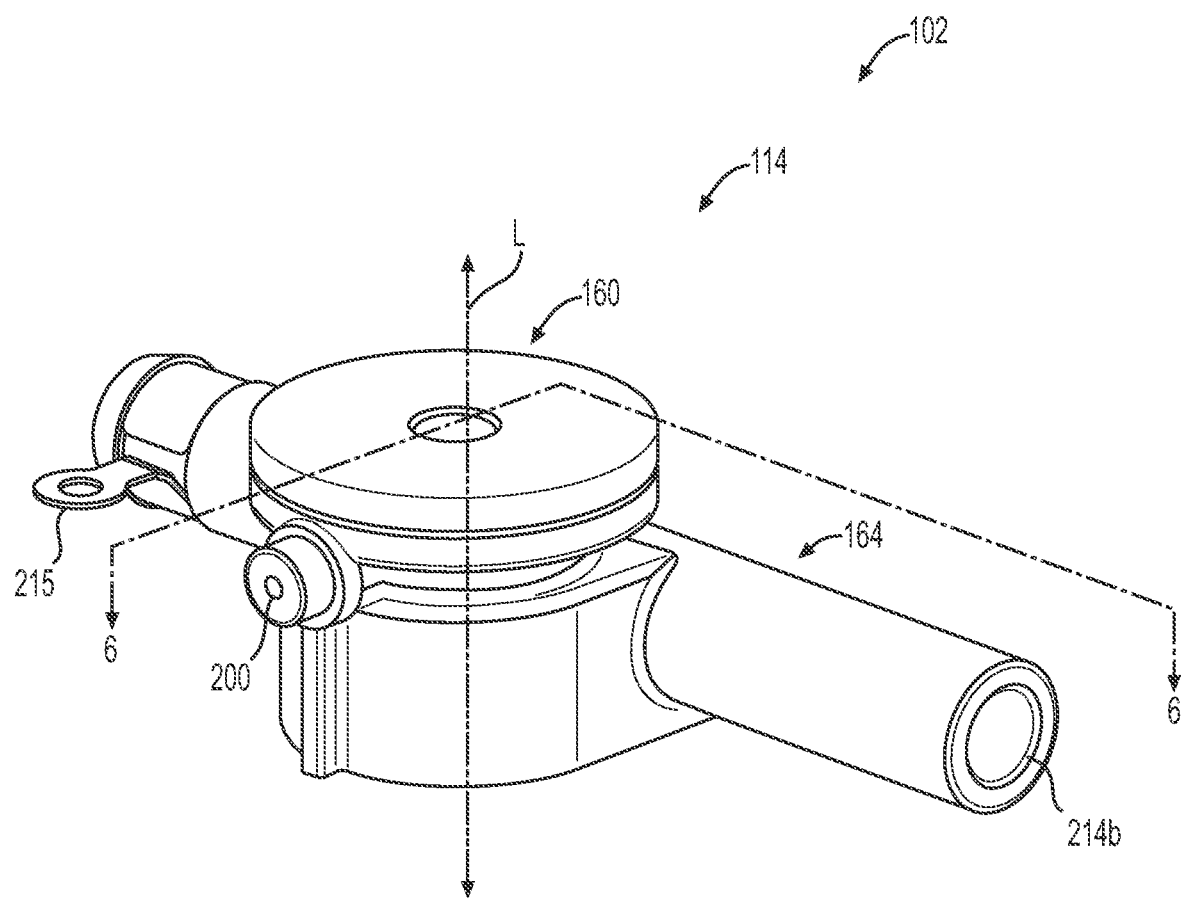
FIG. 5A is a perspective view of the valve assembly associated with the wearable infusion port of FIG. 1.

The valve assembly 114 receives the fluid for infusion, which is insulin in this example, and is movable between an opened state and a closed state. In the closed state, insulin is not dispensed and in the opened state, the insulin is dispensed. With reference to FIG. 5, an exploded view of the valve assembly 114 is shown. In one example, the valve assembly 114 includes a rotor 160, a ratchet shim 162, a stator 164 and an actuator assembly 166.

Figure 5B:
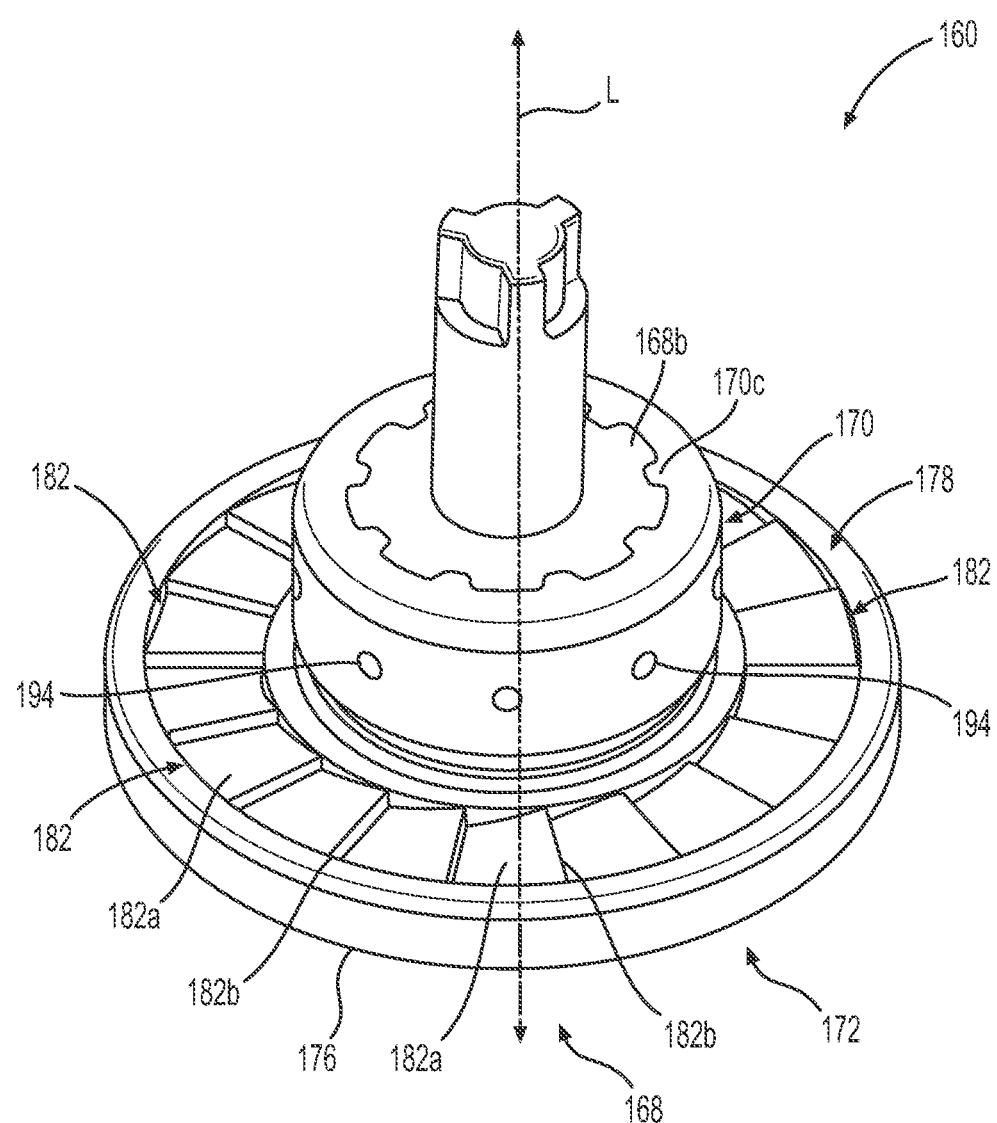
FIG. 5B is a rear perspective view of a rotor of the valve assembly of FIG. 5.

The rotor 160 includes a rotor body 168 and a conduit sleeve 170. The rotor body 168 defines a disc 172, a conduit portion 174 and a shaft 175. The rotor 160 may be composed of a suitable biocompatible material, such as a polymer-based material, metal or metal alloy, which is cast, molded, printed, stamped, etc. The rotor 160 may be integrally formed, or may compose separate components that are coupled together, via ultrasonic welding, for example. For example, the rotor body 168 and the conduit sleeve 170 may be discretely formed, and coupled together via ultrasonic welding. In one example, the rotor body 168 may include a plurality of teeth 168b, which cooperate with a respective plurality of mating teeth 170c defined on the conduit sleeve 170 to couple the conduit sleeve 170 to the rotor body 168 with a press-fit. The disc 172 is annular, and includes a first disc surface 176 and a second disc surface 178 opposite the first disc surface 176. A central bore 180 is defined through the disc 172 and extends to the conduit portion 174. The first disc surface 176 is substantially planar and smooth. With reference to FIG. 5B, the second disc surface 178 includes a plurality of angled notches 182, which are defined about a perimeter of the central bore 180. Each of the plurality of angled notches 182 includes a ramp surface 182a and a planar surface 182b. The ramp surface 182a cooperates with the ratchet shim 162 to enable the ratchet shim 162 to move in a direction, which in this example, is counterclockwise. The planar surface 182b is orientated along an axis that is substantially parallel to a longitudinal axis L of the valve assembly 114. The planar surface 182b cooperates with the ratchet shim 162 to inhibit the ratchet shim 162 from rotating clockwise. Thus, the planar surface 182b forms a stop, which inhibits the rotation of the ratchet shim 162, and thus, the stator 164, as will be discussed further herein.

With reference to FIG. 4, the central bore 180 is in fluid communication with the first needle port 132 to receive the fluid or insulin from the first needle port 132. In one example, the central bore 180 includes a septum 184, which serves to prevent the ingress and egress of fluids into/out of the rotor body 168. The septum 184 is pierceable by a piercing member of the syringe (not shown) to enable fluid flow from the syringe into the rotor body 168. Thus, the septum 184 is downstream from the first needle port 132. The central bore 180 extends from the disc 172 to the conduit portion 174 to provide the fluid, such as insulin, to the conduit portion 174.

The conduit portion 174 of the rotor body 168 is in fluid communication with the central bore 180 and is defined downstream of the septum 184. The conduit portion 174 is defined between the disc 172 and the shaft 175. In one example, the conduit portion 174 includes at least one or a plurality of rotor conduits 186, which are defined through the rotor body 168. In one example, the conduit portion 174 includes about 9 rotor conduits 186, which are spaced apart about a perimeter or circumference of the conduit portion 174. In this example, the rotor conduits 186 are spaced about 40 degrees apart from each other about the circumference of the conduit portion 174. Each of the rotor conduits 186 extend from the central bore 180 to an exterior surface 168a of the rotor body 168. Each of the rotor conduits 186 has an inlet 188 in fluid communication with the central bore 180 and an outlet 190 in fluid communication with the conduit sleeve 170. The rotor conduits 186 are generally defined to extend along an axis that is substantially transverse or parallel to the longitudinal axis L of the valve assembly 114, however, the rotor conduits 186 may have any desired orientation.

With reference back to FIG. 5, the shaft 175 is fixedly coupled to a portion of the actuator assembly 166. In one example, the shaft 175 includes at least one or a plurality of teeth 192, which extend outwardly from the shaft 175 at a terminal end 175a of the shaft 175. In one example, the shaft 175 includes three teeth 192, which cooperate with the portion of the actuator assembly 166 to enable the actuator assembly 166 to drive the rotor 160 via the shaft 175, as will be discussed herein.

The conduit sleeve 170 is non-rotatably coupled to the conduit portion 174 of the rotor body 168. The conduit sleeve 170 is substantially annular, and defines at least one or a plurality of conduits 194 through the conduit sleeve 170. In one example, the conduit sleeve 170 includes about 9 conduits 194, which are spaced apart about a perimeter or circumference of the conduit sleeve 170. In this example, the rotor conduits 186 are spaced about 40 degrees apart from each other about the circumference of the conduit sleeve 170. With reference to FIG. 4, each of the conduits 194 extend from an inner surface or diameter 170a of the conduit sleeve 170 to an exterior surface or diameter 170b of the conduit sleeve 170. Each of the conduits 194 has a conduit inlet 196, which is in fluid communication with the outlet 190 of a respective one of the rotor conduits 186; and a conduit outlet 198, which is in fluid communication with an outlet 200 of the stator 164 based on a state of the valve assembly 114. The conduits 194 are generally defined to extend along an axis that is substantially transverse or parallel to the longitudinal axis L of the valve assembly 114, however, the conduits 194 may have any desired orientation.

With reference back to FIG. 5, the ratchet shim 162 is coupled between the rotor 160 and the stator 164. In one example, the ratchet shim 162 is non-rotatably coupled to the stator 164, and inhibits a clockwise rotation of the rotor 160. It should be noted that while the rotation of the rotor 160 is described herein as being counterclockwise, the valve assembly 114 may be configured if desired to rotate in a clockwise direction. Generally, the rotor 160 rotates in a counterclockwise direction relative to the ratchet shim 162, and the ratchet shim 162 cooperates with the disc 172 of the rotor 160 to inhibit clockwise motion of the rotor 160. The ratchet shim 162 may be composed of a suitable biocompatible material, such as a polymer-based material, metal or metal alloy, which is cast, molded, printed, stamped, etc. In one example, the ratchet shim 162 is annular and includes a shim bore 202, at least one or a plurality of mounting bores 204 and at least one or a plurality of anti-rotation tabs 206.

The shim bore 202 is defined through the ratchet shim 162 along the longitudinal axis L of the valve assembly 114, and is sized to enable the ratchet shim 162 to be positioned about the conduit sleeve 170 of the rotor 160. The mounting bores 204 are defined through the ratchet shim 162 and are spaced apart about a perimeter of the shim bore 202. The mounting bores 204 cooperate with or receive a respective one of corresponding projections 208 that extend outwardly from the stator 164 to non-rotatably couple the ratchet shim 162 to the stator 164. It should be noted that other engaging features may be employed to non-rotatably couple the ratchet shim 162 to the stator 164. The anti-rotation tabs 206 are defined at a perimeter or outer circumference of the ratchet shim 162. In one example, the ratchet shim 162 includes three anti-rotation tabs 206, but the ratchet shim 162 may include any number of anti-rotation tabs 206. Each of the anti-rotation tabs 206 is cantilevered relative to the ratchet shim 162, and is inclined relative to a surface 162a of the ratchet shim 162. In this regard, each of the anti-rotation tabs 206 is inclined at a positive angle or upward to engage with the plurality of angled notches 182 of the disc 172. In one example, the anti-rotation tabs 206 are inclined by an angle α, which is about 15 to about 180 degrees. The angle α is sized to enable the anti-rotation tabs 206 to move along the ramp surface 184a (FIG. 5B) of the disc 172 as the rotor rotates in the counterclockwise direction, but to contact the planar surface 184b (FIG. 5B) in the rotation of the rotor 160 in the clockwise direction. The contact between the anti-rotation tabs 206 and the planar surfaces 184b inhibits the rotation of the rotor 160 in the clockwise direction.

The stator 164 is coupled to the ratchet shim 162, and to the rotor 160. The stator 164 is coupled to the rotor 160 to enable the rotor to move relative to the stator 164. The stator 164 may be composed of a suitable biocompatible material, such as a polymer-based material, metal or metal alloy, which is cast, molded, printed, stamped, etc. The stator 164 includes a body 210 that defines a ratchet flange 212, an actuator shaft receiving portion 214, an actuator receiving portion 216, a conduit receiving portion 218 and the outlet 200. The stator 164 also defines a central stator bore 219. The central stator bore 219 is defined along the longitudinal axis L of the valve assembly 114, and is sized to receive the rotor 160 within the stator 164. Generally, the central stator bore 219 is sized and shaped to receive the conduit sleeve 170, the conduit portion 174 and the shaft 175 of the rotor 160, while the disc 172 is positioned external to the stator 164 for engagement with the ratchet shim 162.

Figure 5D:
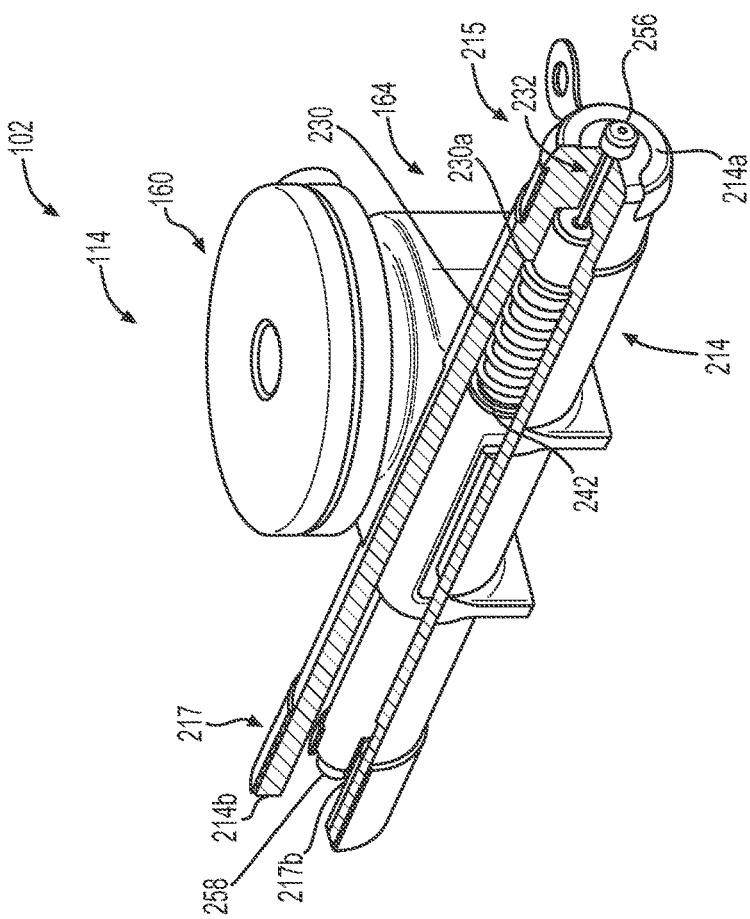
FIG. 5D is a cross-sectional view of the valve assembly, taken along line 5D-5D of FIG. 5C.
Figure 5C:
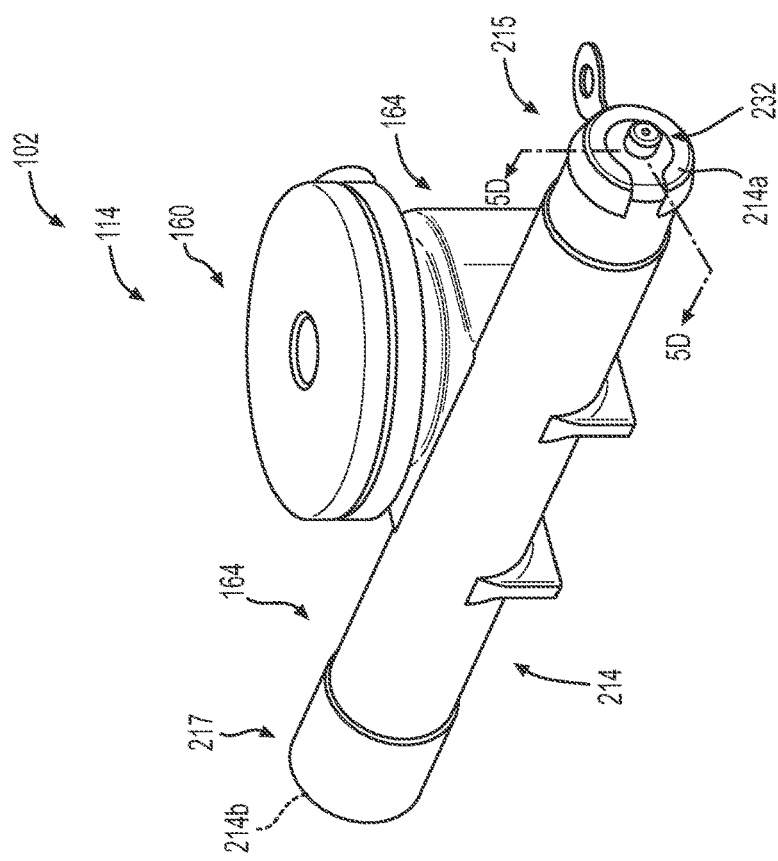
FIG. 5C is a side perspective view of the valve assembly associated with the wearable infusion port of FIG. 1.

The ratchet flange 212 is defined on the body 210 opposite the actuator receiving portion 216. The ratchet flange 212 is circular, and includes the projections 208. The ratchet flange 212 may include a lip 221, which is defined about a perimeter of the ratchet flange 212 to further assist in retaining the ratchet shim 162 within the ratchet flange 212. The actuator shaft receiving portion 214 receives a portion of the actuator assembly 166. In one example, the actuator shaft receiving portion 214 is substantially cylindrical, with open opposed ends 214a, 214b. The actuator shaft receiving portion 214 extends along an axis, which is substantially transverse or perpendicular to the longitudinal axis L of the valve assembly 114. The actuator shaft receiving portion 214 may also include a flange 215. With reference to FIGS. 5C and 5D, the flange 215 may extend about a perimeter of the actuator shaft receiving portion 214 proximate the end 214a, and may include a bore 215a. The bore 215a may receive a mechanical fastener, such as a screw, pin, post, etc. to couple the actuator shaft receiving portion 214 to the control system 120. Generally, the flange 215 is composed of a conductive material, and the control system 120 is configured to supply a current to the flange 215. The current received by the flange 215 is transferred to the actuator shaft 232 to move the valve assembly 114 from the closed state to the opened state. In one example, the flange 215 includes a coupling portion 215b, which receives an actuator wire 234 of the actuator shaft 232. The coupling portion 215b is electrically and physically coupled to the actuator wire 234 to transfer the current received from the control system 120 to the actuator wire 234 via the flange 215. In addition, the actuator shaft receiving portion 214 may also include a second flange 217. The second flange 217 may extend about a perimeter of the actuator shaft receiving portion 214 proximate the end 214b and is physically and electrically coupled to the actuator wire 234. Generally, the second flange 217 is composed of a conductive material, and the control system 120 is configured to receive a current from the second flange 217 such that current flows through the actuator wire 234 from the flange 215 to the second flange 217. The current received by the second flange 217 is returned to the control system 120. In one example, the second flange 217 includes a second coupling portion 217b, which receives a portion of the actuator wire 234. The second coupling portion 217b is electrically and physically coupled to the actuator wire 234 to transfer the current received through the actuator wire 234 to the control system 120.

With reference to FIG. 4, the actuator shaft receiving portion 214 is in communication with the actuator receiving portion 216. The actuator receiving portion 216 is substantially cylindrical, and is sized to receive a portion of the cannula assembly 116. The actuator receiving portion 216 may also define a guide 222 on an external surface 216a. The guide 222 cooperates with a portion of the cannula assembly 116 to ensure the proper assembly of the valve assembly 114 to the cannula assembly 116.

With reference back to FIG. 5, the conduit receiving portion 218 is defined within the body 210 between the ratchet flange 212 and the actuator receiving portion 216.

The conduit receiving portion 218 is sized to surround the conduit sleeve 170 of the rotor 160 when the rotor 160 is coupled to the stator 164. With reference to FIG. 4, the conduit receiving portion 218 also includes an outlet conduit 224. The outlet conduit 224 is fluidly coupled to one of the conduits 194 of the conduit sleeve 170 based on the state of the valve assembly 114, and is fluidly coupled to the outlet 200. The outlet conduit 224 includes an outlet conduit inlet 226 that is fluidly coupled to one of the conduits 194 based on the state of the valve assembly 114; and an outlet conduit outlet 228 that is fluidly coupled to the outlet 200. The outlet conduit 224 is generally defined to extend along an axis that is substantially transverse or parallel to the longitudinal axis L of the valve assembly 114, however, the outlet conduit 224 may have any desired orientation. The outlet 200 is fluidly coupled to the cannula assembly 116. Thus, the outlet conduit 224 directs the fluid or insulin received from the conduit sleeve 170 of the rotor 160 to the cannula assembly 116.

The actuator assembly 166 is responsive to one or more control signals from the control system 120 to move the rotor 160. As will be discussed, the rotation of the rotor 160 moves the valve assembly 114 between the opened state and the closed state. The actuator assembly 166 includes a biasing member or spring 230, an actuator shaft 232, an actuator wire 234, an actuator pinion 236, an actuator shim 238 and an end plate 240.

The spring 230 is a coil spring. The spring 230 is composed of a spring steel, and may be extruded and wound to form the spring 230. The spring 230 is coupled to an exterior surface 232a of the actuator shaft 232, and applies a spring force Fs against a collar 242 of the actuator shaft 232 to bias the actuator shaft 232 into a first position and sits against a spring seat 230a defined in the actuator shaft receiving portion 214 (FIG. 5D). When the actuator shaft 232 is in the first position, the valve assembly 114 is in the closed state. As will be discussed, the actuator shaft 232 is movable to a second position, in which the valve assembly 114 is in the opened state.

Figure 5E:
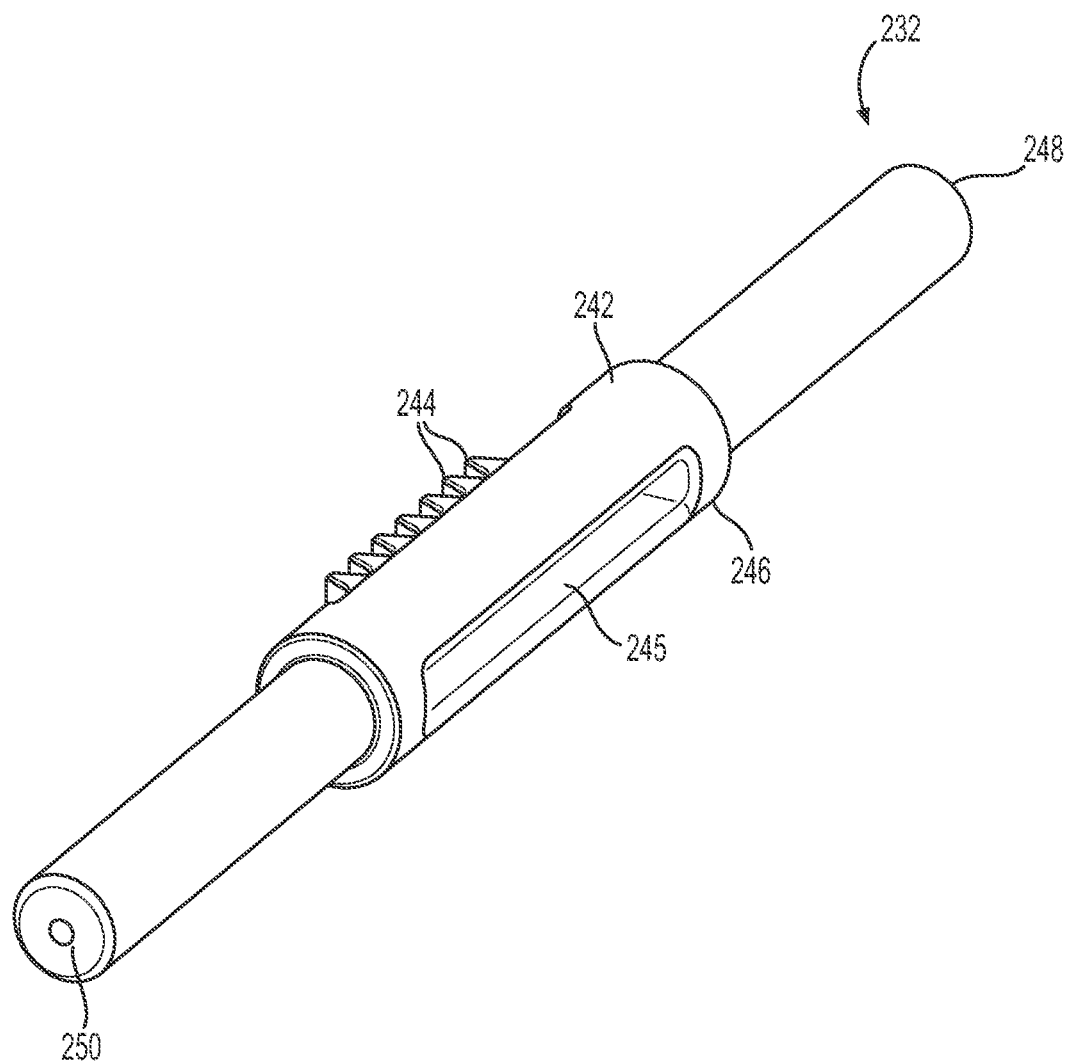
FIG. 5E is a bottom perspective view of an actuator shaft associated with the valve assembly.

The actuator shaft 232 is cylindrical, and is received within the actuator shaft receiving portion 214 of the stator 164. The actuator shaft 232 may be composed of a suitable biocompatible material, such as a polymer-based material, metal or metal alloy, which is cast, molded, printed, stamped, etc. The actuator shaft 232 includes the collar 242, at least one or a plurality of shaft teeth 244, a wire receiving channel 246 and opposed ends 248, 250. The collar 242 is defined about the exterior surface 232a of the actuator shaft 232. The collar 242 is defined to extend about only a portion of the exterior surface 232a, such that the opposed ends 248, 250 of the actuator shaft 232 have a diameter, which is different, and less than, a diameter of the collar 242. The collar 242 includes a recess 252 defined along one side of the actuator shaft 232. The shaft teeth 244 are defined within the collar 242. The shaft teeth 244 form a rack, which engages with the actuator pinion 236. With reference to FIG. 5E, the actuator shaft 232 define a slot 245 opposite the shaft teeth 244 to assist in the manufacturing of the shaft teeth 244.

With reference back to FIG. 5, the wire receiving channel 246 is defined by an inner circumference of the actuator shaft 232. The wire receiving channel 246 extends between the opposed ends 248, 250. The wire receiving channel 246 is sized to receive the actuator wire 234. The opposed ends 248, 250 cooperate with the actuator wire 234. In one example, the opposed end 248 is circumferentially open to enable the actuator wire 234 to extend through the opposed end 248. The opposed end 250 includes a flange 254, which circumferentially closes the opposed end 250. The flange 254 is recessed within the opposed end 250, and provides a stop for a portion of the actuator wire 234. The flange 254 also defines a throughbore 254a, which enables a portion of the actuator wire 234 to pass through the flange 254.

The actuator wire 234 extends through the actuator shaft 232. The actuator wire 234 includes a first post 256, a second post 258 opposite the first post 256 and a wire 260. The first post 256 and the second post 258 are generally cylindrical, and have a diameter that is greater than a diameter of the wire 260. The first post 256 and the second post 258 may be composed of a suitable conductive material, such as a metal or metal alloy, which is cast, molded, printed, stamped, etc. The first post 256 and the second post 258 may be coupled to the wire 260 via press-fit, ultrasonic welding, etc. With reference to FIG. 5D, the first post 256 is coupled to the end 214a of the actuator shaft receiving portion 214 of the stator 164. The second post 258 extends beyond the actuator shaft 232 and is physically and electrically coupled to the second flange 217 and is movable to contact the flange 254 (FIG. 5). The first post 256 is physically and electrically coupled to the flange 215 to receive the current from the control system 120, which is conducted through the wire 260 to the second flange 217. The second post 258 contacts the flange 254 during a second, contracted state of the wire 260 to translate the actuator shaft 232, as will be discussed.

The wire 260 is a shape memory wire, and in one example, is a nitinol wire. Opposed ends of the wire 260 are coupled to a respective one of the first post 256 and the second post 258. In this example, the control system 120 supplies the current to the flange 215, which is received by the wire 260 via the first post 256 and is conducted by the wire 260 to the second flange 217, which conducts the current back to the control system 120. The current conducted by the wire 260 causes the wire to increase in temperature. The increase in temperature of the wire 260 causes the wire 260 to move from a first, extended state to a second, contracted state. In the first, extended state, the wire 260 is elongated within the wire receiving channel 246 as shown in FIG. 5, and the force Fs of the spring 230 maintains the actuator shaft 232 in the first position. In the second, contracted state, the wire 260 contracts, which pulls the second post 258 into contact with the flange 254. The continued contraction of the wire 260 along with the contact between the second post 258 and the flange 254 causes the actuator shaft 232 to translate within the actuator shaft receiving portion 214, which in turn, causes the shaft teeth 244 to rotate the actuator pinion 236. The rotation of the actuator pinion 236 drives the rotor 160 to dispense the fluid or insulin, as will be discussed.

Figure 6:
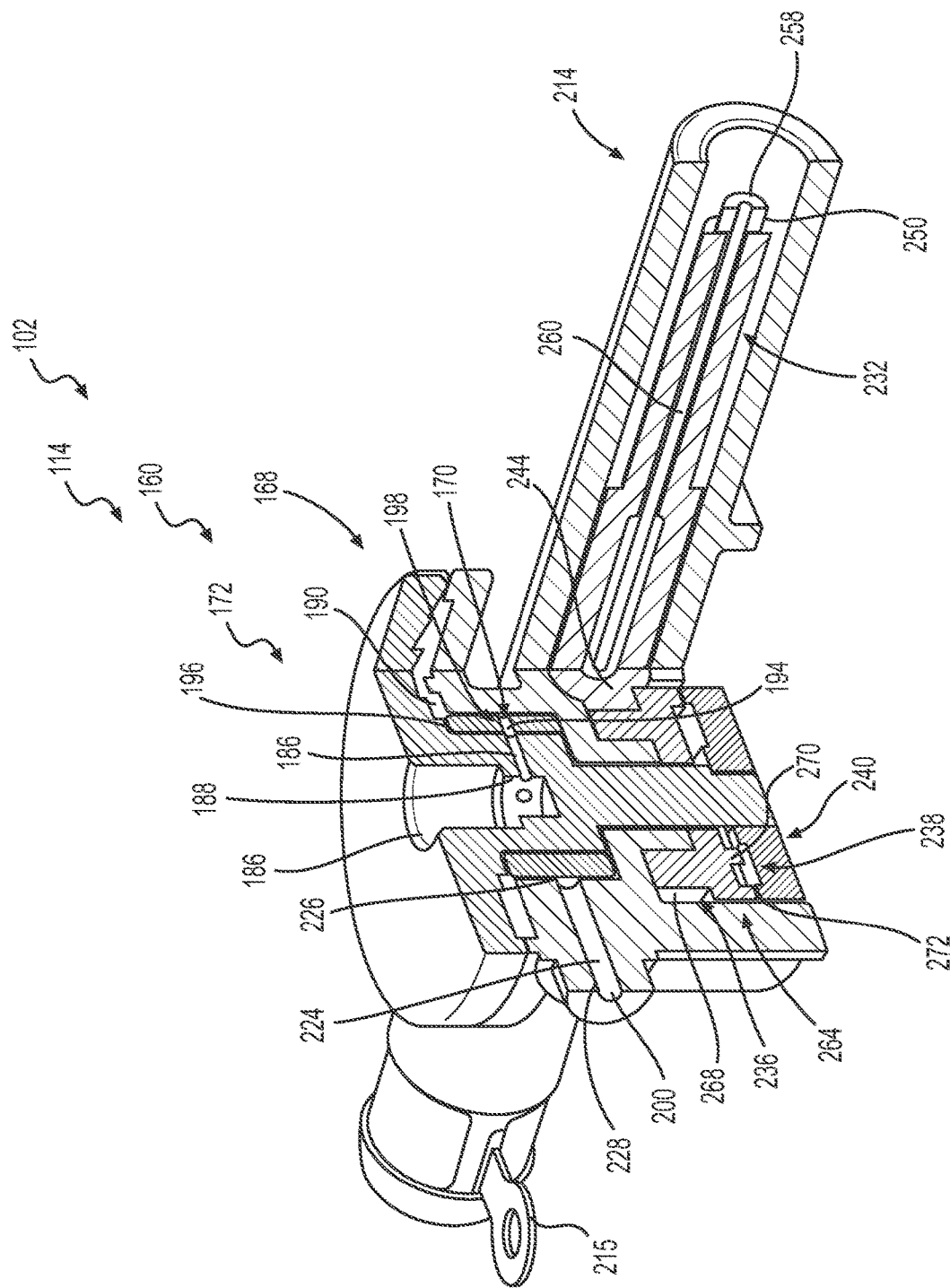
FIG. 6 is a cross-sectional view of the valve assembly, taken along line 6-6 of FIG. 5A, which illustrates the valve assembly in a closed state in accordance with various embodiments.

The actuator pinion 236 is annular; and has a first side 262 opposite a second side 264 and a central pinion bore 266. The actuator pinion 236 may be composed of a suitable biocompatible material, such as a polymer-based material, metal or metal alloy, which is cast, molded, printed, stamped, etc. The first side 262 defines at least one or a plurality of pinion teeth 268. The pinion teeth 268 are defined about a perimeter or circumference of the central pinion bore 266. The pinion teeth 268 matingly engage with the shaft teeth 244 such that a linear or translational movement of the actuator shaft 232 causes a rotation of the actuator pinion 236. The second side 264 of the actuator pinion 236 receives and retains the actuator shim 238. The second side 264 includes at least one or a plurality of projections 270 (FIG. 6). The second side 264 may also include a lip 272 (FIG. 6), which is defined about a perimeter of the second side 264 to further assist in retaining the actuator shim 238 within the second side 264 of the actuator pinion 236. The central pinion bore 266 is coupled to the shaft 175 of the rotor 160. In one example, the shaft 175 is coupled to the central pinion bore 266 via ultrasonic welding, however, other techniques may be employed to couple the actuator pinion 236 to the shaft 175. With the rotor 160 coupled to the actuator pinion 236, the rotation of the actuator pinion 236 via the actuator shaft 232 rotates the rotor 160 in the counterclockwise direction.

With reference to FIG. 5, the actuator shim 238 is coupled between the actuator pinion 236 and the end plate 240. In one example, the actuator shim 238 is non-rotatably coupled to the actuator pinion 236, and inhibits a clockwise rotation of the rotor 160. It should be noted that while the rotation of the rotor 160 is described herein as being counterclockwise, the rotor 160 of the valve assembly 114 may be configured if desired to rotate in a clockwise direction. Generally, the actuator pinion 236 rotates relative to the actuator shim 238, and the actuator shim 238 cooperates with the end plate 240 to inhibit clockwise motion of the rotor 160. The actuator shim 238 may be composed of a suitable biocompatible material, such as a polymer-based material, metal or metal alloy, which is cast, molded, printed, stamped, etc. In one example, the actuator shim 238 is annular and includes an actuator shim bore 274, at least one or a plurality of mounting bores 276 and at least one or a plurality of anti-rotation tabs 278.

The actuator shim bore 274 is defined through the actuator shim 238 along the longitudinal axis L of the valve assembly 114, and is sized to enable the actuator shim 238 to be positioned about the shaft 175 of the rotor 160. The mounting bores 276 are defined through the actuator shim 238 and are spaced apart about a perimeter of the actuator shim bore 274. The mounting bores 276 cooperate with or receive a respective one of the projections 270 (FIG. 6) that extend outwardly from the second side 264 of the actuator pinion 236 to non-rotatably couple the actuator shim 238 to the actuator pinion 236. This ensures that the actuator shim 238 rotates with the actuator pinion 236. It should be noted that other engaging features may be employed to non-rotatably couple the actuator shim 238 to the actuator pinion 236. The anti-rotation tabs 278 are defined at a perimeter or outer circumference of the actuator shim 238. In one example, the actuator shim 238 includes three anti-rotation tabs 278, but the actuator shim 238 may include any number of anti-rotation tabs 278. Each of the anti-rotation tabs 278 is cantilevered relative to the actuator shim 238, and is inclined relative to a surface 238a of the actuator shim 238. In this regard, each of the anti-rotation tabs 278 is inclined at a negative angle or downward to engage with a plurality of angled notches 280 of the end plate 240. In one example, the anti-rotation tabs 278 are inclined by an angle $\alpha_1$, which is about 15 to about 180 degrees. The angle $\alpha_1$ is sized to enable the anti-rotation tabs 278 to move along a ramp surface 280a of the end plate 240 as the end plate 240 rotates in the counterclockwise direction, but to contact a planar surface 280b in the rotation of the end plate 240 in the clockwise direction. The contact between the anti-rotation tabs 278 and the planar surfaces 280b of the end plate 240 drives the rotor 160 counterclockwise and inhibits the rotation of the rotor 160 in the clockwise direction.

The end plate 240 includes a first plate side 282 opposite a second plate side 284 and a central plate bore 286. The end plate 240 may be composed of a suitable biocompatible material, such as a polymer-based material, metal or metal alloy, which is cast, molded, printed, stamped, etc. The first plate side 282 includes the plurality of angled notches 280, which are defined about a perimeter of the central plate bore 286. Each of the plurality of angled notches 280 includes the ramp surface 280a and the planar surface 280b. The ramp surface 280a cooperates with the actuator shim 238 to enable the end plate 240 to move in a direction, which in this example, is counterclockwise. The planar surface 280b is orientated along an axis that is substantially parallel to the longitudinal axis L of the valve assembly 114. The planar surface 280b cooperates with the actuator shim 238 to inhibit the end plate 240 from rotating clockwise. Thus, the planar surface 280b forms a stop, which inhibits the rotation of the end plate 240, and thus, the rotor 160. The second plate side 284 is substantially planar or smooth (FIG. 4). The second plate side 284 is coupled to the third surface 112b of the second housing 112. The central plate bore 286 is defined through the end plate 240 along the longitudinal axis L. The central plate bore 286 includes a plurality of slots 286a, which extend radially outward from the central plate bore 286. Each of the slots 286a is sized and shaped to receive a corresponding one of the teeth 192 of the shaft 175. The engagement of the teeth 192 with the respective slots 286a rigidly couples the rotor 160 to the end plate 240.

Figure 7:
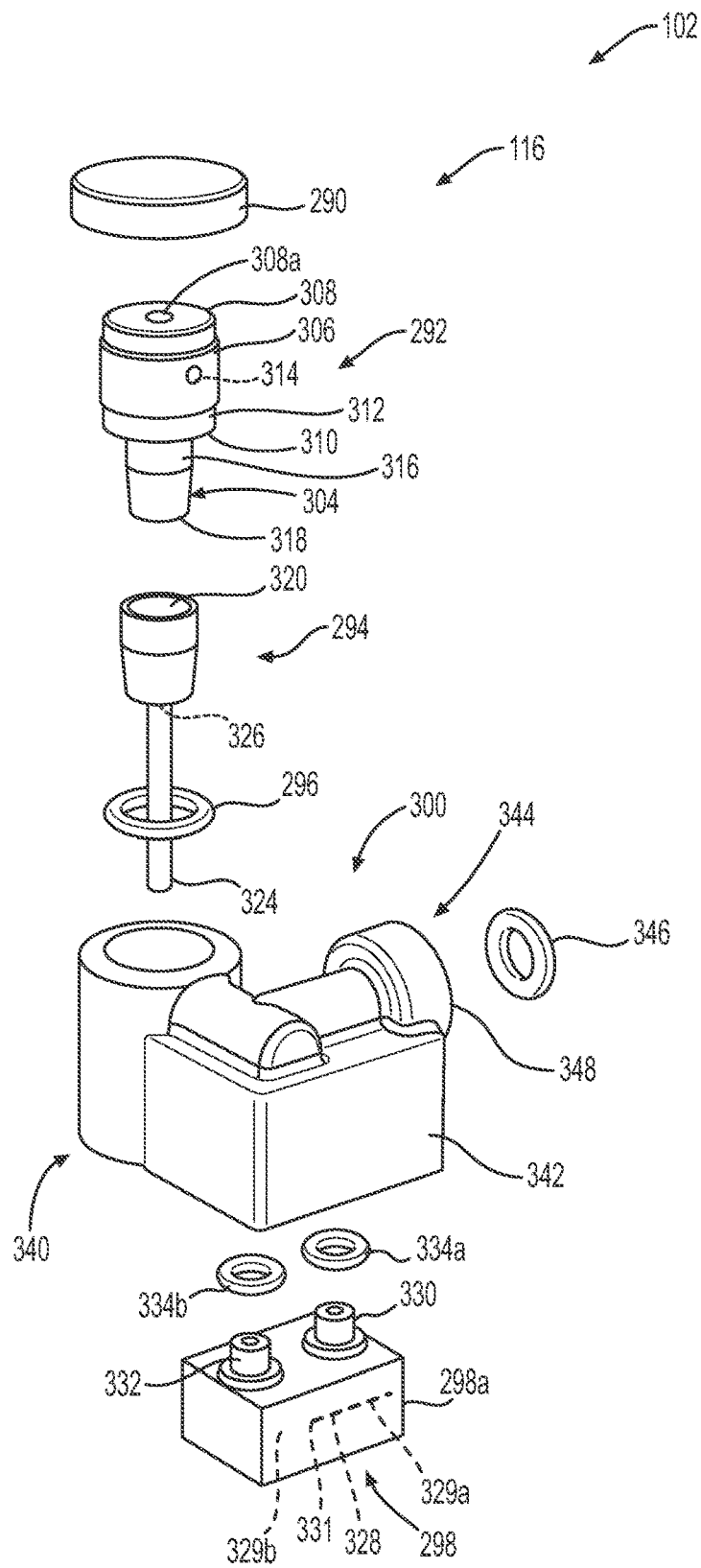
FIG. 7 is an exploded view of a cannula assembly associated with the wearable infusion port of FIG. 1.

With reference to FIG. 7, the cannula assembly 116 is fluidly coupled to the outlet 200 of the valve assembly 114 to receive the fluid or insulin. The cannula assembly 116 receives the fluid or insulin from the valve assembly 114 and meters the delivery of the fluid to the user. In one example, the cannula assembly 116 includes a needle septum 290, a cannula plug 292, a cannula 294, a cannula sealing member 296, a flow sensor 298 and a flow sensor housing 300. With brief reference to FIG. 4, the needle septum 290 is positioned between the second needle port 134 and the cannula plug 292. Thus, the needle septum 290 is downstream from the second needle port 134. The needle septum 290 serves to prevent the ingress and egress of fluids out of the cannula plug 292. The needle septum 290 is pierceable by a piercing member of the insertion device (not shown) to couple the cannula 294 to the user.

The cannula plug 292 is positioned between the needle septum 290 and the cannula 294. The cannula plug 292 couples the cannula 294 to the flow sensor housing 300. The cannula plug 292 may be composed of a suitable biocompatible material, such as a polymer-based material, metal or metal alloy, which is cast, molded, printed, stamped, etc. In one example, the cannula plug 292 includes a first plug portion 302, a second plug portion 304 and a sealing band 306. The first plug portion 302 has a first end 308 opposite a second end 310, and has a sidewall 312 that interconnects the first end 308 with the second end 310. The first plug portion 302 is substantially cylindrical and hollow. The first end 308 defines a first end bore 308a, which is sized to receive a needle associated with the insertion device for coupling the cannula 294 to the user. The second end 310 is coupled to the second plug portion 304. The second end 310 is also received within the flow sensor housing 300 such that the second end 310 compresses the cannula sealing member 296 to form a seal between the cannula plug 292 and the flow sensor housing 300. With reference to FIG. 4, the sidewall 312 defines a conduit 314 and a groove 315. The conduit 314 is fluidly coupled to the outlet 200 of the valve assembly 114 to receive the fluid or insulin, and is fluidly coupled to the cannula 294 to provide the cannula 294 with the fluid or insulin. In this example, the conduit 314 includes an inlet 314a fluidly coupled to the sealing band 306, and an outlet 314b fluidly coupled to the hollow interior of the first plug portion 302.

With reference to FIG. 7, the second plug portion 304 is coupled to or integrally formed with the first plug portion 302. The second plug portion 304 includes a cylindrical section 316 and a tapered section 318. The cylindrical section 316 is hollow, and is fluidly coupled to the first plug portion 302. The tapered section 318 is fluidly coupled to the cylindrical section 316, and is hollow. The tapered section 318 is circumferentially open to enable the fluid received by the inlet 314a of the first plug portion 302 to flow into the cannula 294 (FIG. 4). It should be noted that the shape of the second plug portion 304 with the cylindrical section 316 and the tapered section 318 is merely exemplary, as the second plug portion 304 may have any desired shape to mate with the cannula 294. In this regard, generally, the second plug portion 304 is received within a proximal end 320 of the cannula 294 to couple the cannula 294 to the cannula plug 292. In one example, the second plug portion 304 forms a press-fit with the proximal end 320, however, other techniques may be employed.

The sealing band 306 is coupled about the first plug portion 302. The sealing band 306 may be integrally or discretely formed with the first plug portion 302. In one example, the sealing band 306 is coupled to the first plug portion 302 to form a press-fit with the flow sensor housing 300 (FIG. 4). Generally, the sealing band 306 has a diameter that is different than, and in this example, greater than a diameter of the first plug portion 302 such that the sealing band 306 extends outwardly from the first plug portion 302 to form an interference fit or press-fit with the flow sensor housing 300. With brief reference to FIG. 4, the sealing band 306 includes a band conduit 322, which is in fluid communication with the outlet 200 and the cannula 294. In this regard, the band conduit 322 includes a band inlet 322a fluidly coupled to the flow sensor housing 300; and a band outlet 322b fluidly coupled to the conduit 314.

The cannula 294 is coupled to the cannula plug 292, and is configured to be inserted into the subcutaneous tissue of a user via the insertion device (not shown). The cannula 294 is a hollow tubular structure, and includes the proximal end 320 and a distal end 324. With reference back to FIG. 7, the proximal end 320 is configured and shaped to cooperate with the second plug portion 304 to couple the cannula 294 to the cannula plug 292. In this example, the proximal end 320 includes a cylindrical section 320a and a tapered section 320b. The cylindrical section 320a is sized to surround the cylindrical section 316 of the cannula plug 292, and the tapered section 320b is sized to surround the tapered section 318 of the cannula plug 292. The proximal end 320 also defines a cannula inlet 326 (FIG. 4). The cannula inlet 326 is fluidly coupled to the cannula plug 292 to receive the fluid or insulin from the flow sensor housing 300, and thus, the outlet 200 of the valve assembly 114, as will be discussed. The distal end 324 may be blunt or pointed, and is configured to be inserted into the subcutaneous tissue of the user when the wearable infusion port 102 is coupled to the user.

The cannula sealing member 296 is compressed by the cannula plug 292 to create a seal between the cannula 294 and the flow sensor housing 300. In one example, the cannula sealing member 296 is an elastomeric O-ring, however, other sealing mechanisms may be employed. The cannula sealing member 296 is sized to be positioned within the flow sensor housing 300 and between the second end 310 of the first plug portion 302 and the third receiving projection 142 of the second housing 112 (FIG. 4).

The flow sensor 298 is received within the flow sensor housing 300. The flow sensor 298 is in fluid communication with the cannula plug 292 and the outlet 200. The flow sensor 298 observes an amount of fluid that passes through the flow sensor housing 300 from the outlet 200, and generates one or more signals based on the observation. The flow sensor 298 is in communication with the control system 120 to provide the control system 120 with the sensor signals. In one example, the flow sensor 298 observes a volume of the insulin that passes through the flow sensor housing 300 to the cannula plug 292, through the cannula plug 292 to the cannula 294 and into the user. Thus, the flow sensor 298 observes a volume of the fluid or insulin that is dispensed by the valve assembly 114. As will be discussed, based on the signals received from the flow sensor 298, the control system 120 may output one or more control signals to the valve assembly 114 to move the valve assembly 114 from the opened state to the closed state.

In one example, the flow sensor 298 is a thermal mass flow sensor, which detects flow rates from about 1.0 to about 40.0 milliliters per minute (mL/min). In this example, the flow sensor 298 includes a heat source or heater 328 and a pair of temperature sensors 329a, 329b on either side of the heater. The heater 328 and the temperature sensors 329a, 329b are coupled to or in communication with a flow conduit 331 defined within the flow sensor 298 (FIG. 4). The heater 328 heats the fluid or insulin as the fluid passes through the flow sensor 298. One of the temperature sensors observe a first temperature of the fluid (prior to heating) and the other one of the temperature sensors observes a second temperature of the fluid (after heating). The signals from the temperature sensors 329a, 329b are communicated to the control system 120, and the control system 120 determines the volume of the fluid delivered based on a difference between the two temperature signals. The signals from the temperature sensors may be filtered, if desired, to account for turbulence. It should be noted, alternatively, the flow sensor 298 may also include a monitor module, which determines the volume based on the temperature signals, and transmits the determined volume to the control system 120.

In this example, with reference to FIG. 4, the flow sensor 298 includes a sensor inlet 330 in fluid communication with the outlet 200 and a sensor outlet 332 in fluid communication with the cannula plug 292. A pair of sealing members 334a, 334b may be coupled about a respective one of the sensor inlet 330 and the sensor outlet 332 to provide a seal between the flow sensor 298 and the flow sensor housing 300. In one example, the sealing members 334a, 334b are elastomeric O-rings, however, other sealing mechanisms may be employed. In this example, the flow sensor 298 includes a separate housing 298a, which includes the sensor inlet 330 and the sensor outlet 332, and also contains or encloses the temperature sensors 329a, 329a, the heater 328 and the flow conduit 331. It should be noted that the flow sensor 298 need not include a separate housing 298a, but may be defined within the flow sensor housing 300, if desired. The flow sensor 298 is received within the flow sensor housing 300, which defines a housing inlet conduit 336 and a housing outlet conduit 338. The housing inlet conduit 336 is fluidly coupled to the outlet 200 and the sensor inlet 330; and the housing outlet conduit 338 is fluidly coupled to the sensor outlet 332 and the band conduit 322 to provide the fluid or insulin to the cannula 294.

With reference back to FIG. 7, the flow sensor housing 300 defines a cannula receiving portion 340, a sensor receiving portion 342 and a connecting portion 344. The flow sensor housing 300 may be composed of a suitable biocompatible material, such as a polymer-based material, metal or metal alloy, which is cast, molded, printed, stamped, etc. With brief reference to FIG. 4, the cannula receiving portion 340 is cylindrical, and is sized to receive the cannula plug 292 and the cannula 294. The cannula receiving portion 340 is positioned over the third receiving projection 142 of the second housing 112 (FIG. 4). The cannula receiving portion 340 is fluidly coupled to the sensor receiving portion 342 via the housing outlet conduit 338, which is defined in the cannula receiving portion 340. With reference back to FIG. 7, the sensor receiving portion 342 is substantially rectangular, however, the sensor receiving portion 342 may have any desired shape to receive the flow sensor 298. The sensor receiving portion 342 also defines channels 342a (FIG. 4), which receive a portion of the sealing members 334a, 334b to create the seal between the flow sensor 298 and the flow sensor housing 300. The connecting portion 344 fluidly couples the valve assembly 114 to the cannula assembly 116. In one example, the connecting portion 344 is cylindrical, and includes a sealing member 346. In this example, the sealing member 346 is an elastomeric O-ring, however, other sealing mechanisms may be employed. The sealing member 346 is received within an inlet 348 of the flow sensor housing 300 and forms a seal about the outlet 200 of the stator 164 and the flow sensor housing 300, as shown in FIG. 4. The connecting portion 344 also defines the housing inlet conduit 336, which fluidly couples the outlet 200 to the sensor inlet 330.

Figure 8:
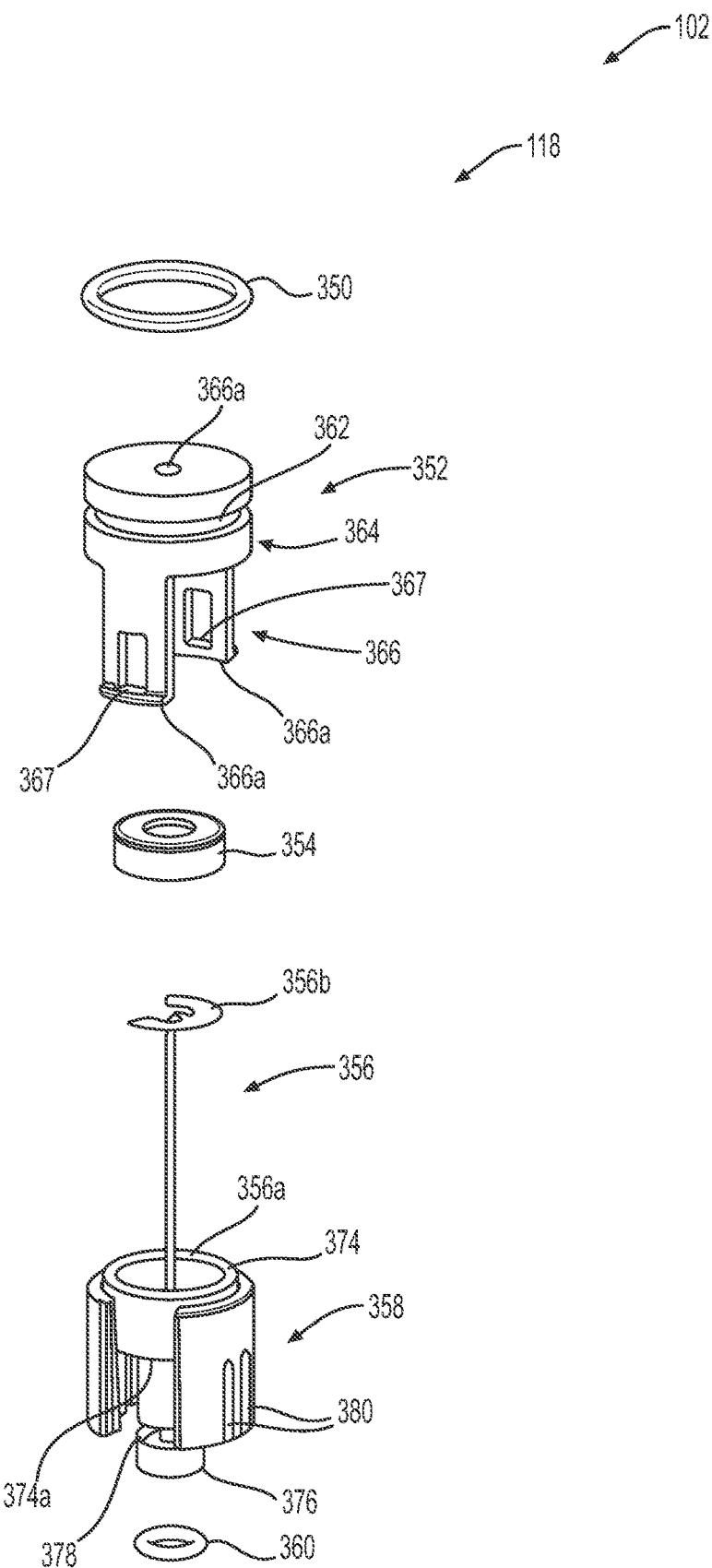
FIG. 8 is an exploded view of a continuous glucose monitor assembly associated with the wearable infusion port of FIG. 1.

The continuous glucose monitor assembly 118 is positionable within the receiving projection 130 of the first housing 110, and is also received within the second receiving projection 140 of the second housing 112. It should be noted that the continuous glucose monitor assembly 118 may be optional, and that the wearable infusion port 102 need not include the continuous glucose monitor assembly 118, if desired. If the continuous glucose monitor assembly 118 is not employed with the wearable infusion port 102, the receiving projection 130 of the first housing 110 may receive a plug or other structure to enclose the receiving projection 130, if desired. With reference to FIG. 8, the continuous glucose monitor assembly 118 includes a sensor sealing member 350, a first sensor housing 352, a sensor septum 354, a glucose sensor 356, a second sensor housing 358 and a second sensor sealing member 360. The sensor sealing member 350 creates a seal between the first sensor housing 352 and the first housing 110 (FIG. 4). In one example, the sensor sealing member 350 is an elastomeric O-ring, however, other sealing mechanisms may be employed. The sensor sealing member 350 is received within a seal groove 362 defined in the first sensor housing 352, and extends about a perimeter of the first sensor housing 352.

The first sensor housing 352 is coupled to the second sensor housing 358. The first sensor housing 352 and the second sensor housing 358 are each composed of a suitable biocompatible material, such as a polymer-based material, metal or metal alloy, which is cast, molded, printed, stamped, etc. The first sensor housing 352 includes a first base 364 and a pair of legs 366. The first base 364 includes a top surface 365 and an opposite bottom surface 368. The top surface 365 defines a bore 365a, which enables the receipt of a needle from an inserter (not shown) to couple the glucose sensor 356 to the user. The seal groove 362 is defined about the perimeter or circumference of the first base 364 between the top surface 365 and the bottom surface 368. With reference to FIG. 4, the bottom surface 368 includes a groove 368a, which assists in coupling the first sensor housing 352 to the second sensor housing 358.

The legs 366 couple the continuous glucose monitor assembly 118 to the first housing 110. In one example, each of the legs 366 are cantilevered relative to the first base 364 such that the legs 366 may flex relative to the first base 364. Each of the legs 366 includes a lip 367 at a distalmost end 366a. The lip 367 cooperates with the receiving projection 130 of the first housing 110 to couple or retain the continuous glucose monitor assembly 118 within the first housing 110, as shown in FIG. 4. In one example, the lips 367 cooperate with an endwall 130b of the receiving projection 130 to form a snap-fit, which secures the continuous glucose monitor assembly 118 within the first housing 110. Generally, upon insertion of the continuous glucose monitor assembly 118, the legs 366 deflect slightly inward toward the glucose sensor 356. Once the continuous glucose monitor assembly 118 is fully inserted, the legs 366 extend past the endwall 130b, which enables the legs 366 to deflect outward and the lips 367 to engage with the endwall 130b.

With reference back to FIG. 8, the sensor septum 354 is coupled between the bottom surface 368 and the glucose sensor 356. The sensor septum 354 serves to prevent the ingress and egress of fluids into/out of the glucose sensor 356. The sensor septum 354 is pierceable by a piercing member of the insertion device to enable the insertion device to couple the glucose sensor 356 to the user. The sensor septum 354 also serves to compress the glucose sensor 356 to ensure that electrical contact is maintained between the glucose sensor 356 and the second sensor housing 358.

The glucose sensor 356 employed with the sensor inserter is a continuous glucose sensor of the type used by diabetic users. For the sake of brevity, conventional aspects and technology related to glucose sensors and glucose sensor fabrication may not be described in detail here. In this regard, known and/or conventional aspects of glucose sensors and their manufacturing may be of the type described in, but not limited to: U.S. Pat. Nos. 6,892,085, 7,468,033 and 9,295,786; and United States patent application number 2009/0299301 (which are each incorporated by reference herein). Generally, the glucose sensor 356 is an electrochemical sensor that includes the glucose oxidase enzyme, as is well understood by those familiar with glucose sensor technology. The glucose oxidase enzyme enables the glucose sensor 356 to monitor blood glucose levels in a diabetic patient or user by effecting a reaction of glucose and oxygen. Again, although certain embodiments pertain to glucose sensors, the technology described here can be adapted for use with any one of the wide variety of sensors known in the art and is not limited to glucose sensors. Generally, the glucose sensor 356 includes a distal end 356a, which is positionable in subcutaneous tissue of the user by an insertion needle of the insertion device to measure the glucose oxidase enzyme. A proximal end 356b of the glucose sensor 356 is physically and electrically coupled to the second sensor housing 358. The signals from the glucose sensor 356 are transmitted to the control system 120 via the second sensor housing 358.

The second sensor housing 358 includes a second sensor receiving portion 370 and an outer sleeve 372. The second sensor receiving portion 370 is cylindrical in shape; and has a first end 374 and an opposite second end 376. The first end 374 is sized to receive and surround the sensor septum 354. The first end 374 also receives the proximal end 356b of the glucose sensor 356. Generally, the proximal end 356b of the glucose sensor 356 is coupled between the sensor septum 354 and an inner wall 374a of the first end 374 (FIG. 4). The first end 374 has a diameter, which is different, and in this example, less than a diameter of the second end 376. The second end 376 receives a portion of the glucose sensor 356 and guides the glucose sensor 356 during the insertion of the glucose sensor 356 into the anatomy. The second end 376 defines a sealing groove 378 about a perimeter or circumference of the sealing groove 378. The sealing groove 378 receives the second sensor sealing member 360.

The outer sleeve 372 surrounds a portion of the perimeter or circumference of the second sensor receiving portion 370. Generally, the outer sleeve 372 is disposed about the circumference of the second sensor receiving portion 370 so as to be disposed about a portion of the perimeter of the second receiving projection 140 of the second housing 112 when the continuous glucose monitor assembly 118 is coupled to the second housing 112 (FIG. 4). In one example, the outer sleeve 372 is substantially C-shaped, and includes one or more electrical contacts 380. The electrical contacts 380 electrically couple the glucose sensor 356 to the control system 120. The electrical contacts 380 may be coupled to the outer sleeve 372 via insert molding, adhesives, ultrasonic welding, etc. The outer sleeve 372 creates a waterproof interface to the second housing 112 with the second sensor sealing member 360.

The second sensor sealing member 360 creates a seal between the outer sleeve 372 and the second housing 112 (FIG. 4). In one example, the second sensor sealing member 360 is an elastomeric O-ring, however, other sealing mechanisms may be employed. The second sensor sealing member 360 is received within the sealing groove 378 defined in the first sensor housing 352, and extends about a perimeter of the first sensor housing 352.

With reference to FIG. 4, the control system 120 includes a power supply 390, a communication device 392 and a controller 394. In one example, the power supply 390, the communication device 392 and the controller 394 are physically and electrically coupled together via a circuit board 396. The power supply 390 supplies power to the controller 394, which in turn supplies power to the wire 260, the flow sensor 298 and the communication device 392. In one example, the power supply 390 comprises a pair of coin cell batteries 390a, 390b. It should be noted, however, that any suitable power supply 390 may be employed with the control system 120, including, but not limited to, rechargeable batteries, solar cells, etc.

The communication device 392 enables wireless communication between the wearable infusion port 102 and a remote device, such as a portable electronic device associated with the user, including, but not limited to a cell phone, tablet, personal computer, smart watch, smart glasses, infusion pump, etc. The communication device 392 is in communication with the portable electronic device via any suitable communication protocol supported by the portable electronic device. In an exemplary embodiment, the communication device 392 is a wireless communication system configured to communicate via a wireless local area network (WLAN) using IEEE 802.11 standards, Bluetooth® or by using cellular data communication. Thus, the communication device 392 includes, but is not limited to, a Bluetooth® transceiver, a radio transceiver, a cellular transceiver, a 2G/3G/4G LTE transceiver and/or a Wi-Fi transceiver. The communication device 392 can also comprise a one-way transmitter. The communication device 392 may also be configured to encode data or generate encoded data. The encoded data generated by the communication device 392 may be encrypted. Thus, the communication device 392 enables the controller 394 of the wearable infusion port 102 to communicate data, such as the volume of fluid dispensed by the valve assembly 114 (as observed by the flow sensor 298), a blood glucose level of the user (as observed by the glucose sensor 356), etc. The communication device 392 also enables the controller 394 to receive data, such as a volume of fluid to be dispensed to the user, from the remote device.

The controller 394 includes at least one processor 398 and a computer readable storage device or media 400. The processor 398 can be any custom made or commercially available processor, a central processing unit (CPU), a graphics processing unit (GPU), an auxiliary processor among several processors associated with the controller 394, a semiconductor based microprocessor (in the form of a microchip or chip set), a macroprocessor, any combination thereof, or generally any device for executing instructions. The computer readable storage device or media 400 may include volatile and nonvolatile storage in read-only memory (ROM), random-access memory (RAM), and keep-alive memory (KAM), for example. KAM is a persistent or non-volatile memory that may be used to store various operating variables while the processor 398 is powered down. The computer-readable storage device or media 400 may be implemented using any of a number of known memory devices such as PROMs (programmable read-only memory), EPROMs (electrically PROM), EEPROMs (electrically erasable PROM), flash memory, or any other electric, magnetic, optical, or combination memory devices capable of storing data, some of which represent executable instructions, used by the controller 394 in controlling components associated with the wearable infusion port 102.

The instructions may include one or more separate programs, each of which comprises an ordered listing of executable instructions for implementing logical functions. The instructions, when executed by the processor 398, receive and process input signals, perform logic, calculations, methods and/or algorithms for controlling the components of the wearable infusion port 102, and generate control signals to components of the wearable infusion port 102 to output one or more control signals and/or data based on the logic, calculations, methods, and/or algorithms Although only one controller 394 is shown in FIG. 4, embodiments of the wearable infusion port 102 can include any number of controllers 394 that communicate over any suitable communication medium or a combination of communication mediums and that cooperate to process the sensor signals, perform logic, calculations, methods, and/or algorithms, and generate control signals to control features of the wearable infusion port 102.

In various embodiments, one or more instructions of the controller 394 are associated with the wearable infusion port 102 and, when executed by the processor 398, the instructions receive and process signals from the glucose sensor 356 and determine a value of the blood glucose level of the user. In various embodiments, the instructions of the controller 394, when executed by the processor 398, receive and process signals from the flow sensor 298 and determine a volume of fluid or insulin that has been dispensed by the valve assembly 114. In various embodiments, the instructions of the controller 394, when executed by the processor 398, output one or more control signals to the valve assembly 114 to move the valve assembly 114 from the closed state to the opened state to dispense fluid or insulin to the user based on the blood glucose level of the user. In various embodiments, the instructions of the controller 394, when executed by the processor 398, output one or more control signals to the valve assembly 114 to move the valve assembly 114 from the opened state to the closed state based on the determined volume of the fluid or insulin dispensed.

The adhesive patch 122 couples the wearable infusion port 102 to the user. The adhesive patch 122 is coupled to the second surface 112a of the second housing 112 and affixes the second housing 112, and thus, the wearable infusion port 102, to an anatomy, such as the skin of the user. The adhesive patch 122 may be composed of a flexible and breathable material with one or more adhesive layers, such as cloth, a bandage-like material, and the like. For example, suitable materials could include polyurethane, polyethylene, polyester, polypropylene, polytetrafluoroethylene (PTFE), or other polymers, to which one or more adhesive layers are applied. The adhesive patch 122 may include a backing layer, which is removable to expose the one or more adhesive layers.

In one example, with reference to FIG. 3, in order to assemble the wearable infusion port 102, the first housing 110 and the second housing 112 may be formed. The adhesive patch 122 is coupled to the second housing 112 and the cannula assembly 116 may be assembled. With reference to FIG. 7, with the flow sensor 298 and the flow sensor housing 300 formed, the flow sensor 298 is positioned within the flow sensor housing 300 such that the sealing members 334a, 334b surround the respective one of the sensor inlet 330 and sensor outlet 332 to create a seal between the sensor inlet 330, the sensor outlet 332 and the flow sensor housing 300. With the sealing band 306 coupled to the cannula plug 292 and the cannula 294 formed, the cannula plug 292 is coupled to the cannula 294, and the cannula 294 is inserted into the flow sensor housing 300 such that the cannula sealing member 296 is positioned between the flow sensor housing 300 and the cannula inlet 326. The sealing member 346 is coupled to the flow sensor housing 300. The flow sensor housing 300 is coupled to the second housing 112, as shown in FIG. 4.

With reference to FIG. 5, the valve assembly 114 may be assembled. In one example, with the actuator shaft 232 formed, the wire 260 may be inserted through the actuator shaft 232. The first post 256 and the second post 258 may be coupled to the wire 260. With the stator 164 formed, the ratchet shim 162 is coupled to the stator 164. With the rotor 160 formed, the rotor 160 is inserted into the stator 164. The actuator shaft 232 is positioned within the stator 164. With the actuator pinion 236 formed, the actuator pinion 236 may be positioned within the stator 164. The actuator pinion 236 is received within the stator 164 such that the shaft teeth 244 engage the pinion teeth 268. The actuator shim 238 is coupled to the actuator pinion 236, and the end plate 240 is coupled to the shaft 175 of the rotor 160. With the valve assembly 114 assembled, the valve assembly 114 is coupled to the second housing 112 as shown in FIG. 4.

With reference to FIG. 8, the continuous glucose monitor assembly 118 may also be assembled. In one example, with the second sensor housing 358 formed, the glucose sensor 356 is positioned through the second sensor housing 358. The electrical connection is established between the glucose sensor 356 and the outer sleeve 372. The sensor septum 354 is positioned over the proximal end 356b of the glucose sensor 356. With the first sensor housing 352 formed, the first sensor housing 352 is positioned over the second sensor housing 358 to compress the sensor septum 354. The sensor sealing member 350 is positioned within the seal groove 362 of the first sensor housing 352.

With reference to FIG. 3, the control system 120 is assembled by electrically and physically coupling the power supply 390, the communication device 392 and the controller 394 to the circuit board 396. The power supply 390, the communication device 392 and the flow sensor 298 are each in communication with the controller 394. The circuit board 396 is coupled to the second housing 112. The flange 215 is electrically and physically coupled to the circuit board 396 such that the wire 260 is in communication with the controller 394 to receive the one or more control signals to heat the wire 260. The needle septum 290 is positioned over the cannula plug 292. The first housing 110 is coupled to the second housing 112. The continuous glucose monitor assembly 118 is coupled to the first housing 110, via the snap-fit engagement of the legs 366 with the endwall 130b of the receiving projection 130 (FIG. 4).

With the wearable infusion port 102 assembled, the wearable infusion port 102 may be packaged, sterilized and provided to an end user. Once received, the user may remove the packaging to expose the wearable infusion port 102. The user may remove the backing layer, if any, from the adhesive patch 122. The user may manipulate the insertion device (not shown) to deploy the wearable infusion port 102 onto the user such that the distal end 356a of the glucose sensor 356 (FIG. 4) and the distal end 324 of the cannula 294 (FIG. 4) are each positioned within the subcutaneous tissue of the user. The adhesive patch 122 couples the wearable infusion port 102 to the anatomy, such as the skin, of the user.

With the wearable infusion port 102 coupled to the user, with reference to FIG. 4, the user may dispense the fluid or insulin F into the first needle port 132. The fluid F flows from the first needle port 132 (which is an inlet for the wearable infusion port 102) into the central bore 180 of the rotor 160. With reference to FIG. 6, the valve assembly 114 is shown in the closed state. In the closed state, the second post 258 extends beyond the end 250 of the actuator shaft 232, and one of the conduits 194 of the conduit sleeve 170 is not aligned with the outlet conduit 224. Based on the receipt of the one or more control signals (or power) from the control system 120, with reference to FIG. 9, as the wire 260 begins to increase in temperature, which causes the wire 260 to contract or move toward the stator 164. The contraction of the wire 260 causes the second post 258 to contact the flange 254. The continued contraction of the wire 260 overcomes the spring force Fs (FIG. 5) and causes the second post 258 to move the actuator shaft 232 linearly in a direction D toward the flange 215. The translation of the actuator shaft 232 rotates the actuator pinion 236, which in turn, via the actuator shim 238 and the end plate 240, rotates the rotor 160. In one example, the contraction of the wire 260 moves the rotor 160 about 20 degrees counterclockwise.

Figure 10:
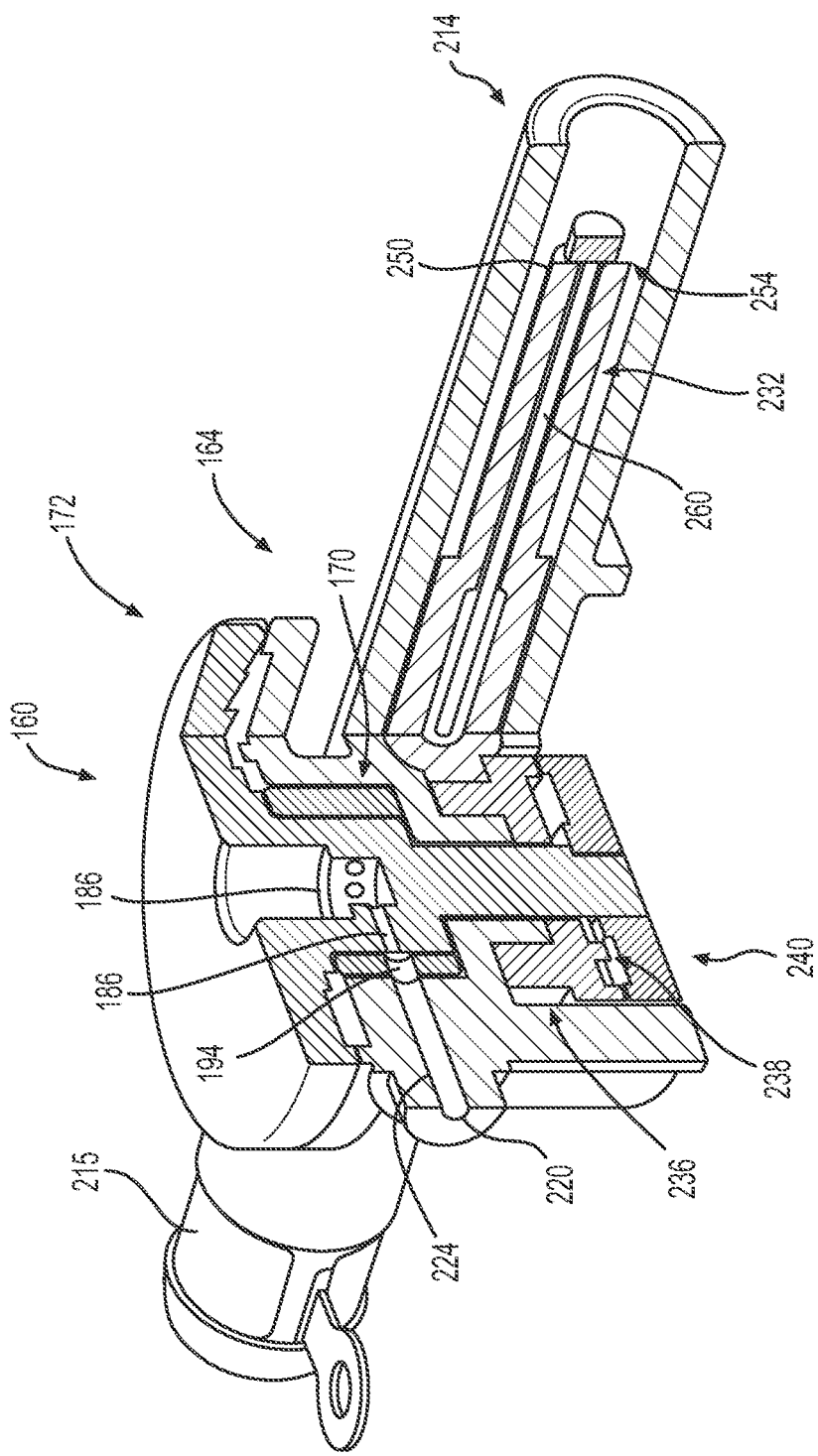
FIG. 10 is a cross-sectional view of the valve assembly, taken along line 6-6 of FIG. 5A, which illustrates the valve assembly moving in the opened state in accordance with various embodiments.

The rotation of the rotor 160 moves the conduit sleeve 170 until one of the conduits 194 aligns with the outlet conduit 224 as shown in FIG. 10. The valve assembly 114 is in the opened state in FIG. 10. With the conduit 194 aligned with the outlet conduit 224, the fluid flows from the rotor 160 to the outlet 220. Once the valve assembly 114 is in the opened state, the controller 394 outputs one or more control signals (removes the power) to the actuator shaft 232. With the power removed, the wire 260 cools. As the wire 260 cools, the spring force Fs of the spring 230 (FIG. 5) moves or translates the actuator shaft 232 back to the first position (as shown in FIG. 6). The movement or translation of the actuator shaft 232 moves or rotates the actuator pinion 236 clockwise to its original position (as shown in FIG. 6). In one example, the actuator pinion 236 moves or rotates about 20 degrees clockwise back into the original position. The rotor 160, however, does not move or rotate with the actuator shaft 232 as the ratchet shim 162 and the actuator shim 238 inhibit the rotation of the shaft 175 clockwise.

With reference to FIG. 4, from the outlet 200, the fluid F flows into the housing inlet conduit 336 of the flow sensor housing 300. From the housing inlet conduit 336 the fluid F flows into the sensor inlet 330 of the flow sensor 298. The fluid F is heated by the heater 328, and the temperature sensors 329a, 329b observe the temperature of the fluid F (FIG. 7). The fluid F flows into the sensor outlet 332 and from the sensor outlet 332 through the housing outlet conduit 338 of the flow sensor housing 300. From the housing outlet conduit 338, the fluid flows through the band conduit 322 into the cannula plug 292, and into the cannula 294. The fluid F exits the distal end 324 of the cannula 294 into the subcutaneous tissue.

Figure 9:
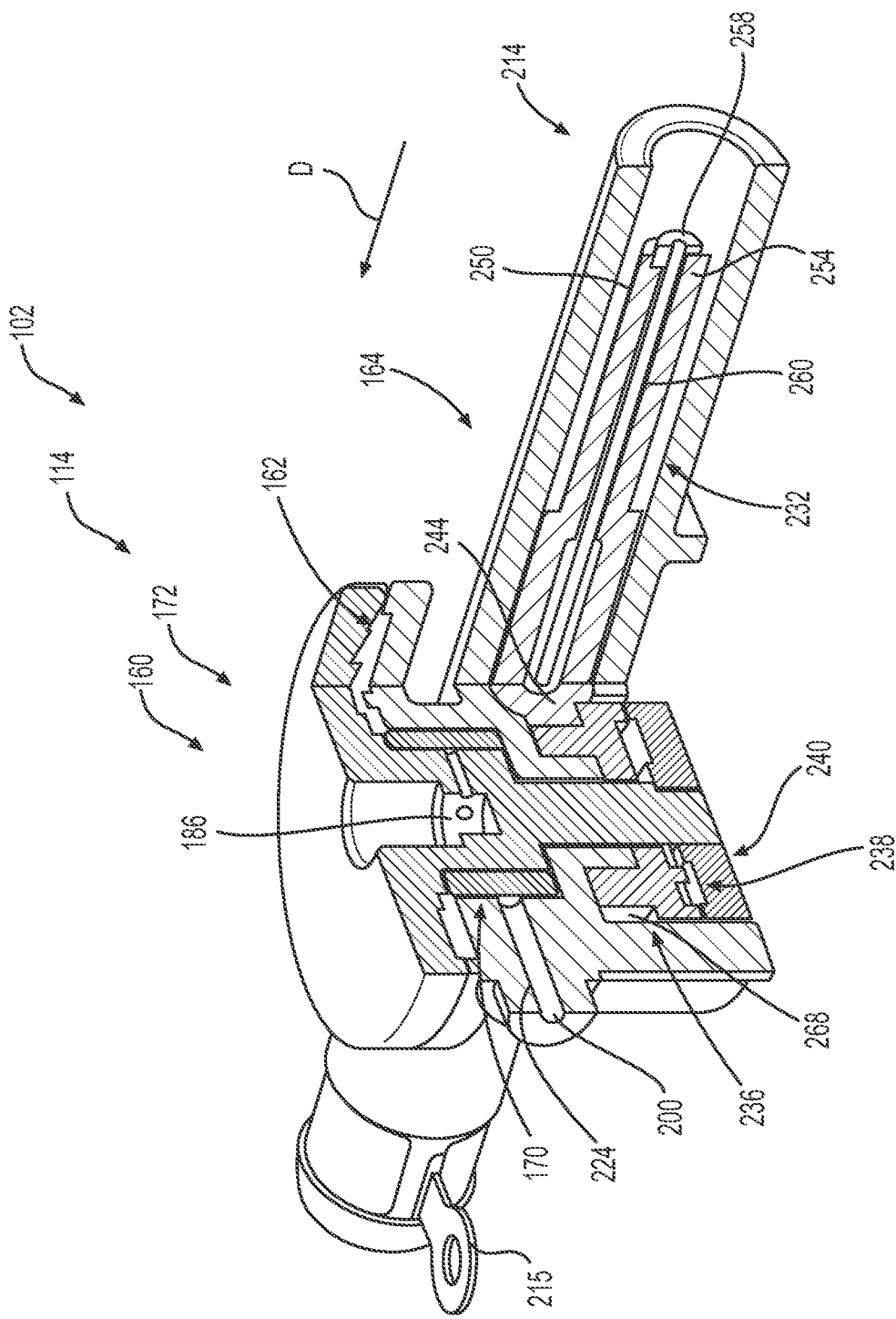
FIG. 9 is a cross-sectional view of the valve assembly, taken along line 6-6 of FIG. 5A, which illustrates the valve assembly moving from the closed state to an opened state in accordance with various embodiments.

The temperature sensors 329a, 329b communicate the sensor signals to the controller 394. The controller 394 determines the volume of the fluid F dispensed based on the change in temperatures. Based on the determined volume dispensed, the controller 394 outputs one or more control signals (or power) from the control system 120 to move the valve assembly 114 from the opened state to the closed state. With reference to FIG. 9, as the wire 260 begins to increase in temperature, the wire 260 contracts or move toward the stator 164. The contraction of the wire 260 causes the second post 258 to contact the flange 254. The continued contraction of the wire 260 overcomes the spring force Fs (FIG. 5) and causes the second post 258 to move the actuator shaft 232 linearly in a direction D toward the flange 215. The translation of the actuator shaft 232 rotates the actuator pinion 236, which in turn, via the actuator shim 238 and the end plate 240, rotates the rotor 160. In one example, the contraction of the wire 260 moves the rotor 160 about 20 degrees counterclockwise. As the conduits 194 are spaced about 40 degrees apart, the rotation of the rotor 160 about 20 degrees counterclockwise results in one of the conduits 194 being misaligned with the outlet conduit 224 as shown in FIG. 6, which inhibits the flow of the fluid F through the outlet 200.

Once coupled to the user, the control system 120 of the wearable infusion port 102 communicates with the portable electronic device and may send one or more notifications to the portable electronic device for display on the portable electronic device, including, but not limited to, blood glucose levels, a volume of insulin dispensed, etc. In addition, the control system 120 may also be able to determine when the wearable infusion port 102 is low or needs an additional quantity of insulin. For example, the rotor 160 may serve as a fluid reservoir, which may hold more fluid or insulin than necessary for a single dose. The processor 398 of the control system 120 may be configured to determine, based on the sensor signals from the flow sensor 298 and a known quantity of fluid or insulin that may be contained in the rotor 160, a quantity or volume of the fluid or insulin remaining within the reservoir defined by the rotor 160. Based on this determination, the control system 120 may be configured to output one or more notifications to the user to dispense additional quantities of fluid into the wearable infusion port 102. Generally, once coupled to the user, the wearable infusion port 102 may be worn by the user for about 7 to about 10 days.

Thus, the wearable infusion port 102 enables a user to infuse a fluid, such as insulin, into the subcutaneous tissue of the user over an extended period of time without requiring the user to directly inject the fluid into the anatomy of the user. This greatly reduces the number of times the user has to insert a needle or pierced tip instrument into their anatomy, while providing the user with the necessary infusion therapy. For users who require multiple injections of fluid or insulin a day, the user is subjected to a single insertion of the wearable infusion port 102 instead of multiple insertions with needle syringes, etc. The wearable infusion port 102 also enables the user to monitor their blood glucose levels via the remote device, and the control system 120 of the wearable infusion port 102 and/or the remote device is configured to control the wearable infusion port 102 to dispense the insulin based on the blood glucose levels. This can provide the user with an experience similar to that provided by an infusion pump, with a smaller form factor. In addition, the use of the flow sensor 298 with the wearable infusion port 102 may detect occlusions of the wearable infusion port 102 (via a volume of fluid flow observed) and also ensures the delivery of the proper amount.

Figure 11:
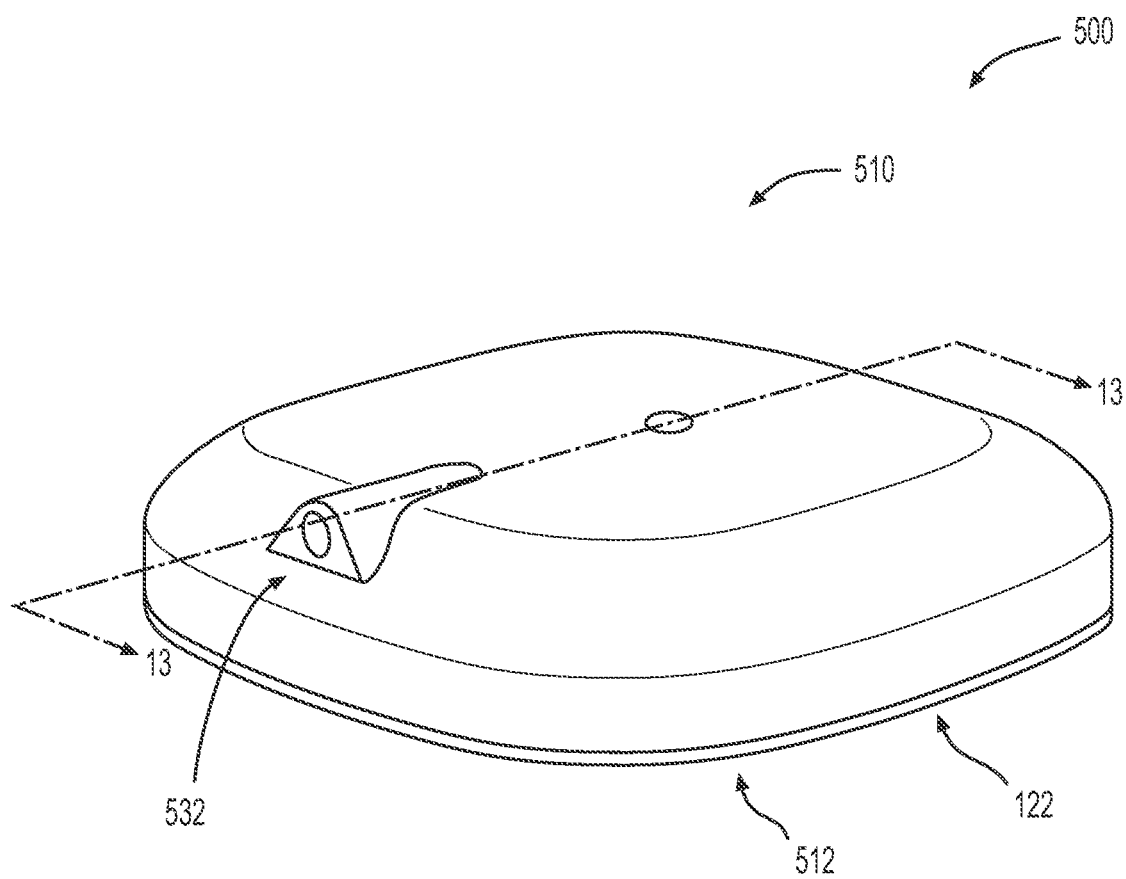
FIG. 11 is a perspective view of another wearable infusion port in accordance with various embodiments.

It should be noted that in other embodiments, the wearable infusion port 102 may be configured differently to deliver fluid, such as insulin, to a user over an extended period of time. For example, with reference to FIG. 11, a wearable infusion port 500 is shown. As the wearable infusion port 500 includes the same or similar components as the wearable infusion port 102 discussed with regard to FIGS. 1-10, the same reference numerals will be used to denote the same or similar components. The wearable infusion port 500 is generally rectangular or square, however, it will be understood that the wearable infusion port 500 may have any desired shape. In one example, with reference to FIG. 12, the wearable infusion port 500 includes an upper or first housing 510, a bottom or second housing 512, a valve assembly 514, a cannula assembly 516, and a control system 520. The wearable infusion port 500 may be coupled to the user via the adhesive patch 122.

Figure 13:
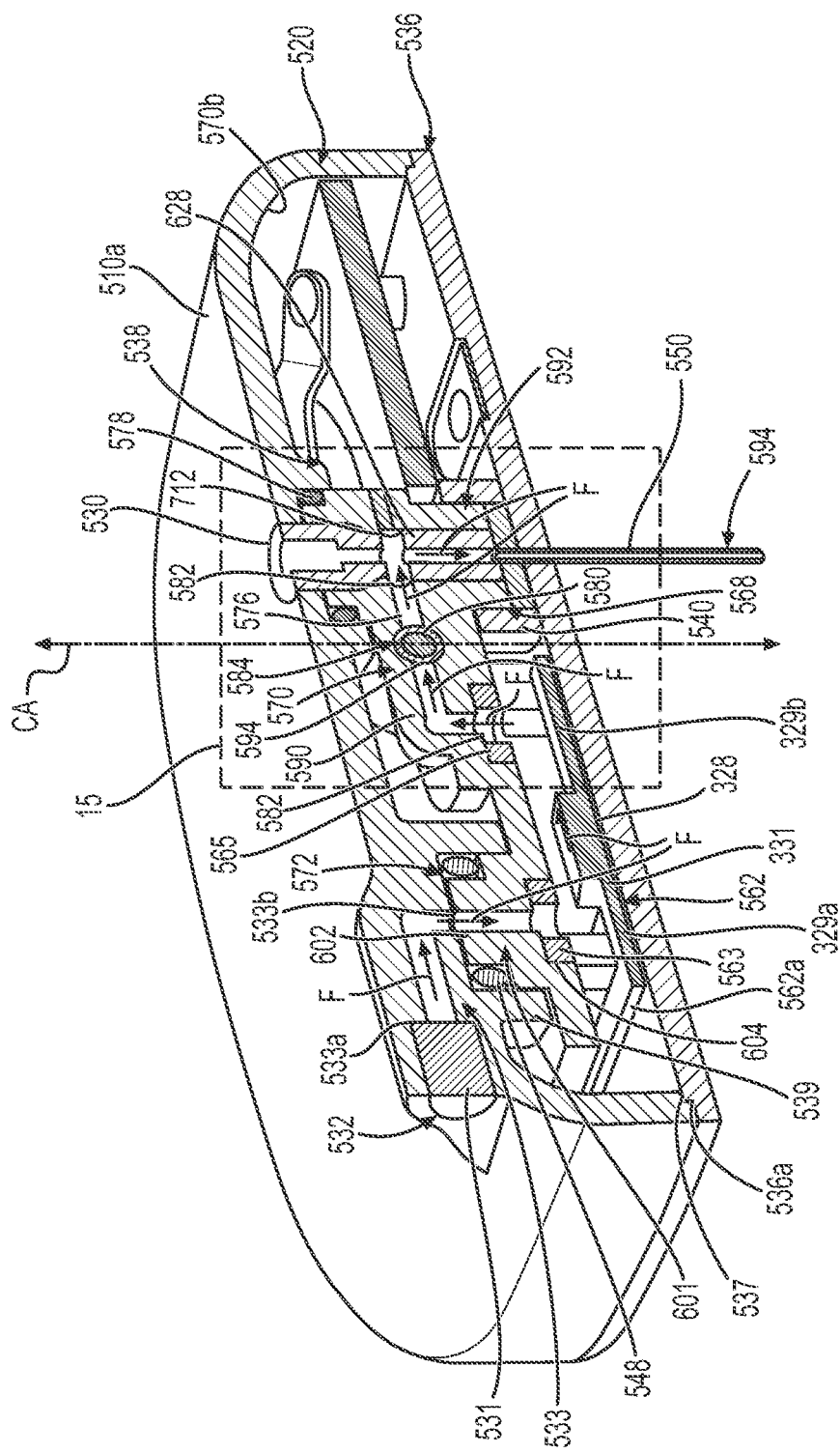
FIG. 13 is a cross-sectional view of the wearable infusion port of FIG. 11, taken along line 13-13 of FIG. 11.
Figure 13A:
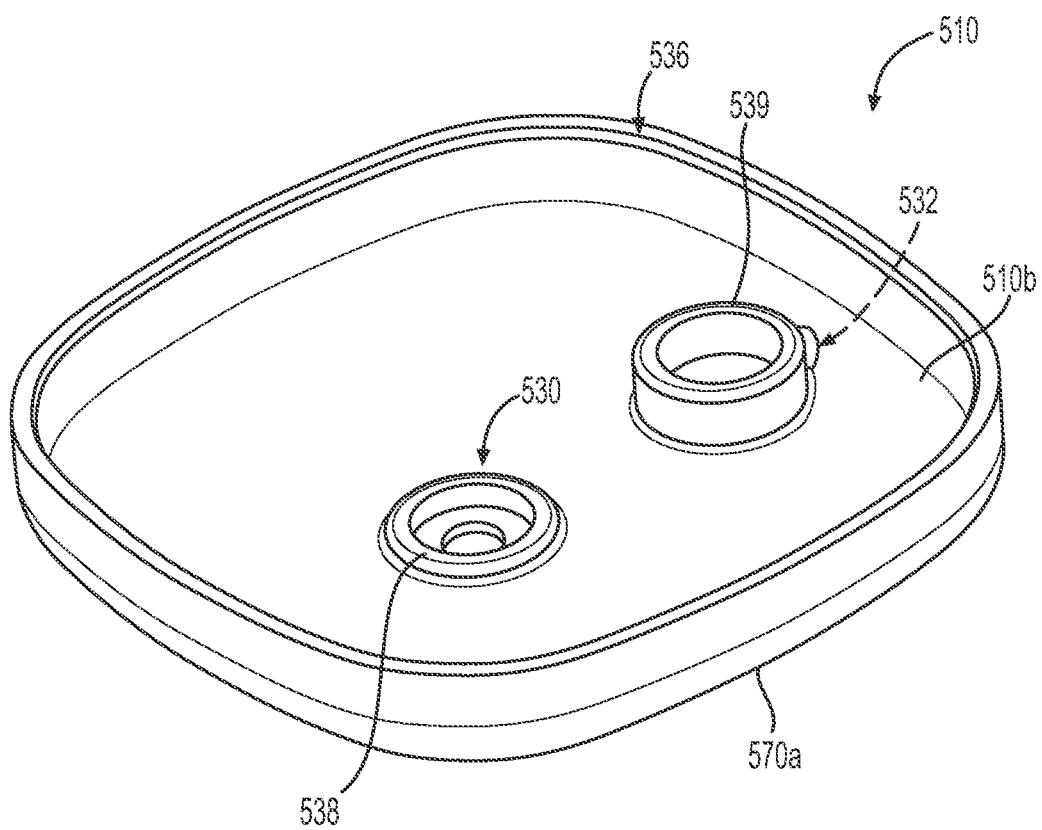
FIG. 13A is a bottom perspective view of a first housing associated with the wearable infusion port of FIG. 11.

The first housing 510 and the second housing 512 may be composed of a suitable biocompatible material, including, but not limited to a biocompatible polymer-based material, which may be molded, printed, cast, etc. The first housing 510 and the second housing 512 are substantially rectangular or square, however, the first housing 510 and the second housing 512 may have any desired shape. The first housing 510 and the second housing 512 cooperate to substantially enclose the valve assembly 514, the cannula assembly 516 and the control system 520. With reference to FIGS. 13 and 13A, the first housing 510 defines a receiving bore 530, a first needle port 532 and a coupling interface 536. The first housing 510 may also define a receiving projection 538 and a second receiving projection 539 on a second surface 510b.

With reference back to FIG. 13, the receiving bore 530 receives a portion of the cannula assembly 516 for coupling the cannula assembly 516 to the first housing 510. Generally, the receiving bore 530 extends inward, through a first surface 510a of the first housing 510, toward the second housing 512. The first surface 510a is opposite the second surface 510b. The receiving bore 530 is shown as cylindrical (FIG. 13A), but may have any desired shape. The first needle port 532 is defined through the first surface 510a of the first housing 510, and enables a needless syringe, infusion pen or other device, such as the pump 104, to dispense fluid into the wearable infusion port 500. The first needle port 532 is in fluid communication with the valve assembly 514 to provide the fluid received through the first needle port 532 to the valve assembly 514, as will be discussed. The first needle port 532 defines an inlet for the wearable infusion port 500. The first needle port 532 includes a septum 531 and a conduit 533. The septum 531 is disposed upstream from an inlet 533a of the conduit 533. The septum 531 serves to prevent the ingress and egress of fluids into/out of and into first needle port 532. The conduit 533 extends through the first housing 510 from the first needle port 532 to the second surface 510b. The inlet 533a is defined in the first housing 510 downstream of the septum 531, and is in fluid communication with the first needle port 532. The conduit 533 has an outlet 533b downstream of the inlet 533a. The outlet 533b fluidly couples the first needle port 532 to the valve assembly 514 to provide the valve assembly 514 with the fluid or insulin. The outlet 533b in this example is defined through the second surface 510b so as to extend along an axis transverse or substantially perpendicular to an axis that extends through the inlet 533a.

The coupling interface 536 is defined about a perimeter of the first housing 510. The coupling interface 536 defines a sidewall 536a, and includes an interlock recess 537. The sidewall 536a extends about the perimeter of the first housing 510, and extends from the first surface 510a generally so as to be substantially parallel to a center axis CA of the wearable infusion port 500. The sidewall 536a cooperates with the second housing 512 to substantially enclose the valve assembly 514, the cannula assembly 516 and the control system 520. The interlock recess 537 is defined about a perimeter of the sidewall 536a, and in one example, is a relief having a square notch 538a. The square notch 538a interfaces with or interlocks with a corresponding feature on the second housing 512 to assist in coupling the first housing 510 to the second housing 512 with a waterproof seal. It should be understood, however, that the interlock recess 537 may not include the square notch 538a, but rather may define an endwall that is substantially perpendicular to the center axis CA (FIG. 2) or that a notch associated with the interlock recess 537 may have a different shape.

The receiving projection 538 is substantially cylindrical (FIG. 13A) and extends from the second surface 510b toward the second housing 512. The receiving projection 538 assists in coupling the valve assembly 114 between the first housing 510 and the second housing 512. The second receiving projection 539 is substantially cylindrical (FIG. 13A) and extends from the second surface 510b toward the second housing 512. The second receiving projection 539 also assists in coupling the valve assembly 114 between the first housing 510 and the second housing 512.

Figure 12:
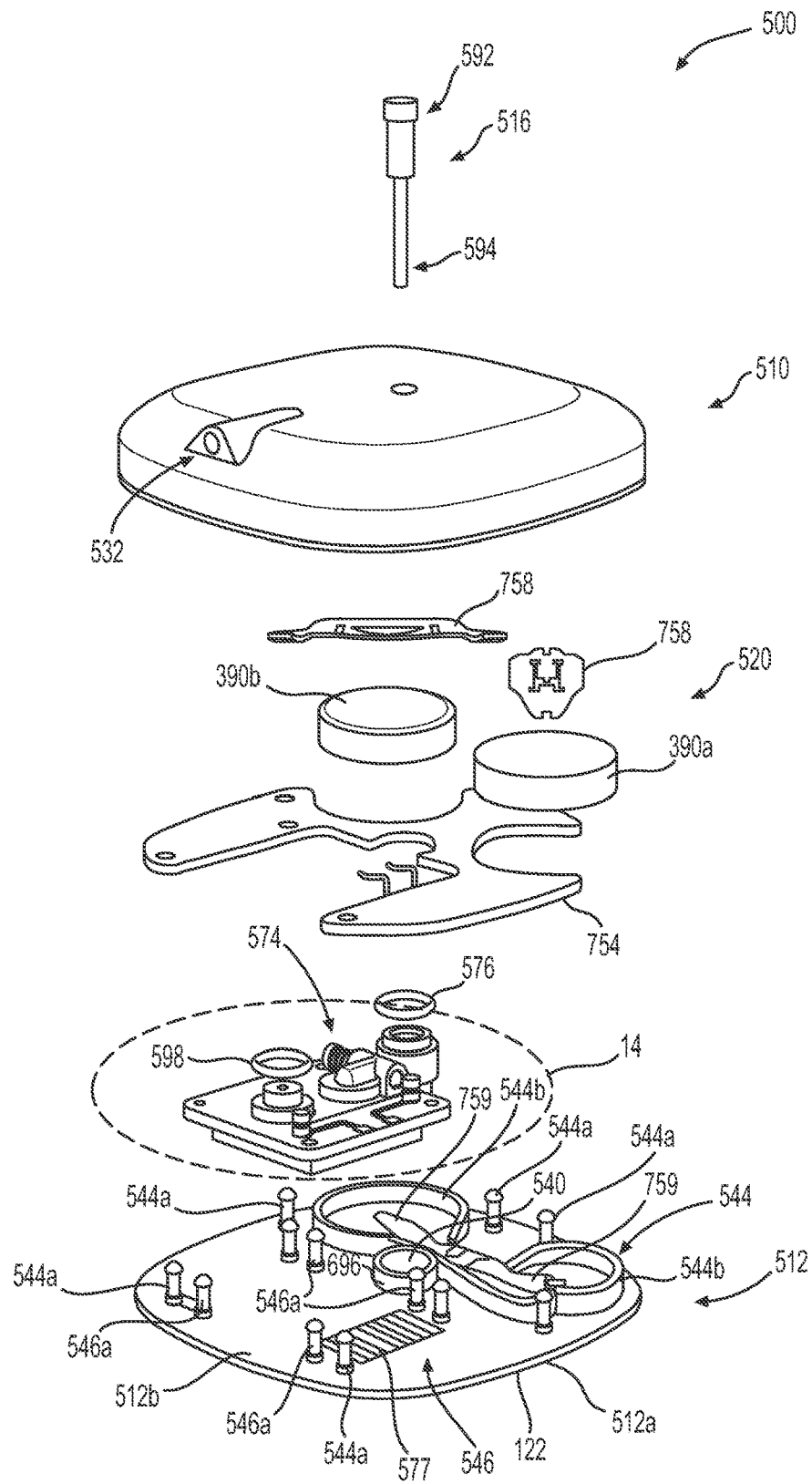
FIG. 12 is an exploded view of the wearable infusion port of FIG. 11.

The second housing 512 is coupled to the first housing 510. With reference to FIG. 12, the second housing 512 includes a second receiving projection 540, a control receiving portion 544 and a valve receiving portion 546. The second receiving projection 540 cooperates with the receiving bore 530 of the first housing 510 and the receiving projection 538 to receive the cannula assembly 516. The second receiving projection 540 defines a second bore 550 (FIG. 13). The second bore 150 is defined through the second housing 512. The second bore 150 enables a portion of the cannula assembly 116 to pass through the second housing 512 and into the anatomy when the wearable infusion port 500 is coupled to a user.

With reference to FIG. 12, the control receiving portion 544 is defined along a third surface 512b of the second housing 512, which is opposite a second surface 512a. In this example, the control receiving portion 544 includes at least one or a pair of posts 544a, which cooperate to retain a portion of the control system 520 within the second housing 512. The control receiving portion 544 may also include power supply ribs 544b, which assist in assembling a portion of the control system 520 to the second housing 512. The valve receiving portion 546 includes a plurality of posts 546a.

Figure 14:
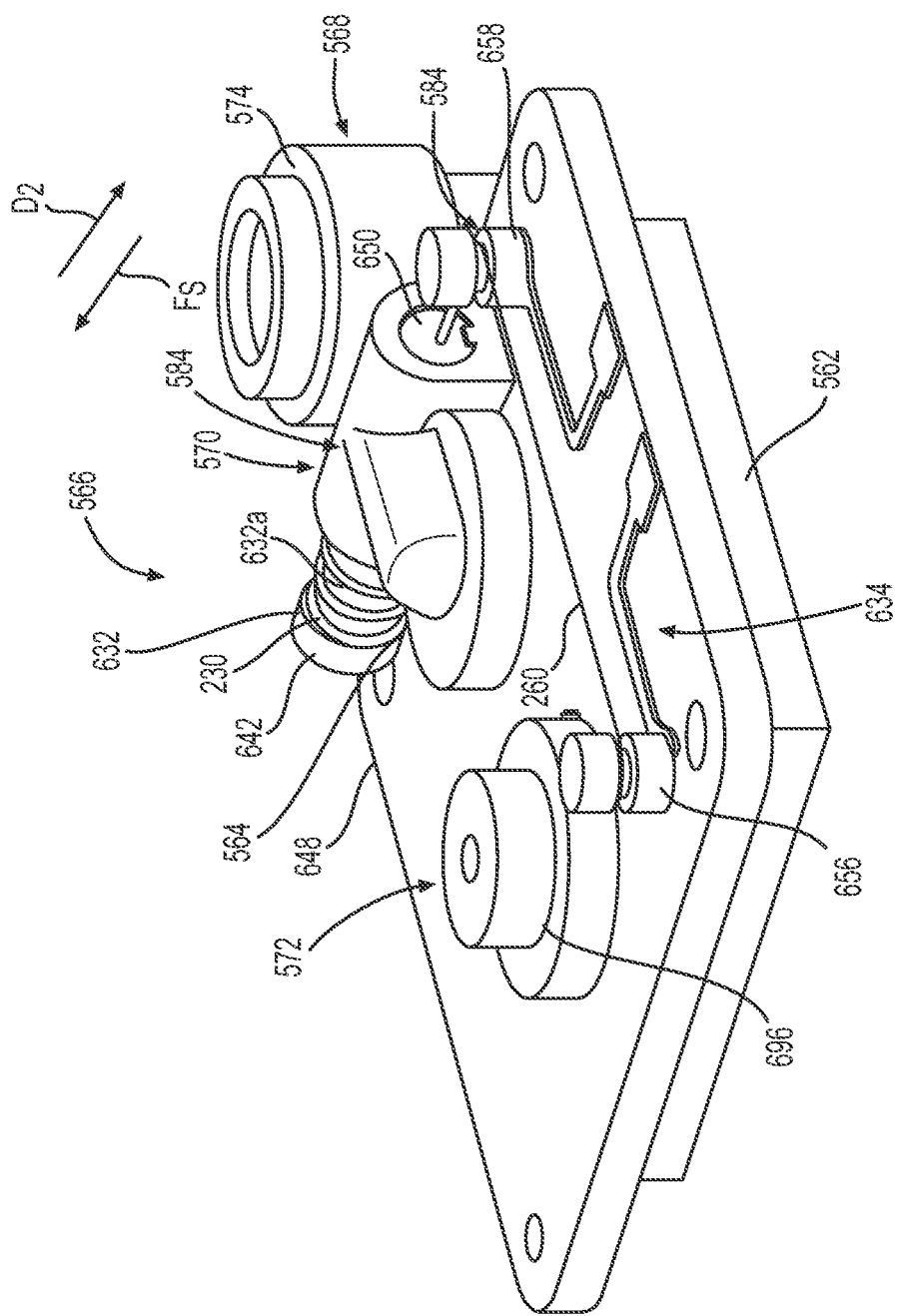
FIG. 14 is a perspective view of a valve assembly associated with the wearable infusion port of FIG. 11.

The valve assembly 514 receives the fluid for infusion, which is insulin in this example, and is movable between an opened state and a closed state. In the closed state, insulin is not dispensed and in the opened state, the insulin is dispensed. With reference to FIG. 14, a detail view of the valve assembly 514 is shown. In one example, the valve assembly 514 includes a flow sensor 562, a valve housing 564 and an actuator assembly 566.

With reference to FIG. 14, the flow sensor 562 is in fluid communication with the valve housing 564. The flow sensor 562 is in fluid communication with the valve housing 564 to observe or measure an amount of fluid or insulin received within the valve housing 564. The flow sensor 562 observes an amount of fluid that passes through the valve housing 564 from the first needle port 532, and generates one or more signals based on the observation. The flow sensor 562 is in communication with the control system 520 to provide the control system 520 with the sensor signals. In one example, the flow sensor 562 observes a volume of the insulin that passes through the valve housing 564 to the cannula assembly 516, through the cannula assembly 516 and into the user. Thus, the flow sensor 562 observes a volume of the fluid or insulin that is received by the valve assembly 514. As will be discussed, based on the signals received from the flow sensor 562, the control system 520 may output one or more control signals to the valve assembly 514 to move the valve assembly 514 from the opened state to the closed state.

In one example, the flow sensor 562 is a thermal mass flow sensor, which detects flow rates from about 1.0 to about 40.0 milliliters per minute (mL/min). In this example, the flow sensor 562 includes the heat source or heater 328 and the pair of temperature sensors 329a, 329b on either side of the heater 328. The heater 328 and the temperature sensors 329a, 329b are coupled to or in communication with the flow conduit 331 defined within the flow sensor 562. The heater 328 heats the fluid or insulin as the fluid passes through the flow sensor 562. One of the temperature sensors observe a first temperature of the fluid (prior to heating) and the other one of the temperature sensors observes a second temperature of the fluid (after heating). The signals from the temperature sensors 329a, 329b are communicated to the control system 520, and the control system 520 determines the volume of the fluid delivered based on a difference between the two temperature signals. Thus, the flow sensor 562 is in communication with the control system 520. The signals from the temperature sensors may be filtered, if desired, to account for turbulence. It should be noted, alternatively, the flow sensor 562 may also include a monitor module, which determines the volume based on the temperature signals, and transmits the determined volume to the control system 520.

In this example, the flow sensor 562 includes a sensor inlet 563 in fluid communication with the first needle port 532 (via the valve housing 564) and a sensor outlet 565 in fluid communication with the valve housing 564. A pair of sealing members (not shown) may be coupled about a respective one of the sensor inlet 563 and the sensor outlet 565 to provide a seal between the flow sensor 562 and the valve housing 564. In one example, the sealing members 334a, 334b are elastomeric O-rings, however, other sealing mechanisms may be employed. In this example, the flow sensor 298 includes a separate housing 298a, which includes the sensor inlet 330 and the sensor outlet 332, and also contains or encloses the temperature sensors 329a, 329a, the heater 328 and the flow conduit 331. It should be noted that the flow sensor 562 need not include a separate housing 562a, but may be defined within the valve housing 564, if desired. The flow sensor 562 is generally positioned between the valve housing 564 and the third surface 512b of the second housing 512.

The valve housing 564 includes a cannula guide 568, an actuator receiving portion 570 and an inlet port 572. The cannula guide 568 is cylindrical and receives the cannula assembly 116. In one example, with reference to FIG. 13, the cannula guide 568 includes a groove 574 and a cannula conduit 576. The groove 574 assists in coupling the valve housing 564 to the first housing 510. The groove 574 has a diameter, which is different and, in this example, smaller than a diameter of the remainder of the cannula guide 568 to enable a sealing member 578 to be positioned about the groove 574. The sealing member 578 forms a seal between the first housing 510 and the valve housing 564. In one example, the sealing member 578 is an elastomeric O-ring, however, other sealing mechanisms may be employed. The cannula conduit 576 is defined within the cannula guide 568 to fluidly couple the cannula assembly 116 to the actuator assembly 566. The cannula conduit 576 receives fluid or insulin from the actuator assembly 566 when the valve assembly 114 is in the opened state. The cannula conduit 576 includes an inlet 580 in fluid communication with the actuator assembly 566, and an outlet 582 in fluid communication with the cannula assembly 116.

The actuator receiving portion 570 receives the actuator assembly 566. In one example, the actuator receiving portion 570 includes an actuator shaft receiving portion 584 and an actuator wire receiving portion 586 (FIG. 14). The actuator shaft receiving portion 584 includes a sleeve 588 and a first shaft conduit 590. With reference to FIG. 14, the sleeve 588 receives a portion of the actuator assembly 566 and guides a movement of the portion of the actuator assembly 566 relative to the valve housing 564. With reference back to FIG. 13, the first shaft conduit 590 includes a shaft inlet 592 and a shaft outlet 594. In this example, the first shaft conduit 590 is L-shaped such that the shaft inlet 592 extends along an axis that is transverse or substantially perpendicular to the shaft outlet 594; however, the first shaft conduit 590 may have any desired shape. The shaft inlet 592 is in fluid communication with the sensor outlet 565 to receive the fluid from the flow sensor 562. The shaft outlet 594 is in fluid communication with the actuator assembly 566.

The inlet port 572 is defined in the valve housing 564 so as to fluidly couple the first needle port 532 to the flow sensor 562. With reference to FIG. 13, the inlet port 572 is substantially cylindrical and defines a second groove 596. The second groove 596 assists in coupling the valve housing 564 to the first housing 510. The second groove 596 has a diameter, which is different and, in this example, smaller than a diameter of the remainder of the inlet port 572 to enable a second sealing member 598 (FIG. 13) to be positioned about the groove 574. With reference to FIG. 13, the second sealing member 598 forms a seal between the first housing 510 and the valve housing 564. In one example, the second sealing member 598 is an elastomeric O-ring, however, other sealing mechanisms may be employed. The inlet port 572 also defines a port conduit 600 to fluidly couple the first needle port 532 to the flow sensor 562. The port conduit 600 receives fluid or insulin from the first needle port 532. The port conduit 600 includes a port inlet 602 in fluid communication with the outlet 533b of the first needle port 532, and a port outlet 604 in fluid communication with the sensor inlet 563 of the flow sensor 562.

The actuator assembly 566 is responsive to one or more control signals from the control system 520 to move the valve assembly 514 between the opened state and the closed state. With reference to FIG. 14, the actuator assembly 566 includes the biasing member or spring 230, an actuator shaft 632 and an actuator wire system 634. As will be discussed, a movement or translation of the actuator shaft 632 moves the valve assembly 114 between the opened state and the closed state.

The spring 230 is coupled to an exterior surface 632a of the actuator shaft 632, and applies the spring force Fs against a collar 642 of the actuator shaft 632 to bias the actuator shaft 632 into a first position. When the actuator shaft 632 is in the first position, the valve assembly 114 is in the closed state. The spring 230 is seated between the collar 642 and the actuator shaft receiving portion 584 to apply the spring force Fs against the collar 642.

The actuator shaft 632 is cylindrical, and is received within the actuator shaft receiving portion 584. The actuator shaft 632 may be composed of a suitable biocompatible material, such as a polymer-based material, metal or metal alloy, which is cast, molded, printed, stamped, etc. The actuator shaft 632 includes the collar 642, a second shaft conduit 646 and opposed ends 648, 650. The collar 642 is defined about the exterior surface 632a of the actuator shaft 632. The collar 642 is defined to extend about the exterior surface 632a at the end 648 of the actuator shaft 632. The collar 642 has a diameter, which is different than, and in this example, greater than a diameter of the end 650. The end 650 is coupled to the wire 260. The end 650 may be overmolded over the actuator wire system 634, or may be coupled to the wire 260 through a suitable processing step, including, but not limited to ultrasonic welding, adhesives, etc.

Figure 16:
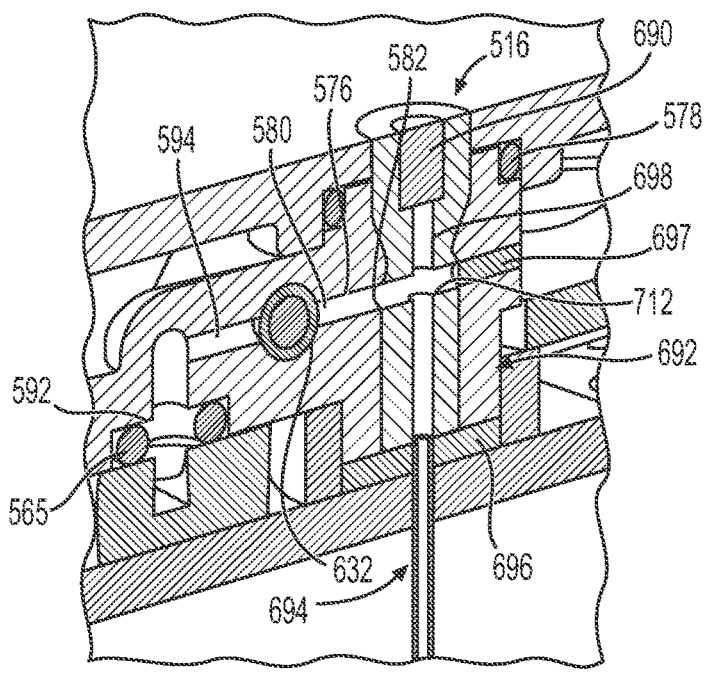
FIG. 16 is a detail view of the wearable infusion port, taken at 15 on FIG. 13, which illustrates the valve assembly in a closed state.

The second shaft conduit 646 is defined through the actuator shaft 632. In one example, the second shaft conduit 646 is defined through the actuator shaft 632 so as to extend along an axis transverse or substantially perpendicular to a longitudinal axis of the actuator shaft 632. The second shaft conduit 646 is defined through a portion of the actuator shaft 632 such that the second shaft conduit 646 is only in fluid communication with the shaft outlet 594 when the actuator shaft 632 has moved or translated from the first position to a second position in a direction D2 toward the second coupling post 658 (FIG. 14). When the second shaft conduit 646 is in the second position, the valve assembly 514 is in the opened state. The second shaft conduit 646 has an inlet 646a in fluid communication with the shaft outlet 594, and an outlet 646b in fluid communication with inlet 580 of the cannula conduit 576. When the actuator shaft 632 is in the first position, the second shaft conduit 646 is not aligned with the first shaft conduit 590, and thus, the valve assembly 514 is in the closed state, as shown in FIG. 16.

With reference to FIG. 14, the actuator wire system 634 is coupled to the actuator shaft 632. The actuator wire system 634 includes a first coupling post 656, a second coupling post 658 opposite the first coupling post 656 and the wire 260. The first coupling post 656 and the second coupling post 658 are generally cylindrical, and have a diameter that is greater than a diameter of the wire 260. The first coupling post 656 and the second coupling post 658 may be composed of a suitable conductive material, such as a metal or metal alloy, which is cast, molded, printed, stamped, etc. The first coupling post 656 and the second coupling post 658 are physically and electrically coupled to the wire to provide an electric current to the wire. The first coupling post 656 and the second coupling post 658 may be coupled to the wire 260 via wrapping of the wire 260 around the first coupling post 656 and the second coupling post 658, for example. The first coupling post 656 and the second coupling post 658 are each in communication with the control system 520 to receive one or more control signals, in this example, a current, to heat the wire 260.

As discussed, the wire 260 is a shape memory wire, and in one example, is a nitinol wire. Opposed ends of the wire 260 are coupled to a respective one of the first coupling post 656 and the second coupling post 658. In this example, the control system 520 supplies the current to the first coupling post 656, which passes through wire 260 to the second coupling post 658. The current is conducted by the wire 260, which causes the wire to increase in temperature. The increase in temperature of the wire 260 causes the wire 260 to move from the first, extended state to the second, contracted state. In the first, extended state, the wire 260 is elongated and the actuator shaft 632 is in the first position (the valve assembly 114 is in the closed state). In the second, contracted state, the wire 260 is contracted, which overcomes the force Fs of the spring 230, and the actuator shaft 632 is in the second position (the valve assembly 114 is in the opened state). Thus, the increase in temperature of the wire 260 moves or translates the actuator shaft 632 from the first position to the second position (to open the valve assembly 114). Once the current is removed from the wire 260, the wire 260 decreases in temperature and the spring force Fs, along with the decrease in temperature, moves or translates the actuator shaft 632 from the second position to the first position (to close the valve assembly 114).

Figure 15:
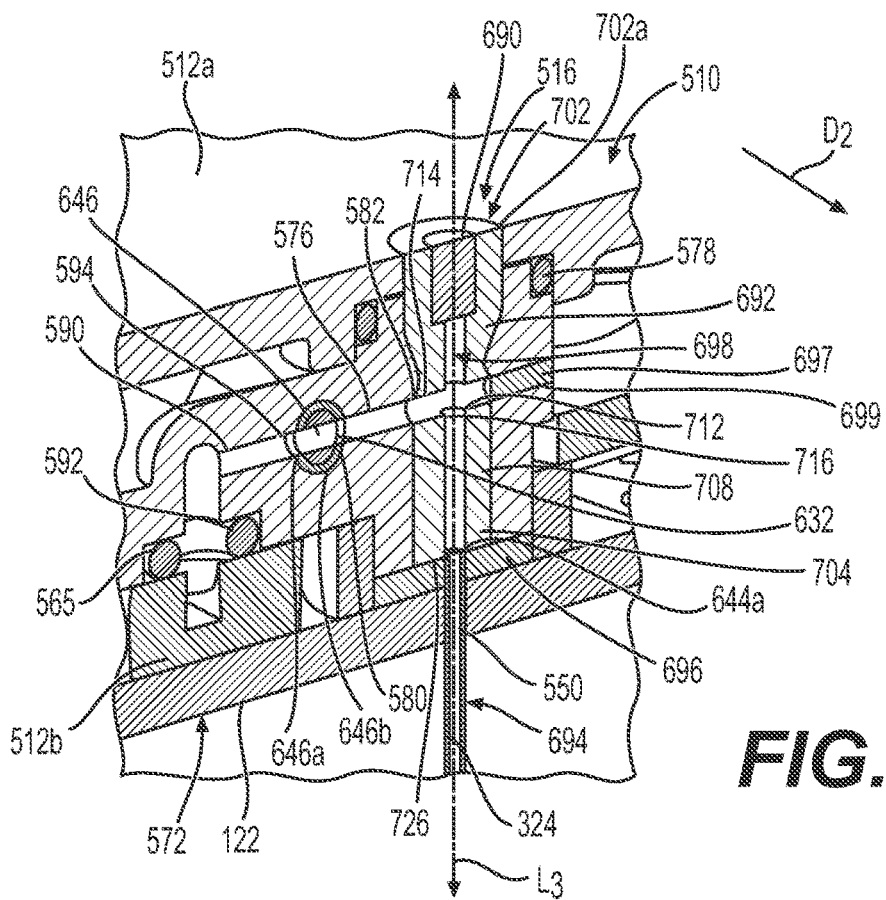
FIG. 15 is a detail view of the wearable infusion port, taken at 15 on FIG. 13, which illustrates the valve assembly in an opened state.

With reference to FIG. 15, the cannula assembly 516 is fluidly coupled to the outlet 582 of the cannula conduit 576 of the valve assembly 514 to receive the fluid or insulin. The cannula assembly 516 receives the fluid or insulin from the valve assembly 514 and delivers the fluid to the user. In one example, the cannula assembly 516 includes a needle septum 690, a cannula plug 692, a cannula 694 and a second septum 696. The needle septum 690 is positioned in a plug conduit 698 of the cannula plug 692. The needle septum 690 serves to prevent the ingress and egress of fluids into/out of the cannula plug 692. The needle septum 690 is pierceable by a piercing member of the insertion device (not shown) to couple the cannula 694 to the user.

The cannula plug 692 couples the cannula 694 to the valve housing 564. The cannula plug 692 is received through the receiving bore 530 of the first housing 510 and extends from the first housing 510 through the cannula guide 568 of the valve housing 564 to the second septum 696. The cannula plug 692 may be composed of a suitable biocompatible material, such as a polymer-based material, metal or metal alloy, which is cast, molded, printed, stamped, etc. In one example, the cannula plug 692 includes a first plug end 702 opposite a second plug end 704, a sidewall 708 and the plug conduit 698. The cannula plug 692 is substantially cylindrical, and the first plug end 702 is connected to the second plug end 704 via the sidewall 708. The first plug end 702 is coupled to the first housing 510, and may include a flange 702a that interfaces with the second surface 512a of the first housing 510. The needle septum 690 is received at the first plug end 702. The second plug end 704 is coupled to the cannula 694 and is positioned adjacent to the second septum 696. The second plug end 704 may be coupled to the cannula 694 via overmolding, ultrasonic welding, adhesives, etc. The sidewall 708 defines a cross conduit 712. The cross conduit 712 extends along an axis transverse or substantially perpendicular to a longitudinal axis L3 of the cannula assembly 516. The cross conduit 712 fluidly couples the valve housing 564 to the cannula 694. The cross conduit 712 includes a cross inlet 714 in fluid communication with the outlet 582, and a cross outlet 716 in fluid communication with the plug conduit 698. The cross conduit 712 receives the fluid or insulin from the cannula conduit 576 and directs the fluid or insulin into the plug conduit 698 for dispensing to the user through the cannula 694. In this example, the cross conduit 712 is shown to extend through the cannula plug 692 from a first side of the sidewall 708 to an opposed side of the sidewall 708, however, the cross conduit 712 may be formed from the sidewall 708 to the plug conduit 698, if desired.

The plug conduit 698 is defined within the cannula plug 692 to extend along the longitudinal axis L3 from the first plug end 702 to the second plug end 704. The plug conduit 698 receives the needle from the insertion device to couple the cannula 694 to the user, and also receives the fluid or insulin from the cross conduit 712 to deliver the fluid to the user via the cannula 694. The plug conduit 698 includes a first plug inlet 718, a second plug inlet 720 and a plug outlet 722. The needle septum 690 is coupled to the first plug inlet 718. The second plug inlet 720 is fluidly coupled to the cross outlet 716 to receive the fluid or insulin from the valve housing 564. The plug outlet 722 is fluidly coupled to a proximal end 694a of the cannula 694.

The second septum 696 is coupled or positioned between the second plug end 704 and the third surface 512b of the second housing 512. The second septum 696 is received within the second receiving projection 540 of the second housing 512. In one example, the cannula 694 passes through the second septum 696 such that the second septum 696 surrounds the cannula 694. The second septum 696 serves to prevent the ingress and egress of fluids around the cannula 694. An additional septum 697 may be coupled to a slot 699 defined in the valve housing 564 to inhibit the ingress/egress of fluid into the control system 520.

The cannula 694 is coupled to the second plug end 704 of the cannula plug 692, and is configured to be inserted into the subcutaneous tissue of a user via the insertion device (not shown). The cannula 694 is a hollow tubular structure, and includes the proximal end 694a and the distal end 324. The proximal end 694a is coupled to the second plug end 704 to couple the cannula 294 to the cannula plug 292. The proximal end 694a defines a cannula inlet 726. The cannula inlet 726 is fluidly coupled to the cannula plug 692 to receive the fluid or insulin from the valve housing 564. The distal end 324 may be blunt or pointed, and is configured to be inserted into the subcutaneous tissue of the user when the wearable infusion port 500 is coupled to the user.

Figure 17:
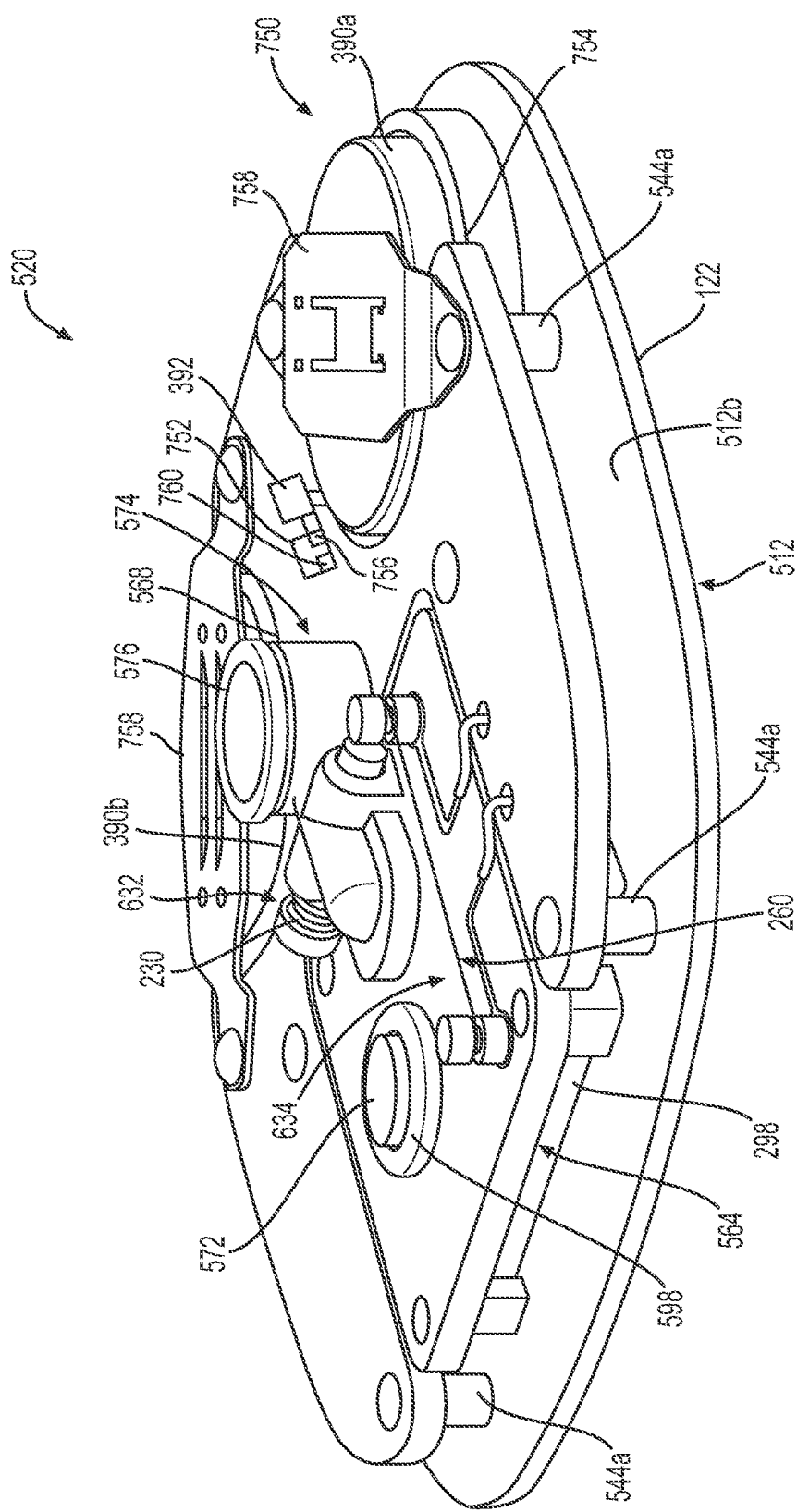
FIG. 17 is a perspective view of the wearable infusion port of FIG. 11, in which the first housing has been removed for clarity.

With reference to FIG. 17, the control system 520 includes a power supply 750, the communication device 392 and a controller 752. In one example, the power supply 750, the communication device 392 and the controller 752 are physically and electrically coupled together via a circuit board 754. The circuit board 754 may be coupled to the posts 544a to support the circuit board 754 above the third surface 512b of the second housing 512. The circuit board 754 may be electrically coupled to the flow sensor 562 via one or more electrical contacts 577 coupled to the second housing 512 (FIG. 12), however, other techniques may be employed to electrically couple the flow sensor 562 to the controller 752. The power supply 750 supplies power to the controller 752, which in turn supplies power to the wire 260, the flow sensor 562 and the communication device 392. In one example, the power supply 750 comprises the pair of coin cell batteries 390a, 390b, which are electrically coupled to the circuit board 754 via battery contact pads 758, 759 (FIG. 12). It should be noted, however, that any suitable power supply 750 may be employed with the control system 520, including, but not limited to, rechargeable batteries, solar cells, etc.

The communication device 392 enables wireless communication between the wearable infusion port 102 and the remote device or portable electronic device associated with the user, including, but not limited to a cell phone, tablet, personal computer, smart watch, smart glasses, infusion pump, etc. The communication device 392 enables the controller 752 of the wearable infusion port 500 to communicate data, such as the volume of fluid dispensed by the valve assembly 514 (as observed by the flow sensor 298), etc. The communication device 392 also enables the controller 394 to receive data, such as one or more commands for the controller 752 to dispense a volume of the fluid or insulin to the user from the portable electronic device, for example.

The controller 752 includes at least one processor 756 and a computer readable storage device or media 760. The processor 756 can be any custom made or commercially available processor, a central processing unit (CPU), a graphics processing unit (GPU), an auxiliary processor among several processors associated with the controller 752, a semiconductor based microprocessor (in the form of a microchip or chip set), a macroprocessor, any combination thereof, or generally any device for executing instructions. The computer readable storage device or media 760 may include volatile and nonvolatile storage in read-only memory (ROM), random-access memory (RAM), and keep-alive memory (KAM), for example. KAM is a persistent or non-volatile memory that may be used to store various operating variables while the processor 756 is powered down. The computer-readable storage device or media 760 may be implemented using any of a number of known memory devices such as PROMs (programmable read-only memory), EPROMs (electrically PROM), EEPROMs (electrically erasable PROM), flash memory, or any other electric, magnetic, optical, or combination memory devices capable of storing data, some of which represent executable instructions, used by the controller 752 in controlling components associated with the wearable infusion port 500.

The instructions may include one or more separate programs, each of which comprises an ordered listing of executable instructions for implementing logical functions. The instructions, when executed by the processor 756, receive and process input signals, perform logic, calculations, methods and/or algorithms for controlling the components of the wearable infusion port 500, and generate control signals to components of the wearable infusion port 500 to output one or more control signals and/or data based on the logic, calculations, methods, and/or algorithms Although only one controller 752 is shown in FIG. 17, embodiments of the wearable infusion port 500 can include any number of controllers 752 that communicate over any suitable communication medium or a combination of communication mediums and that cooperate to process the sensor signals, perform logic, calculations, methods, and/or algorithms, and generate control signals to control features of the wearable infusion port 500.

In various embodiments, one or more instructions of the controller 752 are associated with the wearable infusion port 500 and, when executed by the processor 756, the instructions receive and process signals from the flow sensor 562 and determine a volume of fluid or insulin that has been received by the valve assembly 514. In various embodiments, the instructions of the controller 752, when executed by the processor 756, output one or more control signals to the valve assembly 514 to move the valve assembly 514 from the closed state to the opened state to dispense fluid or insulin to the user based on one or more control signals received from the portable electronic device. In various embodiments, the instructions of the controller 752, when executed by the processor 756, output one or more control signals to the valve assembly 514 to move the valve assembly 514 from the opened state to the closed state based on the determined volume of the fluid or insulin received.

The adhesive patch 122 couples the wearable infusion port 102 to the user. The adhesive patch 122 is coupled to the second surface 512*a* of the second housing 512 and affixes the second housing 512, and thus, the wearable infusion port 500, to an anatomy, such as the skin of the user. The adhesive patch 122 may include the backing layer, which is removable to expose the one or more adhesive layers.

In one example, with reference to FIG. 12, in order to assemble the wearable infusion port 500, the first housing 510 and the second housing 512 may be formed. The adhesive patch 122 is coupled to the second housing 512 and the valve assembly 514 may be assembled. In one example, with reference to FIG. 14, with the valve housing 564 formed, the wire 260 may be coupled to the end 650 of the actuator shaft 632. The spring 230 is coupled about the actuator shaft 632 proximate the end 648, and the actuator shaft 632 is inserted through the actuator shaft receiving portion 584. The wire 260 is coupled to the first coupling post 656 and the second coupling post 658. The flow sensor 562 is coupled to the valve housing 564. The second septum 696 is coupled to the second housing 512. The valve housing 564 is coupled to the second housing 512.

The control system 520 is assembled by electrically and physically coupling the power supply 750, the communication device 392 and the controller 752 to the circuit board 754. The power supply 750 and the communication device 392 are each in communication with the controller 752. The circuit board 754 is coupled to the second housing 512 and the flow sensor 562 is electrically coupled to the circuit board 754. The sealing members 598, 578 are coupled to the valve housing 564. The first housing 510 is coupled to the second housing 512. With reference to FIG. 15, with the cannula plug 692 formed, the cannula 694 is coupled to the cannula plug 692. The needle septum 690 is coupled to the plug conduit 698, and the cannula assembly 116 is inserted into the first housing 510 and the valve housing 564 such that the second plug end 704 is coupled to the needle septum 690.

With the wearable infusion port 500 assembled, the wearable infusion port 500 may be packaged, sterilized and provided to an end user. Once received, the user may remove the packaging to expose the wearable infusion port 500. The user may remove the backing layer, if any, from the adhesive patch 122. The user may manipulate the insertion device (not shown) to deploy the wearable infusion port 500 onto the user such that the distal end 324 of the cannula 694 is positioned within the subcutaneous tissue of the user. The adhesive patch 122 couples the wearable infusion port 500 to the anatomy, such as the skin, of the user.

With the wearable infusion port 500 coupled to the user, with reference to FIG. 4, the user may dispense the fluid or insulin F into the first needle port 532. The fluid F flows from the first needle port 532 into the port conduit 600 of the valve housing 564. From the port conduit 600, the fluid F flows into the sensor inlet 563 of the flow sensor 562. The fluid F is heated by the heater 328, and the temperature sensors 329*a*, 329*b* observe the temperature of the fluid F. The fluid F flows into the sensor outlet 565 and from the sensor outlet 565 the fluid flows into the first shaft conduit 590. With reference to FIG. 16, the valve assembly 514 is shown in the closed state. In the closed state, the second shaft conduit 646 defined in the actuator shaft 632 is not aligned or is not fluidly coupled to the first shaft conduit 590, and thus, the fluid received from the first needle port 532 cannot flow through the cannula 694. Based on the receipt of the one or more control signals (or power) from the control system 520, with reference to FIG. 14, the wire 260 begins to increase in temperature, which causes the wire 260 to contract or move toward the second coupling post 658. The contraction of the wire 260 overcomes the spring force Fs and causes the actuator shaft 632 to move or translate linearly toward the second position in the direction D2 toward the second coupling post 658. With reference to FIG. 15, the translation of the actuator shaft 632 moves the second shaft conduit 646 into alignment with the first shaft conduit 590 such that the first shaft conduit 590 is fluidly coupled to the second shaft conduit 646 to enable the fluid F to flow through the actuator shaft 632 and into the cannula conduit 576. In FIG. 15, the valve assembly 514 is in the opened state. From the cannula conduit 576, the fluid F flows into the cross conduit 712, and from the cross conduit 712 into the plug conduit 698. From the plug conduit 698 the fluid F flows into the cannula 694 and into the subcutaneous tissue of the user.

The flow sensor 562 observes the fluid F that flows into the wearable infusion port 500, and the processor 756 of the controller 752 determines the volume of fluid received through the first needle port 532 based on the sensor signals from the flow sensor 298. Based on the volume of fluid F, the processor 756 of the controller 752 outputs one or more control signals (removes the power) to the wire 260. With the power removed, the wire 260 cools. As the wire 260 cools, the spring force Fs of the spring 230 (FIG. 14) moves or translates the actuator shaft 632 back to the first position (as shown in FIG. 16). The movement or translation of the actuator shaft 632 moves the second shaft conduit 646 out of alignment with the first shaft conduit 590, and thereby inhibits fluid communication between the valve housing 564 and the cannula 694.

Once coupled to the user, the control system 520 of the wearable infusion port 102 communicates with the portable electronic device and may send one or more notifications to the portable electronic device for display on the portable electronic device, including, but not limited to, a volume of insulin dispensed, etc. In addition, the control system 520 may also be able to determine when the wearable infusion port 500 is low or needs an additional quantity of insulin. For example, the inlet port 572 of the valve housing 564 may serve as a fluid reservoir, which may hold more fluid or insulin than necessary for a single dose. The processor 756 of the control system 520 may be configured to determine, based on the sensor signals from the flow sensor 562 and a known quantity of fluid or insulin that may be contained in the inlet port 572 of the valve housing 564, a quantity or volume of the fluid or insulin remaining within the reservoir defined by the inlet port 572. Based on this determination, the control system 520 may be configured to output one or more notifications to the user to dispense additional quantities of fluid into the wearable infusion port 500. Generally, once coupled to the user, the wearable infusion port 500 may be worn by the user for about 7 to about 10 days.

Thus, the wearable infusion port 500 enables a user to infuse a fluid, such as insulin, into the subcutaneous tissue of the user over an extended period of time without requiring the user to directly inject the fluid into the anatomy of the user. This greatly reduces the number of times the user has to insert a needle or pierced tip instrument into their anatomy, while providing the user with the necessary infusion therapy. For users who require multiple injections of fluid or insulin a day, the user is subjected to a single insertion of the wearable infusion port 500 instead of multiple insertions with needle syringes, etc. The remote device may communicate with the control system 120 of the wearable infusion port 500 to control the wearable infusion port 500 to dispense the insulin. This can provide the user with an experience similar to that provided by an infusion pump, with a smaller form factor. In addition, the use of the flow sensor 562 with the wearable infusion port 500 may detect occlusions of the wearable infusion port 500 (via a volume of fluid flow observed) and also ensures the delivery of the proper amount.

The pump 104 may be used with either one the wearable infusion port 102 and the wearable infusion port 500 to provide fluid, such as insulin, to the respective one of the wearable infusion port 102 and the wearable infusion port 500. It should be noted that the pump 104 may be used to provide fluid, such as insulin, to various other ports associated with medical devices, and thus, the use of the pump 104 with the wearable infusion port 102 and the wearable infusion port 500 is merely an example. In this example, the pump 104 is substantially circular; however, the pump 104 may have any desired shape. In one example, with reference to FIG. 18, the pump 104 includes a first pump housing 800, a plunger assembly 802, a biasing member or torsion spring 804 and a lock system 806. The torsion spring 804 and the lock system 806 cooperate to define an actuator system 809 for the pump 104. Although not illustrated herein, it should be understood that in certain embodiments, the pump 104 may also include a cap, cover, plug or the like, which cooperates with the first pump housing 800 to enclose the plunger assembly 802, the torsion spring 804 and the lock system 806, without obstructing the operation of a cannula assembly 834, described below.

The first pump housing 800 may be composed of a suitable biocompatible material, including, but not limited to a biocompatible polymer-based material, which may be molded, printed, cast, etc. The first pump housing 800 is substantially circular, however, the first pump housing 800 may have any desired shape. The first pump housing 800 is coupled to the plunger assembly 802, the torsion spring 804 and the lock system 806. In one example, the first pump housing 800 defines at least one fluid reservoir 810 and an actuator chamber 812. In this example, the first pump housing 800 defines a plurality of fluid reservoirs, which in this example is two fluid reservoirs 810a, 810b; however, the first pump housing 800 may have any number of fluid reservoirs 810. The fluid reservoirs 810a, 810b are spaced apart about a perimeter or circumference of the first pump housing 800, and in this example are about 180 degrees apart along the circumference of the first pump housing 800. Thus, in this example, the fluid reservoirs 810a, 810b are on opposed sides of the first pump housing 800. The fluid reservoirs 810a, 810b, in this example, are integrally formed with and fixed to the first pump housing 800, and are not removable or replaceable.

Figure 19:
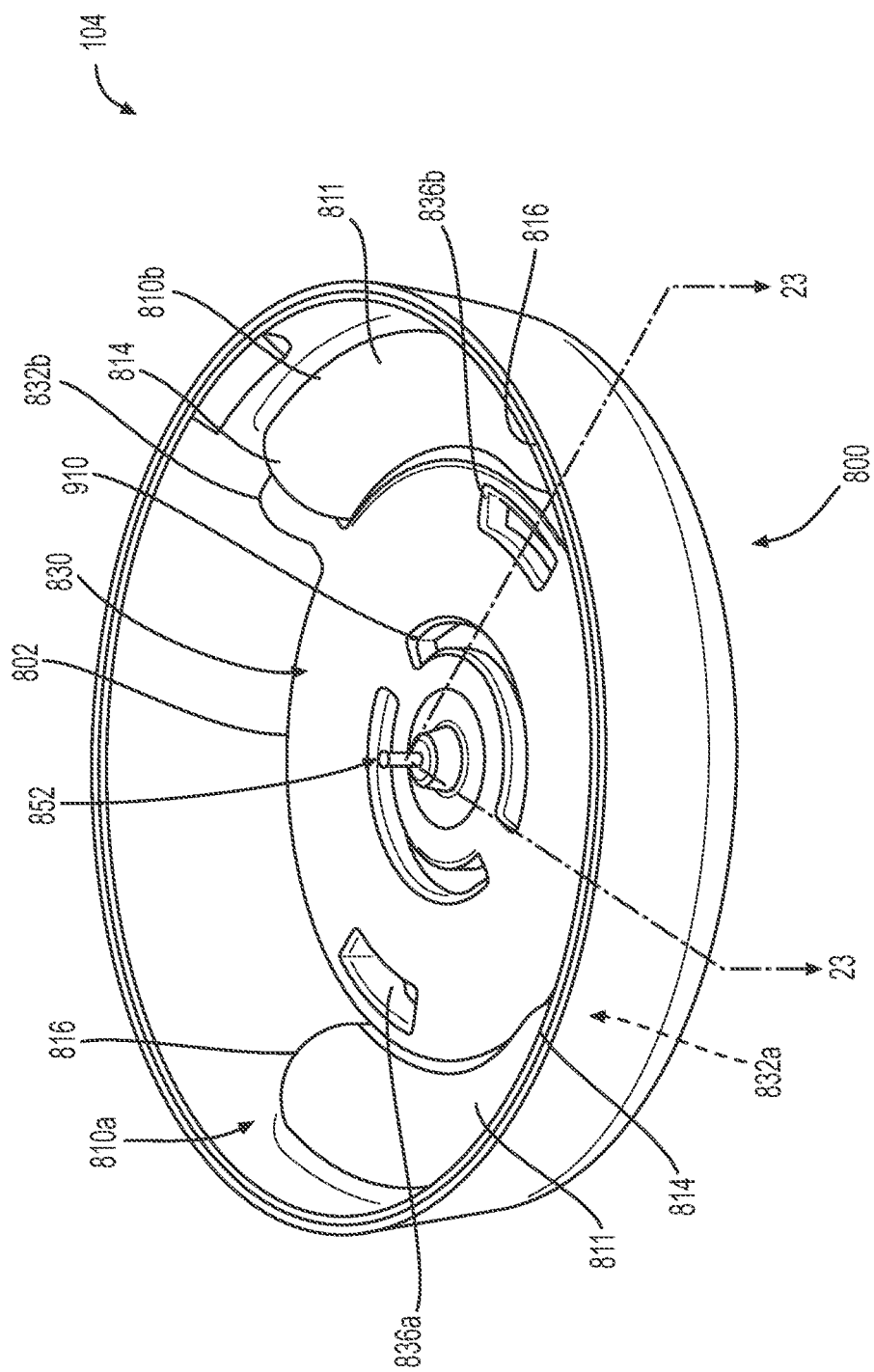
FIG. 19 is a bottom view of the pump of FIG. 1 in accordance with various embodiments.
Figure 22:
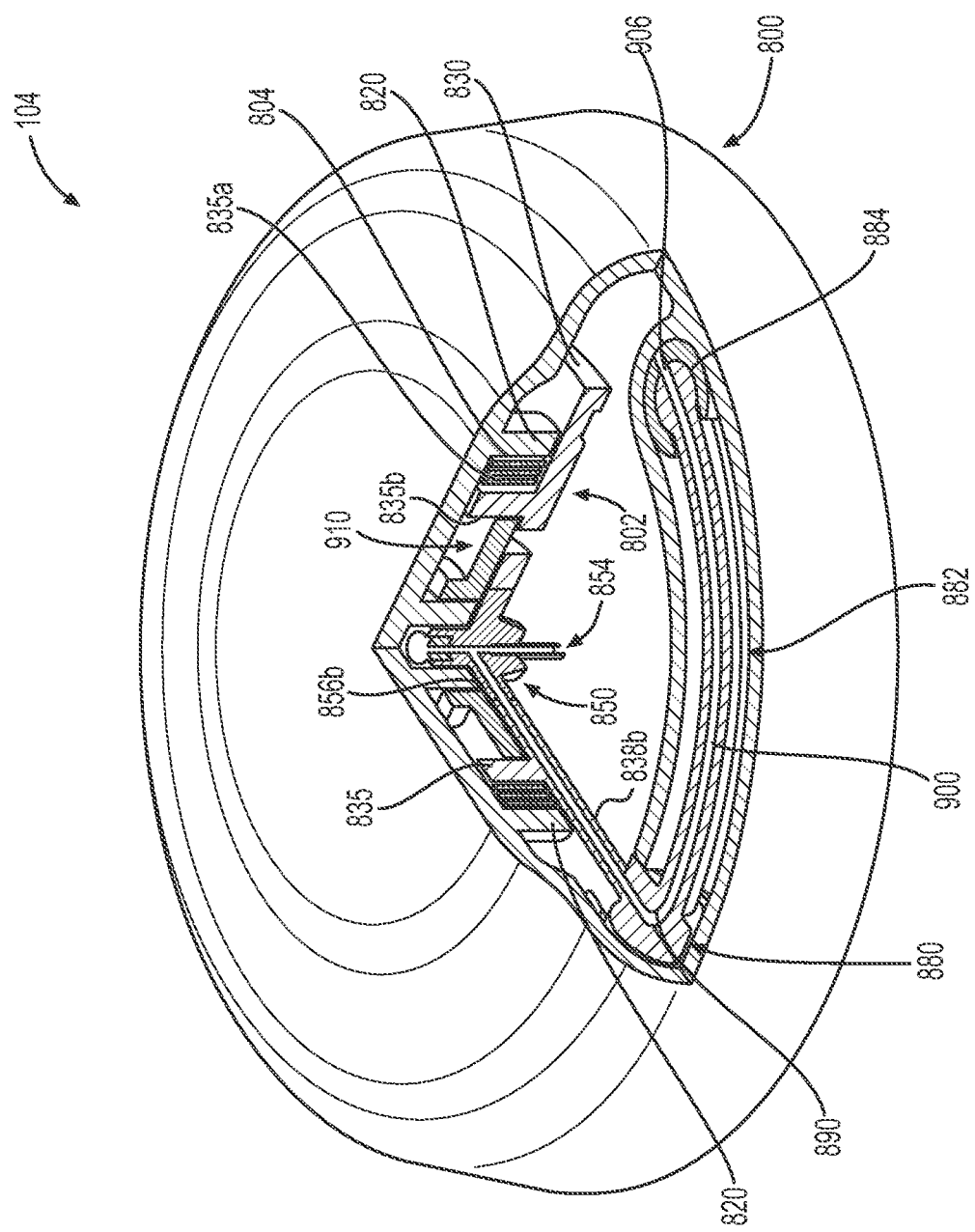
FIG. 22 is a partially cross-sectional view of the pump, taken along line 21-21 of FIG. 1, which illustrates the plunger assembly advanced to a second reservoir end of the fluid reservoir associated with the pump to empty the fluid from the fluid reservoir.

With reference to FIG. 19, each of the fluid reservoirs 810a, 810b include a first reservoir end 814 and a second reservoir end 816 opposite the first reservoir end 814. The first reservoir end 814 is circumferentially open to receive a portion of the plunger assembly 802 therethrough. The second reservoir end 816 is circumferentially closed (FIG. 22). The fluid, such as insulin, is contained within each of the fluid reservoirs 810a, 810b in a fluid chamber 811 that is defined by each of the fluid reservoirs 810a, 810b between the first reservoir end 814 and the second reservoir end 816. As will be discussed, the plunger assembly 802 is received within each of the fluid reservoirs 810a, 810b, and is movable within the fluid reservoirs 810a, 810b to dispense the fluid from the pump 104. In this example, the first reservoir end 814 of the fluid reservoir 810b is aligned with or faces the second reservoir end 816 of the fluid reservoir 810a about the circumference of the first pump housing 800, and the first reservoir end 814 of the fluid reservoir 810a is aligned with or faces the second reservoir end 816 of the fluid reservoir 810b. By positioning the first reservoir ends 814 in opposed directions about the perimeter of the first pump housing 800, the plunger assembly 802 is able to move in a single direction and dispense fluid from each of the fluid reservoirs 810a, 810b, as will be discussed herein. Generally, the fluid reservoirs 810a, 810b are pre-filled with the fluid or insulin and are not refillable such that the pump 104 is a disposable, consumable component.

Figure 18:
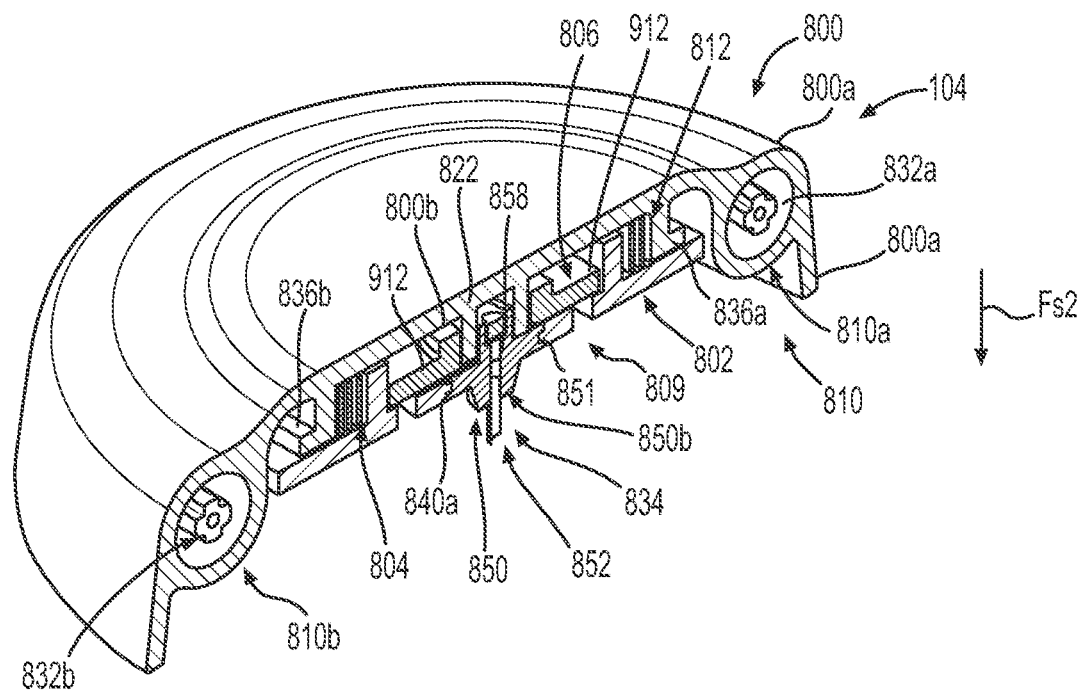
FIG. 18 is a cross-sectional view of the wearable infusion port and the pump of FIG. 1, which is taken along line 18-18 of FIG. 1.
Figure 18:
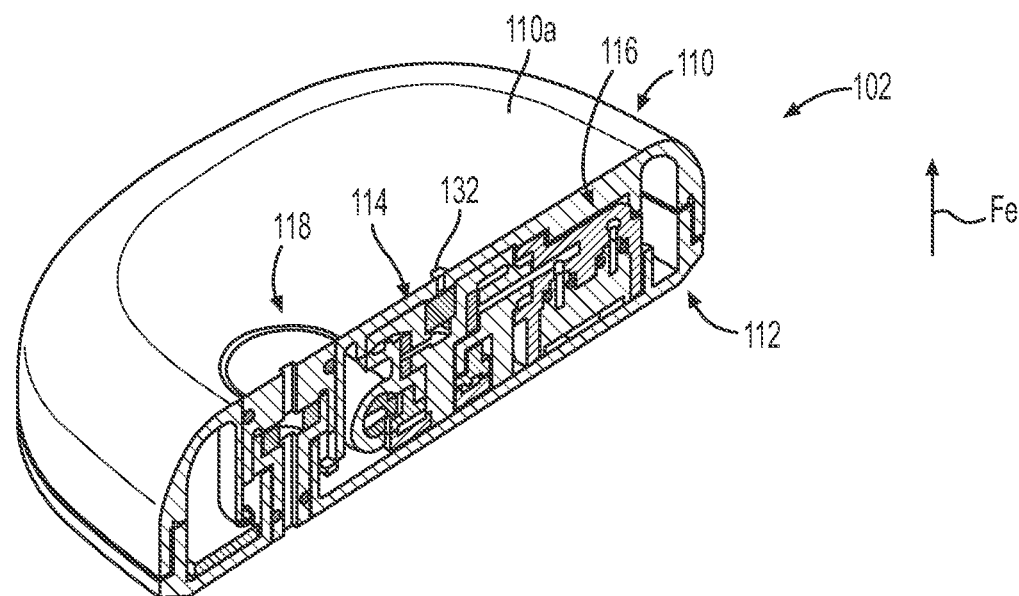

With to FIG. 18, the actuator chamber 812 includes a central post 818 and a retaining flange 820. The central post 818 receives a portion of the plunger assembly 802. In this example, the central post 818 includes one or more keyed projections 822, which cooperate with corresponding keyed grooves 824 on a portion of the lock system 806 to couple the lock system 806 to the central post 818. The keyed projections 822 and the keyed grooves 824 inhibit a rotation of the lock system 806 relative to the first pump housing 800. The keyed projections 822 and the keyed grooves 824 also direct a translational movement of the lock system 806 relative to the first pump housing 800 as will be discussed further herein. The retaining flange 820 couples the plunger assembly 802 to the first pump housing 800. In one example, the retaining flange 820 includes opposed lips 826, which cooperate with the plunger assembly 802 to guide a rotation of the plunger assembly 802 relative to the first pump housing 800.

The plunger assembly 802 is movable or rotatable relative to the first pump housing 800 to dispense fluid substantially simultaneously from each of the fluid reservoirs 810a, 810b. In one example, the plunger assembly 802 includes a plunger base 830 and at least one plunger arm 832. In this example, the plunger assembly 802 includes a plurality of plunger arms, which in this case is two plunger arms 832a, 832b. It should be noted, however, that the plunger assembly 802 may include any number of plunger arms 832 that correspond with the number of fluid reservoirs 810. The plunger base 830 and the plunger arms 832a, 832b may be composed of a suitable biocompatible material, including, but not limited to a biocompatible polymer-based material, which may be molded, printed, cast, etc. The plunger arms 832a, 832b may be separately or integrally formed with the plunger base 830. A side view of the plunger assembly 802 is shown in FIG. 20B.

Figure 20:
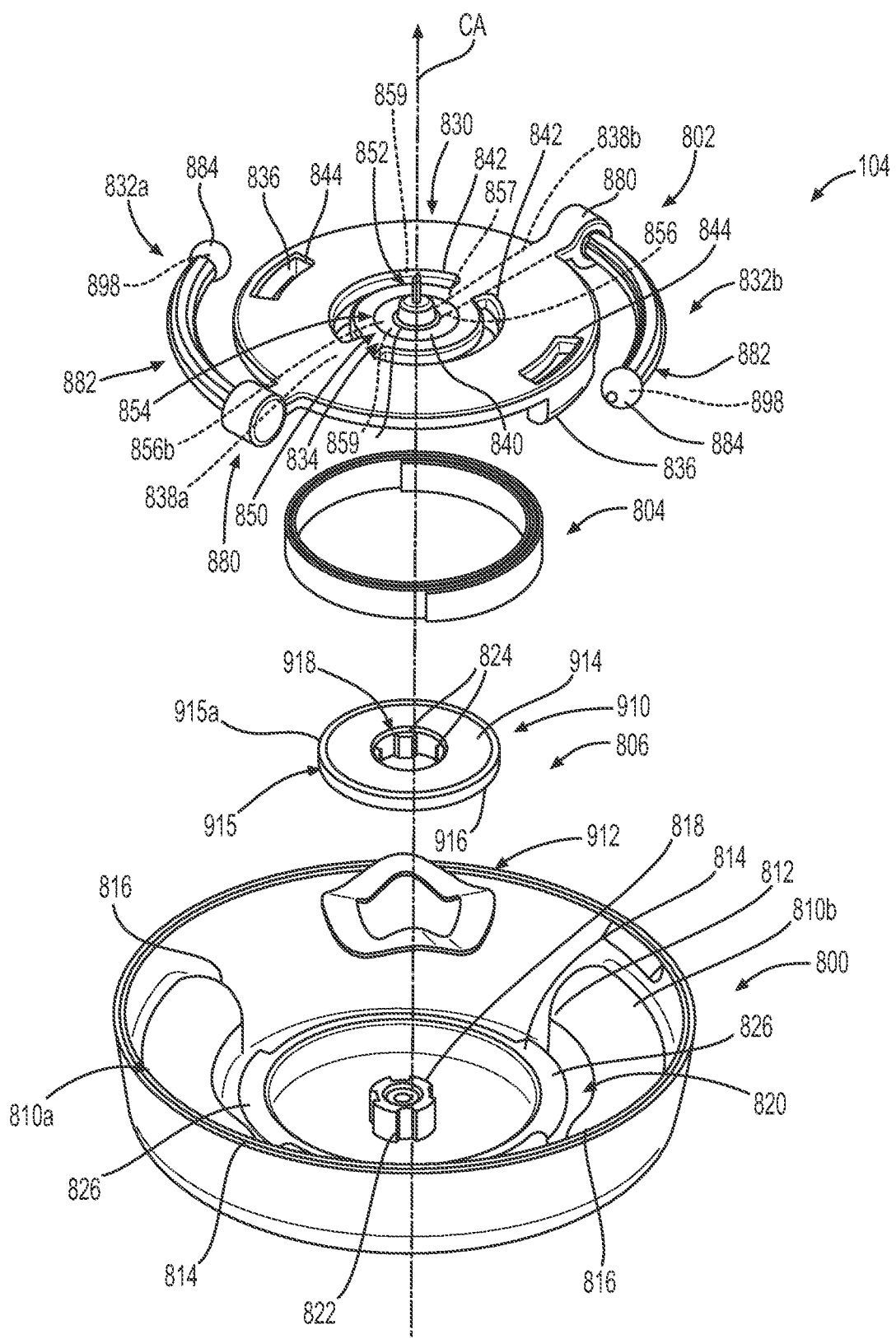
FIG. 20 is an exploded view of the pump.
Figure 20A:
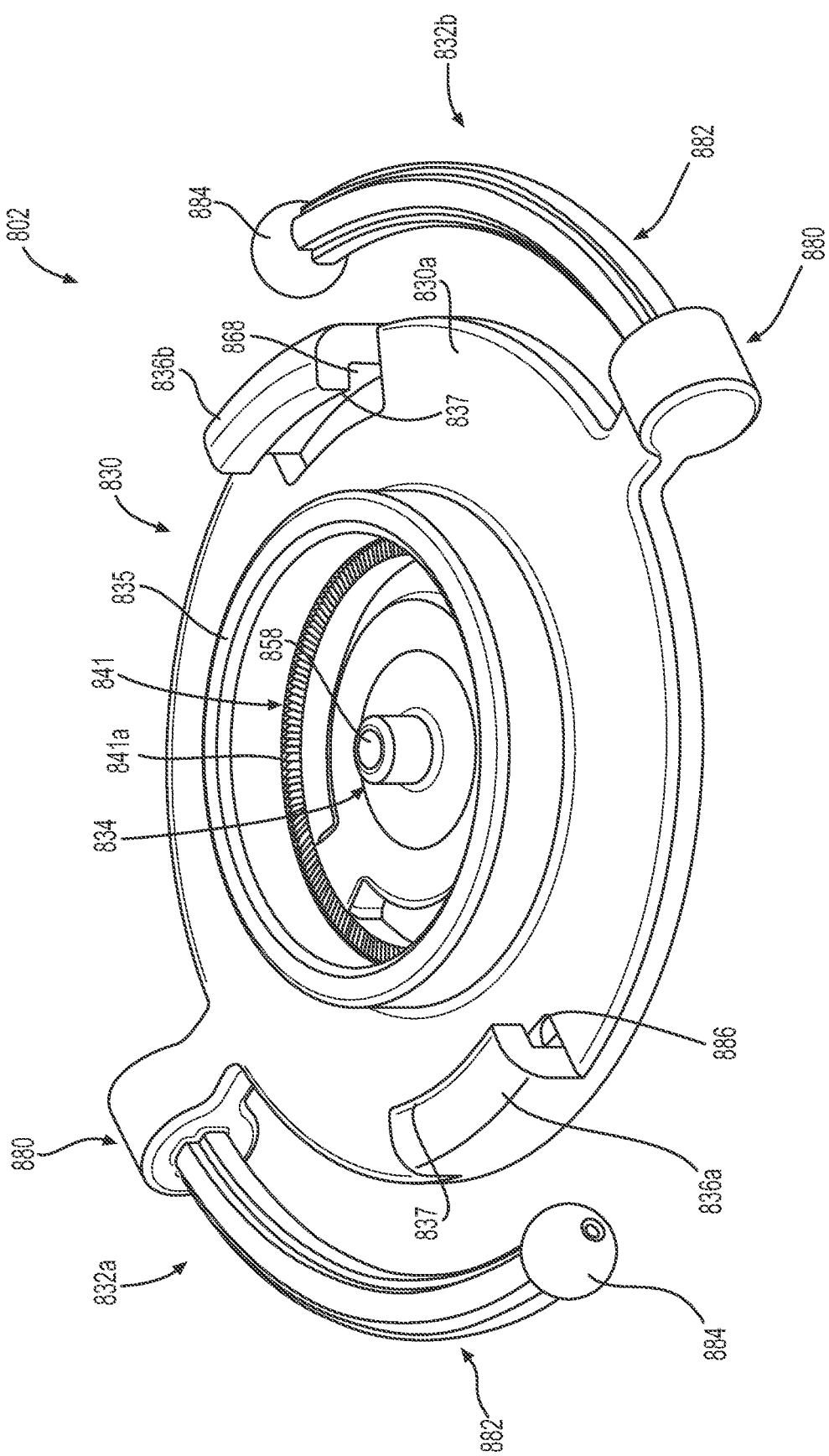
FIG. 20A is a top perspective view of a plunger assembly associated with the pump.
Figure 21:
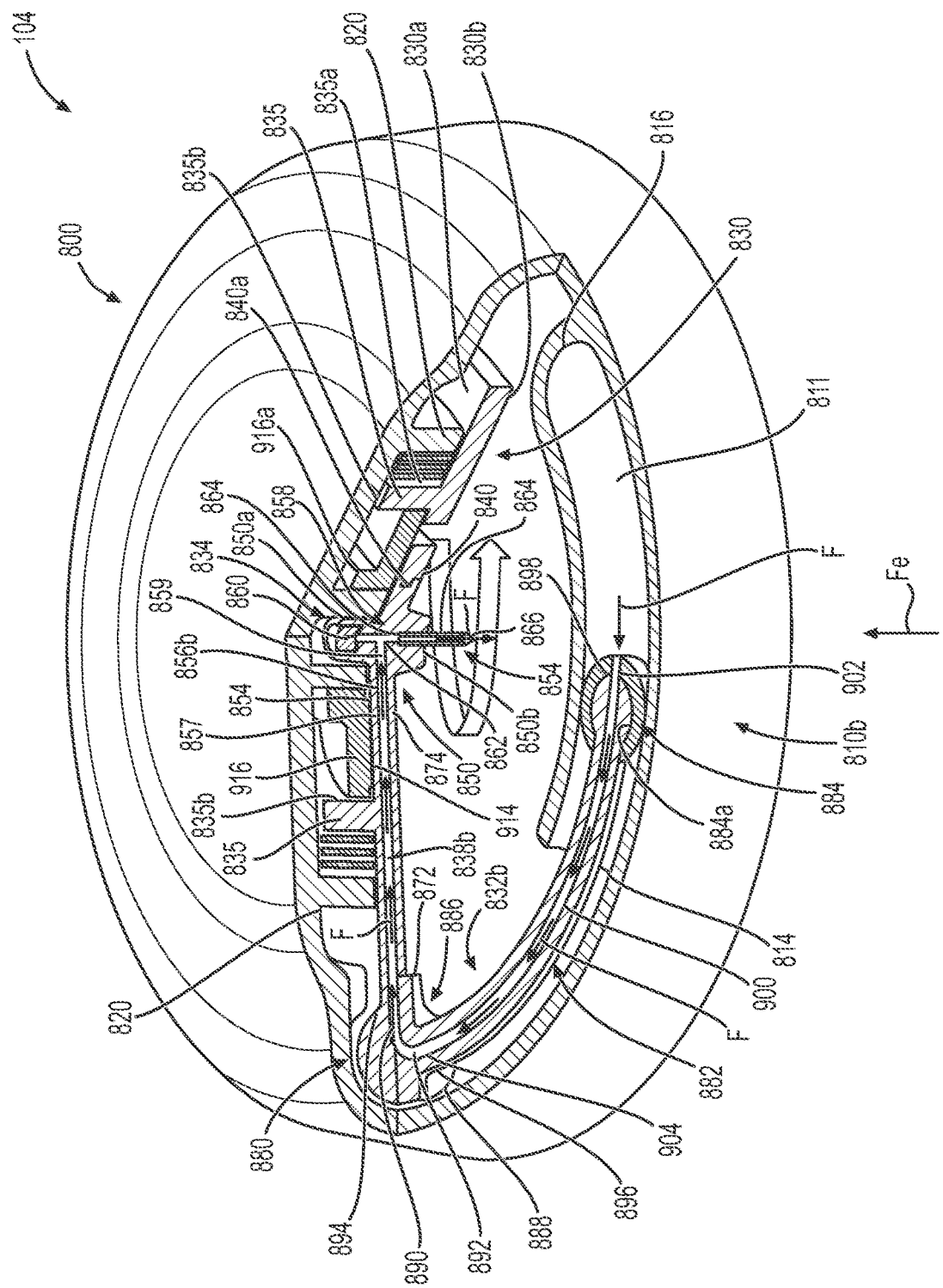
FIG. 21 is a partially cross-sectional view of the pump, taken along line 21-21 of FIG. 1, which illustrates an advancement of a plunger assembly within a fluid reservoir associated with the pump.

In this example, the plunger base 830 is circular, however the plunger base 830 may have any shape that corresponds to the shape of the first pump housing 800. In one example, the plunger base 830 includes the cannula assembly 834, at least one guide flange 836 and a base conduit 838 (FIG. 21). The cannula assembly 834 is received within a central bore 840 defined through the plunger base 830. The plunger base 830 and the cannula assembly 834 may be composed of a suitable biocompatible material, including, but not limited to a biocompatible polymer-based material, which may be molded, printed, cast, etc. The cannula assembly 834 may be coupled to the plunger base 830 via overmolding, adhesives, ultrasonic welding, laser welding, press-fit, etc. The central bore 840 extends along a central axis CA of the pump 104. The central bore 840 defines a notch 840a (FIG. 18), which assists in coupling the cannula assembly 834 to the plunger base 830. In one example, the plunger base 830 also defines a pair of cut-outs 842 about a portion of a perimeter or circumference of the central bore 840 and a plunger lock surface 841 (FIG. 20A). The cut-outs 842 provide a mass savings, and are substantially crescent-shaped. The cut-outs 842 are defined to extend about the central bore 840 from either side of the base conduit 838 (FIG. 21). With reference to FIG. 20A, the plunger lock surface 841 is defined proximate the cut-outs 842, and is defined to extend about a perimeter or a circumference of an area adjacent to an annular flange 835. In one example, the plunger lock surface 841 includes a plurality of teeth 841a, which cooperate to engage with a corresponding plurality of teeth 915a defined on the lock plate 910. The engagement between the teeth 841a, 915a maintains the plunger assembly 802 in the second, locked position. The annular flange 835 extends outwardly from the plunger base 830, and surrounds the cannula assembly 834. The annular flange 835 is sized and shaped to receive the lock plate 910. A first side 835a of the annular flange 835 is selectively coupled to the torsion spring 804 via the lock system 806, and a second side 835b of the annular flange 835 (opposite the first side 868) is proximate the lock system 806. The plunger base 830 also defines a second pair of cut-outs 844. The second pair of cut-outs 844 are substantially rectangular, and are defined through the plunger base 830 proximate the at least one guide flange 836.

The cannula assembly 834 is configured to be coupled to the wearable infusion port 102, 500 to transfer the fluid received from the fluid reservoirs 810a, 810b to the wearable infusion port 102, 500. In one example, the cannula assembly 834 includes a cannula coupling portion 850 and a cannula 852. The cannula coupling portion 850 is substantially cylindrical, and defines a coupling flange 854, a conduit 856 (FIG. 21) and a central cannula bore 858 (FIG. 21). The cannula coupling portion 850 has a first end 850a and an opposed second end 850b. The first end 850a and the second end 850b each extend a distance beyond a respective surface of the plunger base 830. The second end 850b generally extends the distance beyond the surface of the plunger base 830 to receive an external force Fe. With reference to FIG. 21, the coupling flange 854 is defined about a perimeter or circumference of the cannula coupling portion 850 and in one example, includes a groove 851. The groove 851 is configured to form an interference fit with the corresponding notch 840a defined in the central bore 840. The interference fit also forms a seal between the plunger base 830 and the cannula assembly 834. The conduit 856 is defined through the coupling flange 854 to fluidly couple the cannula 852 to the base conduit 838. The conduit 856 is defined along an axis that is transverse or substantially perpendicular to the central axis CA. In one example, with brief reference to FIG. 20, the conduit 856 includes a branch 856a defined through the coupling flange 854 at a first end to extend to the central cannula bore 858, and a branch 856b defined through the coupling flange 854 at an opposed second end to extend to the central cannula bore 858. It should be noted that the number of branches 856a, 856b of the conduit 856 may be based on the number of plunger arms 832, and thus, the use of two branches 856a, 856b is merely an example. Each of the branches 856a, 856b includes a branch inlet 857 in fluid communication with the respective base branches 838a, 838b, and a branch outlet 859 in fluid communication with the central cannula bore 858.

The central cannula bore 858 is defined through the cannula coupling portion 850 along the central axis CA. The central cannula bore 858 fluidly couples the cannula 852 to the conduit 856. The central cannula bore 858 is defined through the cannula coupling portion 850 from the first end 850*a* to the second end 850*b*. With reference to FIG. 21, the central cannula bore 858 includes a septum 860 received proximate the first end 850*a*, which serves to prevent the ingress and egress of fluids into/out of the central cannula bore 858. The central cannula bore 858 has a pair of inlets 862 defined between the first end 850*a* and the second end 850*b*. Each of the inlets 862 receives the fluid from the respective branch outlet 859 of the branches 856*a*, 856*b*, and directs the fluid from the branches 856*a*, 856*b* into the cannula 852.

The cannula 852 is received within the second end 850*b* of the cannula coupling portion 850. The cannula 852 is cylindrical and hollow, has a proximal end 864 and an opposite distal end 866. The proximal end 864 is fluidly coupled to the inlets 862. The distal end 866 may be blunt or pointed, and is configured to be inserted into the first needle port 132 of the wearable infusion port 102 or the first needle port 532 of the wearable infusion port 500 to deliver the fluid to the respective wearable infusion port 102, 500.

The at least one guide flange 836 is defined on the plunger base 830 on a first surface 830*a* of the plunger base 830, and the first surface 830*a* is opposite a second surface 830*b*. In this example, with reference to FIG. 20A, the at least one guide flange 836 comprises two guide flanges 836*a*, 836*b*, which are spaced apart about a perimeter or circumference of the plunger base 830. The guide flanges 836*a*, 836*b* project outwardly from the first surface 830*a*, and define a lip 837. The lip 837 of the first side 868 of each of the guide flanges 836*a*, 836*b* is coupled to a respective one of the lips 826 of the retaining flange 820 when the plunger assembly 802 is in a first, unlocked position and engaged with the torsion spring 804. The lip 837 of the first side 868 of the guide flanges 836*a*, 836*b* is unengaged with or spaced apart from the retaining flange 820 when the plunger assembly 802 is in the second, locked position. With reference back to FIG. 21, the engagement of the lip 837 of the first side 868 of each of the guide flanges 836*a*, 836*b* with the retaining flange 820 guides a movement or rotation of the plunger base 830 relative to the first pump housing 800.

Figure 20C:
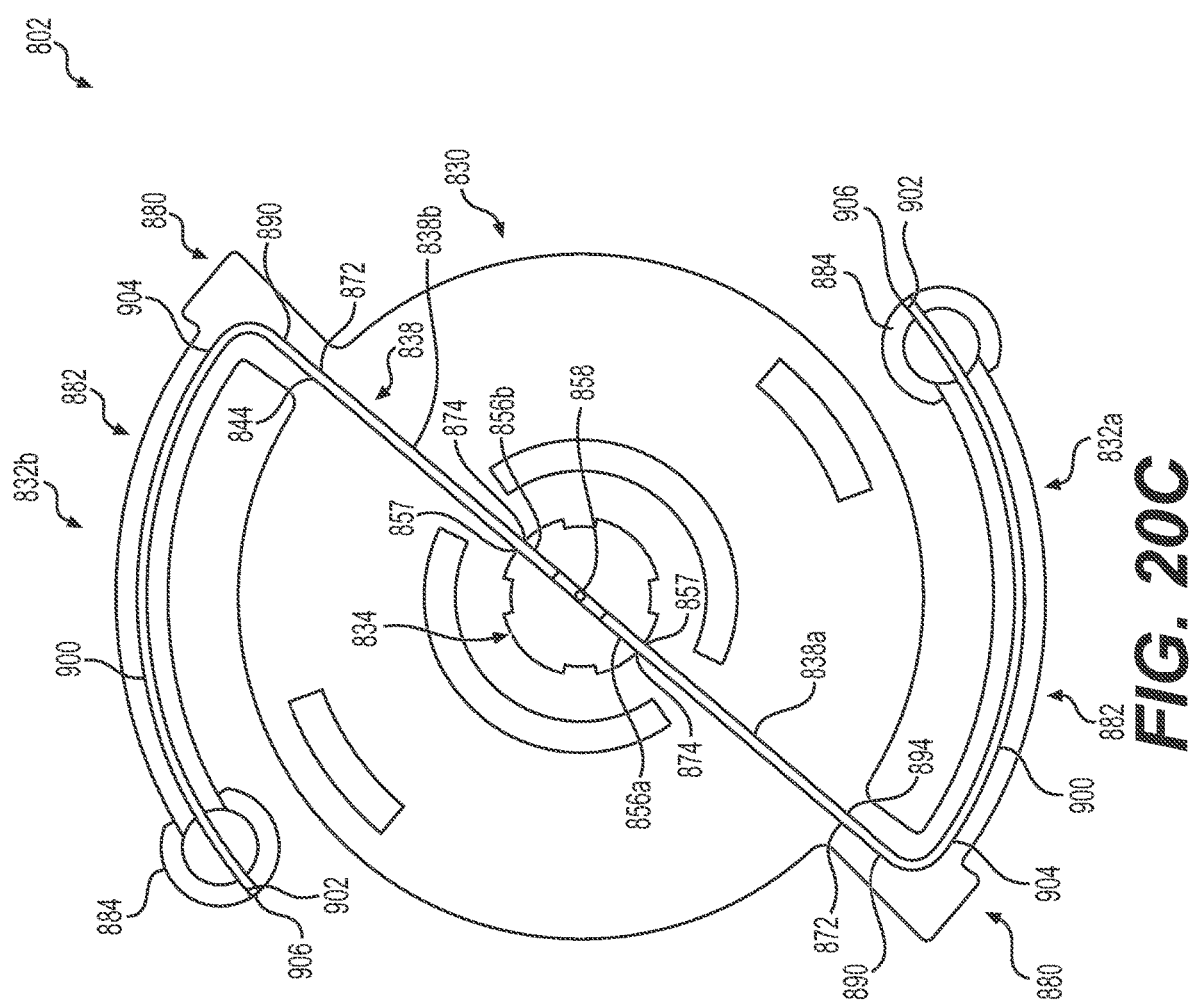
FIG. 20C is a cross-sectional view of the plunger assembly, taken along line 20C-20C of FIG. 20B, which illustrates conduits associated with the plunger assembly.

The base conduit 838 is defined from the respective one of the plunger arms 832*a*, 832*b*, and extends from the respective one of the plunger arms 832*a*, 832*b* to the respective one of the branches 856*a*, 856*b* of the central cannula bore 858 to fluidly couple the plunger arms 832*a*, 832*b* to the cannula 852 (FIG. 20C). Thus, in this example, the base conduit 838 includes two base branches 838*a*, 838*b* (FIG. 20C). It should be noted that the number of base branches 838*a*, 838*b* is directly proportional to the number of plunger arms 832 to enable fluid communication between the plunger arms 832 and the cannula 852. Each of the base branches 838*a*, 838*b* include a base inlet 872 in fluid communication with the respective plunger arm 832*a*, 832*b*, and a base outlet 874 in fluid communication with the respective branch inlet 857 of the branches 856*a*, 856*b* of the cannula coupling portion 850 to receive the fluid from the plunger arms 832*a*, 832*b* and deliver the fluid to the cannula 852.

With reference to FIG. 20, the plunger arms 832*a*, 832*b* are on opposed sides of the plunger base 830, and are coupled to the plunger base 830 at a perimeter or circumference of the plunger base 830. In contrast, the cannula 852 is coupled proximate or at a center of the plunger base 830. Each of the plunger arms 832*a*, 832*b* include a base connector 880, a plunger body 882 and a plunger 884. In this example, the plunger arms 832*a*, 832*b* are coupled to the plunger base 830 with the base connectors 880 such that the base connector 880 of the plunger arm 832*a* faces the plunger 884 of the plunger arm 832*b*. Thus, the plunger arms 832 are asymmetric with respect to the central axis CA. Each of the base connectors 880 couple the plunger arms 832*a*, 832*b* to the plunger base 830, and fluidly couple the plunger arms 832*a*, 832*b* to the respective one of the base branches 838*a*, 838*b*. Each of the base connectors 880 include a connector 886 and a cylindrical cap 888. The connector 886 couples each of the plunger arms 832*a*, 832*b* physically and fluidly to the plunger base 830. Each connector 886 includes a connector conduit 890, which is in fluid communication with the respective one of the base branches 838*a*, 838*b* (FIG. 20C). Each connector conduit 890 includes an inlet 892 in fluid communication with the respective plunger body 882, and an outlet 894 in fluid communication with a respective base inlet 872 of the base branches 838*a*, 838*b*. The connector conduit 890 may be substantially L-shaped to direct the fluid from the plunger body 882 to the base branches 838*a*, 838*b*. The caps 888 are each configured to enclose the fluid reservoirs 810*a*, 810*b* when the plunger arms 832*a*, 832*b* are fully received within the respective one of the fluid reservoirs 810*a*, 810*b*. Each cap 888 has a diameter, which is different, and in this example, greater than a diameter of the plunger body 882.

The plunger body 882 extends between the base connector 880 and the plunger 884. In this example, the plunger body 882 is arcuate to follow the curvature of the fluid reservoirs 810*a*, 810*b*; however, the plunger body 882 may have any desired shape that corresponds with the fluid reservoirs 810*a*, 810*b*. For example, the plunger body 882 is substantially cross-shaped in cross-section, however, the plunger body 882 may have any desired cross-sectional shape, including circular, square, rectangular, etc. The plunger body 882 has a diameter that is different, and in this example, less than a diameter of the cap 888. Each of the plunger bodies 882 have a first end 896 opposite a second end 898, and define a body conduit 900 from the first end 896 to the second end 898. The first end 896 is coupled to the base connector 880, and the second end 898 is coupled to the plunger 884. The plunger bodies 882 are cantilevered relative to the base connectors 880. The second end 898 of the plunger bodies 882 may be bulbous to receive the plunger 884. Generally, each second end 898 has a diameter, which is different, and in this example, greater than the diameter of the plunger body 882.

Each of the body conduits 900 direct the fluid out of the respective fluid reservoir 810*a*, 810*b* into the plunger base 830, and thus, the cannula 852 (FIG. 20C). Each body conduit 900 includes an inlet 902 and an outlet 904. The inlet 902 is fluidly coupled to the respective plunger 884 to receive the fluid from the fluid reservoir 810*a*, 810*b*. The outlet 904 is fluidly coupled to the inlet 892 of the base connector 880 to direct the fluid from the fluid reservoirs 810*a*, 810*b* to the base branches 838*a*, 838*b*.

Each plunger 884 surrounds the second end 898 of the respective plunger body 882. The plunger 884 is substantially spherical, and defines a central chamber 884*a*, which enables the plunger 884 to be received about the second end 898 to enclose the second end 898. Each plunger 884 defines an inlet 906, which receives the fluid from the respective fluid reservoir 810*a*, 810*b*. The inlet 906 is fluidly coupled to the inlet 902 of the respective plunger body 882 to direct the fluid from the respective fluid reservoir 810*a*, 810*b* through the plunger assembly 802 and into the cannula 852 (FIG. 20C). Each plunger 884 may be composed of a biocompatible polymer-based material, which may be cast, molded, etc. and coupled to the second end 898. The plunger 884 may also be overmolded onto the second end 898 of the respective plunger body 882, or may be integrally formed with the respective plunger body 882. The plunger 884 is generally sized to have a diameter, which is about the same as the diameter of the respective fluid reservoir 810a, 810b so that the plungers 884 form a seal along the side of the fluid reservoir 810a, 810b. The seal formed by the plungers 884 within the respective fluid reservoir 810a, 810b ensures that the fluid is dispensed from the fluid reservoirs 810a, 810b via the inlet 906, and inhibits leaking of the fluid about the plunger 884. Further, the seal formed by the plungers 884 results in an increase in pressure within the fluid reservoirs 810a, 810b as the plunger arms 832a, 832b advance within the fluid reservoirs 810a, 810b, which assists in the dispensing of the fluid from the fluid reservoirs 810a, 810b into the plunger assembly 802, and thus, the cannula 852.

The torsion spring 804 is coupled between the retaining flange 820 of the first pump housing 800 and the annular flange 835 of the plunger base 830 (FIG. 21). The torsion spring 804 is composed of a metal or metal alloy, such as a spring steel, and may be shaped to form the torsion spring 804. When the plunger assembly 802 is in the first, unlocked position, the torsion spring 804 applies a torque about the central axis CA to a first side 835a of the annular flange 835 to move or rotate the plunger base 830, and thus, the plunger arms 832 relative to the first pump housing 800 to dispense the fluid. Thus, the torsion spring 804 moves the plunger assembly 802 in a first direction, which in this example is counterclockwise, to dispense the fluid from the fluid reservoirs 810a, 810b. When the first side 835a of the annular flange 835 is spaced apart from the torsion spring 804 by the lock system 806, the plunger arms 832 are inhibited from moving to dispense the fluid. The advancement of the plunger arms 832a, 832b within the fluid reservoirs 810a, 810b pressurize the fluid reservoirs 810a, 810b and dispense the fluid from the fluid reservoirs 810a, 810b. In the second, locked position, the torsion spring 804 is inhibited from applying the torque to the plunger assembly 802.

The lock system 806 moves the plunger assembly 802 between the first, unlocked position (in which fluid or insulin flows from the fluid reservoirs 810a, 810b) and a second, locked position (in which fluid is inhibited from flowing from the fluid reservoirs 810a, 810b). In one example, with reference to FIG. 20, the lock system 806 includes a lock plate 910 and a lock spring 912. The lock plate 910 is annular, and includes a first plate side 914 opposite a second plate side 916. The lock plate 910 also defines a plate bore 918 through the first plate side 914 and the second plate side 916. The lock plate 910 may be composed of a suitable biocompatible material, including, but not limited to a biocompatible polymer-based material, metal or metal alloy, which may be molded, printed, cast, stamped, etc. The first plate side 914 and the second plate side 916 are substantially planar or flat. With reference to FIG. 20, the first plate side 914 includes a plate lock surface 915. In this example, the plate lock surface 915 is defined about a perimeter or circumference of the lock plate 910 and includes the plurality of teeth 915a. The plurality of teeth 915a cooperate with the plurality of teeth 841a to lock the plunger assembly 802, and thus, the pump 104 in the second, locked position. As shown in FIG. 21, the second plate side 916 includes a collar 916a, which assists in aligning the lock spring 912 relative to the first pump housing 800. The plate bore 918 defines the keyed grooves 824, which engage with the keyed projections 822 of the first pump housing 800 to couple the lock plate 910 to the first pump housing 800.

Figure 23:
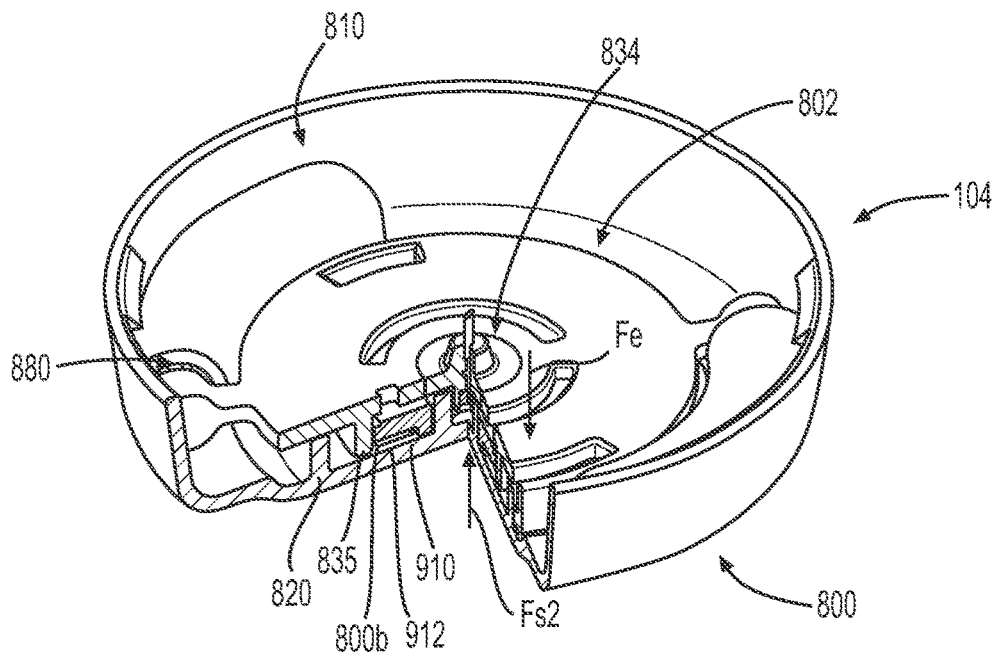
FIG. 23 is a partially cross-sectional view of the pump, taken along line 23-23 of FIG. 19, which illustrates the plunger assembly (and the pump) in the first, unlocked position.
Figure 24:
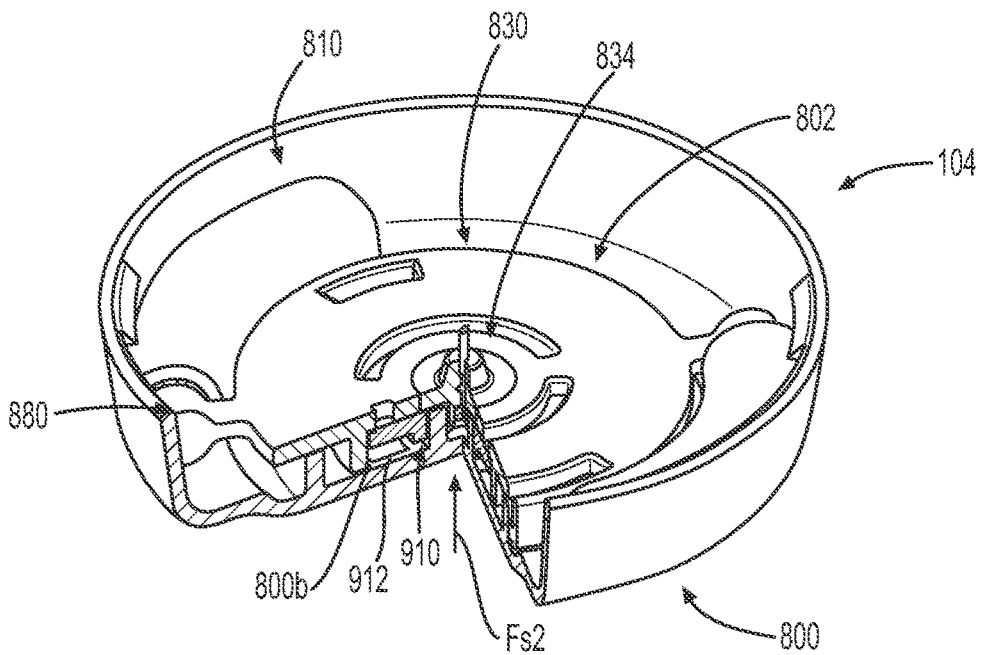
FIG. 24 is a partially cross-sectional view of the pump, taken along line 23-23 of FIG. 19, which illustrates the plunger assembly (and the pump) in the second, locked position.

The lock spring 912 is a wave spring, which biases the lock plate 910 into the plunger assembly 802 to position the plunger assembly 802 in the second, locked position (FIG. 24). The lock spring 912 is composed of a metal or metal alloy, such as a spring steel, and may be shaped to form the lock spring 912. The lock spring 912 includes a plurality of undulations 912a, which cooperate to form a compression spring. The lock spring 912 is compressible upon the application of an external force Fe to the plunger base 830 to move the plunger assembly 802 from the second, locked position to the first, unlocked position (FIG. 23). In one example, with reference to FIG. 23, the external force Fe is a force applied to the plunger assembly 802 in a vertical direction to move the plunger assembly 802 toward the first pump housing 800. Thus, the plunger assembly 802 is movable from the second, locked position (FIG. 24) to the first, unlocked position (FIG. 23) in a first direction (which is vertical in this example) and is movable in a second direction (counterclockwise) to dispense the fluid from the fluid reservoirs 810a, 810b. The lock spring 912 exerts a spring force Fs2 (FIG. 24) in a direction toward a first end 800a of the first pump housing 800 to bias the plunger assembly 802 in the second, locked position. In the second, locked position, the teeth 915a, 814a engage, and inhibit a movement or rotation of the plunger assembly 802 relative to the reservoirs 810a, 810b.

In one example, with reference to FIG. 20, in order to assemble the pump 104, with the plunger base 830 formed and coupled to or integrally formed with the plunger arms 832a, 832b, the plungers 884 are coupled to the second ends 898 of the respective plunger arms 832a, 832b. With the cannula 852 coupled to the cannula coupling portion 850, the cannula coupling portion 850 is coupled to the plunger base 830. With the first pump housing 800 formed, the lock spring 912 and the lock plate 910 are coupled to the first pump housing 800. The torsion spring 804 is coupled to the first pump housing 800. The fluid reservoirs 810a, 810b are filled with the fluid, such as insulin, and the plunger assembly 802 is coupled to the first pump housing 800 such that the plungers 884 form a seal with the fluid reservoirs 810a, 810b to contain the fluid within the fluid reservoirs 810a, 810b.

With the pump 104 assembled, the pump 104 can be coupled to the wearable infusion port 102 or the wearable infusion port 500 to supply the respective wearable infusion port 102 or the wearable infusion port 500 with the fluid or insulin. In one example, with reference to FIG. 18, the pump 104 is coupled to the wearable infusion port 102. As the cannula 852 is positioned within the first needle port 132, the second end 850b of the cannula coupling portion 850 contacts the first surface 110a of the first housing 110. The contact between the cannula coupling portion 850 and the first surface 110a creates the external force Fe, which overcomes the spring force Fs2 exerted by the lock spring 912 and causes the lock plate 910 to move toward a first end 800a of the first pump housing 800 (FIG. 23). As the lock plate 910 moves towards the first end 800a, the torsion spring 804 applies a force to the annular flange 835 to move or rotate the plunger assembly 802 relative to the fluid reservoirs 810a, 810b. When the lock plate 910 contacts a surface 800b of the first pump housing 800, the plunger assembly 802 (and the pump 104) is in the first, unlocked position (FIG. 23).

In the first, unlocked position, the torsion spring 804 applies the torque to the annular flange 835 to drive, move or rotate the plunger assembly 802 relative to the first pump housing 800. The movement or rotation of the plunger assembly 802 causes the plunger arms 832a, 832b to advance into the respective fluid reservoirs 810a, 810b. The advancement of the plunger arms 832a, 832b into the fluid reservoirs 810a, 810b, in turn, causes an increase in pressure in the fluid reservoirs 810a, 810b, which with reference to FIG. 21, causes the fluid or insulin to flow through the inlet 906. The fluid or insulin flows from the inlet 906 into the respective body conduit 900, through the respective connector conduit 890, through the respective base branch 838a, 838b, through the respective branch 856a, 856b (FIG. 20C), through into the cannula 852 and into the first needle port 132 of the wearable infusion port 102. Thus, the inlet 906, the body conduit 900 and the connector conduit 890 of the respective plunger arm 832a, 832b along with the respective base branch 838a, 838b and the respective branch 856a, 856b cooperate to define an internal conduit of the plunger assembly 802 that cooperates to dispense the fluid contained within the respective fluid reservoir 810a, 810b into the cannula 852, and from the cannula 852, into the wearable infusion port 102. Depending upon the volume that may be received by the wearable infusion port 102, 500, the plunger arms 832a, 832b may advance within the respective fluid reservoirs 810a, 810b until all of the fluid or insulin contained within the fluid reservoirs 810a, 810b is dispensed and the plungers 884 contact the second reservoir ends 816 of the respective fluid reservoirs 810a, 810b as shown in FIG. 22.

With reference back to FIG. 18, once the selected amount of insulin has been dispensed into the wearable infusion port 102, the user moves the pump 104 from the first surface 110a of the first housing 110 of the wearable infusion port 102. The movement of the pump 104 from the first housing 110 removes the external force Fe created by the contact between the cannula coupling portion 850 and the first housing 110, and the spring force Fs2 exerted by the lock spring 912 moves the lock plate 910 relative to the surface 800b of the first pump housing 800 to the second, locked position (FIG. 24) to fix the plunger assembly 802, and thus, the pump 104 in the second, locked position. In the second, locked position, fluid is inhibited from being dispensed by the pump 104.

Thus, the pump 104 enables a user to supply a fluid, such as insulin, to a wearable infusion port or other device in increments, which is beneficial to users who require multiple fluid infusions over the course of a day. Moreover, the pump 104 enables a user to carry multiple doses of the fluid or insulin with them in a single housing, and eliminates the need to carry multiple syringes. It should be noted that while not shown herein, the pump 104 may be coupled to an adhesive patch, such as the adhesive patch 122, and coupled to the anatomy as a patch pump.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A wearable infusion port for infusing a fluid, comprising:
    a first housing that defines an inlet port to receive the fluid;
    a second housing coupled to the first housing, the second housing to be coupled to an anatomy;
    a valve assembly fluidly coupled to the inlet port to receive the fluid, the valve assembly including a rotor having a rotor conduit that is selectively fluidly coupled to an outlet conduit of the valve assembly, the valve assembly movable from a closed state to an opened state to dispense the fluid via rotation of the rotor;
    a cannula assembly extending through the first housing and the second housing, the cannula assembly including a cannula fluidly coupled to the valve assembly to receive the fluid, the cannula to be coupled to the anatomy to infuse the fluid into the anatomy; and
    a flow sensor fluidly coupled to the inlet port and the cannula, the flow sensor fluidly coupled upstream from the cannula to observe an amount of fluid received by the cannula.

2. The wearable infusion port of claim 1, wherein the valve assembly is enclosed by the first housing and the second housing, and the valve assembly includes a valve housing and a shaft, and the shaft is movable relative to the valve housing to rotate the rotor.

3. The wearable infusion port of claim 2, further comprising an actuator pinion having a plurality of teeth, wherein the shaft includes a plurality of shaft teeth that engage with the plurality of teeth of the actuator pinion to move the rotor relative to the valve housing.

4. The wearable infusion port of claim 3, further comprising an end plate coupled to the rotor and the actuator pinion, and the actuator pinion drives the end plate to move the rotor relative to the valve housing.

5. The wearable infusion port of claim 2, further comprising an actuator wire coupled to the shaft, the actuator wire movable between a first state and a second state to move the shaft, and in the second state the valve assembly is in the opened state.

6. The wearable infusion port of claim 5, wherein the shaft defines a shaft conduit, and the movement of the shaft relative to the valve housing fluidly couples the shaft conduit with the cannula.

7. The wearable infusion port of claim 1, further comprising a control system that receives the observation from the flow sensor to transmit the amount of fluid received by the cannula to a remote device.

8. The wearable infusion port of claim 1, further comprising a physiological characteristic sensor coupled to the first housing proximate an end of the first housing and spaced apart from the inlet port, and the physiological characteristic sensor is to be coupled to the anatomy to observe a physiological characteristic associated with the anatomy.

9. A wearable infusion port for infusing a fluid, comprising:
    a first housing that defines an inlet port to receive the fluid;
    a second housing coupled to the first housing, the second housing to be coupled to an anatomy;
    a valve assembly fluidly coupled to the inlet port to receive the fluid, the valve assembly including a rotor having a rotor conduit that is selectively fluidly coupled to an outlet conduit of the value assembly, the valve assembly movable, via rotation of the rotor, from a closed state to an opened state to dispense the fluid;
    a cannula assembly extending through the first housing and the second housing, the cannula assembly including a cannula fluidly coupled to the valve assembly to receive the fluid, the cannula to be coupled to the anatomy to infuse the fluid into the anatomy; and
    a physiological characteristic sensor coupled to the first housing proximate an end of the first housing and spaced apart from the inlet port, the physiological characteristic sensor to be coupled to the anatomy to observe a physiological characteristic associated with the anatomy.

10. The wearable infusion port of claim 9, wherein the valve assembly is enclosed by the first housing and the second housing, and the valve assembly includes a valve housing and a shaft, and the shaft is movable relative to the valve housing to rotate the rotor.

11. The wearable infusion port of claim 10, further comprising an actuator pinion having a plurality of teeth, wherein the shaft includes a plurality of shaft teeth that engage with the plurality of teeth of the actuator pinion to move the rotor relative to the valve housing.

12. The wearable infusion port of claim 11, further comprising an end plate coupled to the rotor and the actuator pinion, and the actuator pinion drives the end plate to move the rotor relative to the valve housing.

13. The wearable infusion port of claim 10, further comprising an actuator wire coupled to the shaft, the actuator wire movable between a first state and a second state to move the shaft, and in the second state the valve assembly is in the opened state.

14. The wearable infusion port of claim 9, further comprising a flow sensor fluidly coupled to the inlet port and the cannula, the flow sensor fluidly coupled upstream from the cannula to observe an amount of fluid received by the cannula.

15. The wearable infusion port of claim 14, further comprising a control system that receives the observation from the flow sensor and the observation from the physiological characteristic sensor to transmit the observations to a remote device.

16. A wearable infusion port for infusing a fluid, comprising:
    a first housing that defines an inlet port to receive the fluid;
    a second housing coupled to the first housing, the second housing to be coupled to an anatomy;
    a valve assembly fluidly coupled to the inlet port to receive the fluid, the valve assembly including a valve housing and a rotor defining at least one rotor conduit downstream from the inlet port, the rotor being rotatably movable relative to the valve housing to move the valve assembly between a closed state and an opened state to dispense the fluid; and
    a cannula assembly extending through the first housing and the second housing, the cannula assembly including a cannula fluidly coupled to the valve assembly to receive the fluid in the opened state, the cannula to be coupled to the anatomy to infuse the fluid into the anatomy.

17. The wearable infusion port of claim 16, further comprising a flow sensor fluidly coupled to the inlet port and the cannula, the flow sensor fluidly coupled upstream from the cannula to observe an amount of fluid received by the cannula.

18. The wearable infusion port of claim 16, further comprising an actuator wire coupled to the shaft, the actuator wire movable between a first state and a second state to move the shaft, and in the second state the valve assembly is in the opened state.

* * * * *

UNITED STATES PATENT AND TRADEMARK OFFICE
CERTIFICATE OF CORRECTION

| | |
|---|---|
| PATENT NO. | : 11,559,624 B2 |
| APPLICATION NO. | : 16/691506 |
| DATED | : January 24, 2023 |
| INVENTOR(S) | : Larson et al. |

It is certified that error appears in the above-identified patent and that said Letters Patent is hereby corrected as shown below:

In the Claims

In Column 45, in Claim 9, Line 34, delete "value" and insert -- valve --, therefor.

Signed and Sealed this
Twenty-eighth Day of February, 2023

*Katherine Kelly Vidal*

Katherine Kelly Vidal
*Director of the United States Patent and Trademark Office*